(12) United States Patent
Shukla et al.

(10) Patent No.: US 9,944,639 B2
(45) Date of Patent: Apr. 17, 2018

(54) QUINOLIZINONE DERIVATIVES AS PI3K INHIBITORS

(71) Applicant: Lupin Limited, Mumbai, Maharashtra (IN)

(72) Inventors: Manojkumar Ramprasad Shukla, Pune (IN); Nirmal Kumar Jana, Pune (IN); Sachin Jaysing Mahangare, Pune (IN); Prashant Popatrao Vidhate, Pune (IN); Dipak Raychand Lagad, Pune (IN); Anand Jagannath Tarage, Pune (IN); Sanjeev Anant Kulkarni, Pune (IN); Venkata P. Palle, Pune (IN); Rajender Kumar Kamboj, Pune (IN)

(73) Assignee: Lupin Limited, Mumbai (IN)

(*) Notice: Subject to any disclaimer, the term of this patent is extended or adjusted under 35 U.S.C. 154(b) by 0 days.

(21) Appl. No.: 15/323,565

(22) PCT Filed: Jul. 1, 2015

(86) PCT No.: PCT/IB2015/054958
§ 371 (c)(1),
(2) Date: Jan. 3, 2017

(87) PCT Pub. No.: WO2016/001855
PCT Pub. Date: Jan. 7, 2016

(65) Prior Publication Data
US 2017/0137421 A1    May 18, 2017

(30) Foreign Application Priority Data
Jul. 4, 2014   (IN) .................. 2182/MUM/2014

(51) Int. Cl.
| C07D 519/00 | (2006.01) |
| A61K 31/52 | (2006.01) |
| A61K 31/519 | (2006.01) |
| C07D 471/04 | (2006.01) |
| C07D 473/34 | (2006.01) |
| C07D 473/16 | (2006.01) |
| C07D 513/04 | (2006.01) |

(52) U.S. Cl.
CPC ......... *C07D 471/04* (2013.01); *C07D 473/16* (2013.01); *C07D 473/34* (2013.01); *C07D 513/04* (2013.01); *C07D 519/00* (2013.01)

(58) Field of Classification Search
CPC ..... C07D 519/00; A61K 31/52; A61K 31/519
USPC .......... 544/262, 280, 264; 514/262.1, 265.1, 514/263.22
See application file for complete search history.

(56) References Cited

U.S. PATENT DOCUMENTS

| 4,235,871 | A | 11/1980 | Papahadjopoulos et al. |
| 4,501,728 | A | 2/1985 | Geho et al. |
| 4,837,028 | A | 6/1989 | Allen et al. |
| 5,019,369 | A | 5/1991 | Presant et al. |
| 2011/0015212 | A1 | 1/2011 | Li et al. |
| 2014/0296260 | A1 | 10/2014 | Askew et al. |
| 2016/0067249 | A1 | 3/2016 | Askew et al. |

FOREIGN PATENT DOCUMENTS

| CN | 102838600 A | 12/2012 |
| CN | 102838601 A | 12/2012 |
| CN | 104418849 A | 3/2015 |
| CN | 105130966 A | 12/2015 |
| CN | 105130984 A | 12/2015 |
| WO | WO 2001/081346 A2 | 11/2001 |
| WO | WO 2003/035075 A1 | 5/2003 |
| WO | WO 2005/016348 A1 | 2/2005 |
| WO | WO 2005/016349 A1 | 2/2005 |
| WO | WO 2005/067901 A2 | 7/2005 |
| WO | WO 2005/112935 A1 | 12/2005 |
| WO | WO 2005/113554 A2 | 12/2005 |
| WO | WO 2005/113556 A1 | 12/2005 |
| WO | WO 2005/117889 A1 | 12/2005 |
| WO | WO 2005/120511 A1 | 12/2005 |
| WO | WO 2006/089106 A2 | 8/2006 |

(Continued)

OTHER PUBLICATIONS

Ali et al., "Mutational Spectra of PTEN/MMAC1 Gene: a Tumor Suppressor With Lipid Phosphatase Activity", *J. Natl. Cancer Inst.* vol. 91, No. 22, pp. 1922-1932 (1999).
Berge S.M. et al., "Pharmaceutical Salts, a review article", *Journal of Pharmaceutical Sciences*, (1977), vol. 66, pp. 1-19.
Brana et al., "Clinical development of phosphatidylinositol 3-kinase inhibitors for cancer treatment", *BMC Medicine*, vol. 10, No. 161, pp. 1-15 (2012).
Campbell et al., "Mutation of the PIK3CA Gene in Ovarian and Breast Cancer", *Cancer Res.* vol. 64, pp. 7678-7681 (2004).
Cantley et al., "The Phosphoinositide 3-Kinase Pathway", *Science*, vol. 296, pp. 1655-1657 (2002).
Cantrell et al., "Phosphoinositide 3-kinase signaling pathways", *J. Cell. Sci.* Vo. 114, No. 8, pp. 1439-1445 (2001).

(Continued)

*Primary Examiner* — Susanna Moore
(74) *Attorney, Agent, or Firm* — Leydig, Voit & Mayer, Ltd.

(57) ABSTRACT

Disclosed are compounds of formula (I), their tautomeric forms, stereoisomers, and pharmaceutically acceptable salts thereof, wherein $R^1$-$R^4$, and n are as defined in the specification, pharmaceutical compositions including a compound, tautomer, stereoisomer, or salt thereof, and methods of treating or preventing diseases or disorders, for example, cancer, that are amenable to treatment or prevention by inhibiting the PI3K enzyme of a subject.

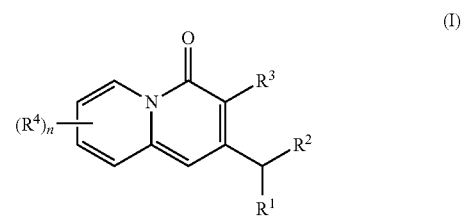

(I)

22 Claims, No Drawings

(56) References Cited

FOREIGN PATENT DOCUMENTS

| | | |
|---|---|---|
| WO | WO 2008/064018 A1 | 5/2008 |
| WO | WO 2008/118454 A2 | 10/2008 |
| WO | WO 2008/118455 A1 | 10/2008 |
| WO | WO 2008/118468 A1 | 10/2008 |
| WO | WO 2008/127226 A2 | 10/2008 |
| WO | WO 2009/064802 A2 | 5/2009 |
| WO | WO 2009/088986 A1 | 7/2009 |
| WO | WO 2009/088990 A1 | 7/2009 |
| WO | WO 2010/036380 A1 | 4/2010 |
| WO | WO 2010/111432 A1 | 9/2010 |
| WO | WO 2010/123931 A1 | 10/2010 |
| WO | WO 2010/129816 A2 | 11/2010 |
| WO | WO 2010/151735 A2 | 12/2010 |
| WO | WO 2010/151740 A2 | 12/2010 |
| WO | WO 2010/151791 A1 | 12/2010 |
| WO | WO 2011/008302 A2 | 1/2011 |
| WO | WO 2011/008487 A1 | 1/2011 |
| WO | WO 2011/011550 A1 | 1/2011 |
| WO | WO 2011/048111 A1 | 4/2011 |
| WO | WO 2011/055215 A1 | 5/2011 |
| WO | WO 2011/058112 A1 | 5/2011 |
| WO | WO 2011/075628 A1 | 6/2011 |
| WO | WO 2011/075643 A1 | 6/2011 |
| WO | WO 2011/123751 A2 | 10/2011 |
| WO | WO 2011/130342 A1 | 10/2011 |
| WO | WO 2011/146882 A1 | 11/2011 |
| WO | WO 2011/156759 A1 | 12/2011 |
| WO | WO 2012/003262 A1 | 1/2012 |
| WO | WO 2012/003264 A1 | 1/2012 |
| WO | WO 2012/003271 A1 | 1/2012 |
| WO | WO 2012/003274 A1 | 1/2012 |
| WO | WO 2012/003278 A1 | 1/2012 |
| WO | WO 2012/040634 A1 | 3/2012 |
| WO | WO 2012/052753 A1 | 4/2012 |
| WO | WO 2012/061696 A1 | 5/2012 |
| WO | WO 2012/064973 A2 | 5/2012 |
| WO | WO 2012/068343 A1 | 5/2012 |
| WO | WO 2012/087784 A1 | 6/2012 |
| WO | WO 2012/097000 A1 | 7/2012 |
| WO | WO 2012/125510 A1 | 9/2012 |
| WO | WO 2012/125629 A1 | 9/2012 |
| WO | WO 2012/146666 A1 | 11/2012 |
| WO | WO 2013/012915 A1 | 1/2013 |
| WO | WO 2013/012918 A1 | 1/2013 |
| WO | WO 2013/032591 A1 | 3/2013 |
| WO | WO 2013/052699 A2 | 4/2013 |
| WO | WO 2013/082540 A1 | 6/2013 |
| WO | WO 2013/116562 A1 | 8/2013 |
| WO | WO 2013/136075 A1 | 9/2013 |
| WO | WO 2013/136076 A1 | 9/2013 |
| WO | WO 2013/152150 A1 | 10/2013 |
| WO | WO 2013/154878 A1 | 10/2013 |
| WO | WO 2014/004470 A1 | 1/2014 |
| WO | WO 2014/006572 A1 | 1/2014 |
| WO | WO 2014/015523 A1 | 1/2014 |
| WO | WO 2014/015675 A1 | 1/2014 |
| WO | WO 2014/015675 A1 | 1/2014 |
| WO | WO 2014/023083 A1 | 2/2014 |
| WO | WO 2014/028665 A1 | 2/2014 |
| WO | WO 2014/060431 A1 | 4/2014 |
| WO | WO 2014/060432 A1 | 4/2014 |
| WO | WO 2014/071105 A1 | 5/2014 |
| WO | WO 2014/071109 A1 | 5/2014 |
| WO | WO 2014/100765 A1 | 6/2014 |
| WO | WO 2014/100767 A1 | 6/2014 |
| WO | WO 2014/106800 A2 | 7/2014 |
| WO | WO 2014/124757 A1 | 8/2014 |
| WO | WO 2014/128612 A1 | 8/2014 |
| WO | WO 2014/140597 A1 | 9/2014 |
| WO | WO 2014/201409 A1 | 12/2014 |
| WO | WO 2015/001491 A1 | 1/2015 |
| WO | WO 2015/042077 A1 | 3/2015 |
| WO | WO 2015/042078 A2 | 3/2015 |
| WO | WO 2015/042497 A2 | 3/2015 |
| WO | WO 2015/143012 A1 | 9/2015 |
| WO | WO 2015/168079 A1 | 11/2015 |
| WO | WO 2015/175579 A1 | 11/2015 |
| WO | WO 2015/191726 A1 | 12/2015 |
| WO | WO 2015/191745 A1 | 12/2015 |
| WO | WO 2015/191752 A1 | 12/2015 |
| WO | WO 2015/200352 A1 | 12/2015 |
| WO | WO 2016/066142 A1 | 5/2016 |

OTHER PUBLICATIONS

Ciapetti et al., "Chapter 15—Molecular Variations Based on Isosteric Replacements", *The Practice of Medicinal Chemistry*, 3rd Ed., pp. 290-342 (2008).

Cully et al., "Beyond PTEN mutations: the PI3K pathway as an integrator of multiple inputs during tumorigenesis", *Nat. Rev. Cancer*, vol. 6, pp. 184-192 (2006).

Cushing et al., "Discovery and in Vivo Evaluation of (S)-N-(1-(7-Fluoro-2-(pyridin-2-yl)quinolin-3-yl)ethyl)-9H-purin-6-amine (AMG319) and Related PI3Kδ Inhibitors for Inflammation and Autoimmune Disease", *Journal of Medicinal Chemistry*, vol. 58, No. 1, pp. 480-511 (2015).

Deluca et al., "Parenteral Drug-Delivery Systems," *Pharmaceutics and Pharmacy Practice*, Chapter 8, J.B. Lippincott Company, Philadelphia, PA, pp. 238-250 (1982).

Edling et al., "Key Role of Phosphoinositide 3-Kinase Class IB in Pancreatic Cancer", *Clin. Cancer Res.* vol. 16, No. 20, pp. 4928-4937 (2010).

El Haibi et al. "PI3Kp110-, Src-, FAK-dependent and DOCK2-independent migration and invasion of CXCL13-stimulated prostate cancer cells", *Mol. Cancer* vol. 9, No. 85 pp. 1-9 (2010).

He et al., "Molecular mechanism of membrane targeting by the GRP1 PH domain", *J. Lipid Res.*, vol. 48, pp. 1807-1815 (2008).

Hickey et al., "BCR-ABL Regulates Phosphatidylinositol 3-kinase-p110γ Transcription and Activation and Is Required for Proliferation and Drug Resistance", *J. Biol. Chem.*, vol. 281, No. 5, pp. 2441-2450 (2006).

Ikenoue et al., "Functional Analysis of PIK3CA Gene Mutations in Human Colorectal Cancer", *Cancer Res.*, vol. 65, No. 11, pp. 4562-4567 (2005).

Isakoff et al. "Breast Cancer-Associated PIK3CA Mutations Are Oncogenic in Mammary Epithelial Cells", *Cancer Res.*, vol. 65, No. 23, pp. 10992-11000 (2005).

Janku et al., "PIK3CA Mutations Frequently Coexist with RAS and BRAF Mutations in Patients with Advanced Cancers", *PLOS One*, vol. 6, No. 7, pp. 1-8 (2011).

Kang et al., "Oncogenic transformation induced by the p110β, -γ, and -δ isoforms of class I phosphoinositide 3-kinase", *Proc. Natl. Acad. Sci. USA*, vol. 103, No. 5, pp. 1289-1294 (2006).

Knobbe et al., "Genetic alteration and expression of the phosphoinosito1-3-kinase/Akt pathway genes PIK3CA and PIKE in human glioblastomas", *Neuropathol. Appl. Neurobiol.* vol. 31, pp. 486-490 (2005).

Liu et al., "Targeting the phosphoinositide 3-kinase pathway in cancer", *Nat. Rev. Drug Discov.*, vol. 8, pp. 627-644 (2009).

LoPiccolo et al., "Targeting the PI3K/Akt/mTOR pathway: Effective combinations and clinical considerations", *Drug Resist. Updat.*, vol. 11, pp. 32-50 (2008).

Remington's Pharmaceutical Sciences, Mack Publishing Company, p. 1445 (1985).

Samuels et al., "High Frequency of Mutations of the PIK3CA Gene in Human Cancers", *Science*, vol. 304, p. 554 (2004).

Sujobert et al., "Essential role for the p110δ isoform in phosphoinositide 3-kinase activation and cell proliferation in acute myeloid leukemia", *Blood*, vol. 106, No. 3, pp. 1063-1066 (2005).

Szoka, et al., "Comparative Properties and Methods of Preparation of Lipid Vesicles (Liposomes)," *Annual Review of Biophysics & Bioengineering*, vol. 9, pp. 467-508 (1980).

Torbett et al., "A chemical screen in diverse breast cancer cell lines reveals genetic enhancers and suppressors of sensitivity to PI3K isoform-selective inhibition", *Biochem. J.*, vol. 415, pp. 97-110 (2008).

(56) References Cited

OTHER PUBLICATIONS

Trissel, "Intravenous Infusion Solutions," *ASHP Handbok on Injectable Drugs*, Fourth Edition, American Society of Hospital Pharmacists, Inc., Bethesda, MD, pp. 622-630 (1986).
Vanhaesebroeck et al. "Synthesis and Function of 3-Phosphorylated Inositol Lipids", *Annu. Rev. Biochem.*, vol. 70, pp. 535-602 (2001).
Vanhaesebroeck et al., "The emerging mechanisms of isoform-specific PI3K signaling", *Nat. Rev. Mol. Cell Biol.*, vol. 11, pp. 329-341 (2010).
Vanhaesebroeck et al., "p110δ, a novel phosphoinositide 3-kinase in leukocytes", *Proc. Natl. Acad. Sci. USA*, vol. 94, pp. 4330-4335 (1997).
Vogt et al., Cancer-specific mutations in phosphatidylinositol 3-kinase *Trends Biochem. Sci.*, vol. 32, No. 7, pp. 342-349 (2007).
Wasserman et al., "Clinical Comparison of the Nitrosoureas", *Cancer*, vol. 36, pp. 1258-1268 (1975).
Wee et al., "PTEN-deficient cancers depend on PIK3CB", *Proc. Natl. Acad. Sci.* USA, vol. 105, No. 35, pp. 13057-13062 (2008).
Wymann M. et al., "Structure and function of phosphoinositide 3-kinases", *Biochim. Biophys. Acta*, 1436, pp. 127-150 (1998).
Zhao et al., "Class I PI3K in oncogenic cellular transformation", *Oncogene*, vol. 27, pp. 5486-5496 (2008).
Zhao et al., "The oncogenic properties of mutant p110α and p110β phosphatidylinositol 3-kinases in human mammary epithelial cells", *Proc. Natl. Acad. Sci.* USA, vol. 102, No. 51, pp. 18443-18448 (2005).
European Patent Office, International Search Report issued in International Application No. PCT/IB2015/054958, 3 pp. (Aug. 26, 2015).
European Patent Office, Written Opinion issued in International Application No. PCT/IB2015/054958, 5 pp. (Aug. 26, 2015).
Al-Alwan et al., "Requirement for Phosphoinositide 3-Kinase p110δ Signaling in B Cell Antigen Receptor-Mediated Antigen Presentation", *J Immunol.*, 178(4):2328-35 (2007).
Ali et al., "Isoform-Specific Functions of Phosphoinositide 3-Kinases: p110δ but Not p110γ Promotes Optimal Allergic Responses in Vivo", *J. Immunol.*, 180(4):2538-44 (2008).
Ali et al., "Essential role for the p110 δ phosphoinositide 3-kinase in the allergic response", *Nature*, 431(7011):1007-11(2004).
Bansal et al., "The Molecular Biology of Endometrial Cancers and the Implications for Pathogenesis, Classification, and Targeted Therapies", *Cancer Control*, 16(1):8-13 (2009).
Barber et al., "Class IB-Phosphatidylinositol 3-Kinase (PI3K) Deficiency Ameliorates IA-PI3K-Induced Systemic Lupus but Not T Cell Invasion", *J. Immunol.*, 176(1): 589-93 (2006).
Bartok et al., "Phosphoinositide 3-kinase Delta (PI3K) Regulation and Function in RA", *Arthritis Rheum*, 62 Suppl 10:362 Abstract (2010).
Bilancio et al., "Key role of the p110 δ isoform of PI3K in B-cell antigen and IL-4 receptor signaling: comparative analysis of genetic and pharmacologic interference with p110 δ function in B cells", *Blood*, 107(2):642-50 (2006).
Billottet et al., "A selective inhibitor of the p110 δisoform of PI3-kinase inhibits AML cell proliferation and survival and increases the cytotoxic effects of VP16", *Oncogene*, 25(50):6648-59 (2006).
Billottet et al., "Inhibition of Class I Phosphoinositide 3-Kinase Activity Impairs Proliferation and Triggers Apoptosis in Acute Promyelocytic Leukemia without Affecting Atra-Induced Differentiation", *Cancer Res.*, 69(3):1027-1036 (2009).
Brzezianska et al., "A minireview: the role of MAPK/ERK and PI3K/Akt pathways in thyroid follicular cell-derived neoplasm", *Front Biosci.*, 16:422-39 (2011).
Chapuis et al., "Dual Inhibition of PI3K and mTORC1/2 Signaling by NVP-BEZ235 as a New Therapeutic Strategy for Acute Myeloid Leukemia", Clin. Cancer Res., 16(22):5424-5435 (2010).
Chen et al., "Characterization of Structurally Distinct, Isoform-Selective Phosphoinositide 3'-Kinase Inhibitors in Combination with Radiation in the Treatment of Glioblastoma", *Mol. Cancer. Ther.*, 7(4):841-850 (2008).

Clayton et al., "A crucial role for the p110delta subunit of phosphatidylinositol 3-kinase in B cell development and activation", *J. Exp. Med.*, 196:753-763 (2002).
Condliffe et al., "Sequential activation of class IB and class IA PI3K is important for the primed respiratory burst of human but not murine neutrophils", *Blood*, 106(4):1432-40 (2005).
Courtney et al., "The PI3K Pathway as Drug Target in Human Cancer", *J. Clin. Oncol.*, 28(6):1075-1083 (2010).
Dil et al., "Role of phosphoinositide 3-kinase p110 delta in TLR4- and TLR9-mediated B cell cytokine production and differentiation", *Mol. Immunol.*, 46(10):1970-8 (2009).
Doukas et al., "Aerosolized Phosphoinositide 3-Kinase γ/δ Inhibitor TG100-115 [3-[2,4-Diamino-6-(3-hydroxyphenyl)pteridin-7-yl]phenol] as a Therapeutic Candidate for Asthma and Chronic Obstructive Pulmonary Disease", *J Pharmacol Exp Ther.*, 328(3):758-65 (2009).
Durand et al., "Phosphoinositide 3-Kinase p110 δ Regulates Natural Antibody Production, Marginal Zone and B-1 B Cell Function, and Autoantibody Responses", *J. lmmunol.*, 183(9):5673-84 (2009).
Fresno et al., "PI3K/Akt signalling pathway and cancer", *Cancer Treat Rev.*, 30(2):193-204 (2004).
Fung-Leung, "Phosphoinositide 3-kinase delta (PI3Kδ) in leukocyte signaling and function", *Cellular Signalling*, 23: 603-608 (2011).
Furukawa, "Molecular Targeting Therapy for Pancreatic Cancer: Current Knowledge and Perspectives from Bench to Bedside", *J. Gastroenterol.*, 43(12):905-911 (2008).
Garcon et al., "CD28 provides T-cell costimulation and enhances PI3K activity at the immune synapse independently of its capacity to interact with the p85/p110 heterodimer", *Blood*, 111(3):1464-71 (2008).
Guo et al., "The p110δ of PI3K plays a critical role in NK cell terminal maturation and cytokine/chemokine generation", *J Exp Med.*, 205(10):2419-35 (2008).
Haylock-Jacobs et al., "PI3Kδ drives the pathogenesis of experimental autoimmune encephalomyelitis by inhibiting effector T cell apoptosis and promoting Th17 differentiation", *J Autoimmun.*, 2011; 36(3-4):278-87 (2011).
Herman et al., "Phosphatidylinositol 3-kinase delta inhibitor CAL-101 shows promising preclinical activity in chronic lymphocytic leukemia by antagonizing intrinsic and extrinsic cellular survival signals", *Blood*, 116(12):2078-2088 (2010).
Herman et al., "The role of phosphatidylinositol 3-kinase-delta in the immunomodulatory effects of lenalidomide in chronic lymphocytic leukemia", *Blood*, 117(16):4323-4327 (2011).
Herrera et al., "The dual PI3K/mTOR inhibitor BEZ235 is effective in lung cancer cell lines", *Anticancer Res.*, 31:849-854 (2011).
Ikeda et al., "PI3K/p110 delta is a novel therapeutic target in multiple myeloma", *Blood*, 116(9):1460-1468 (2010).
Jarmin et al., "T cell receptor-induced phosphoinositide-3-kinase p110δ activity is required for T cell localization to antigenic tissue in mice", *J Clin Invest.*, 118(3):1154-64 (2008).
Ji et al., "Inactivation of PI3Kγ and PI3Kδ distorts T-cell development and causes multiple organ inflammation", *Blood*, 110(8):2940-7 (2007).
Kim et al., "The multiple roles of phosphoinositide 3-kinase in mast cell biology", *Trends Immunol.*, 29(10):493-501 (2008).
Kim et al., "The p110delta catalytic isoform of PI3K is a key player in NK-cell development and cytokine secretion", *Blood*, 110(9):3202-8 (2007).
Kong et al., "Advances in development of phosphatidylinositol 3-kinase inhibitors", *Curr Med. Chem.*, 16(22):2839-54 (2009).
Konrad et al., "Phosphoinositide 3-Kinases γ and δ, Linkers of Coordinate C5a Receptor-Fc γ Receptor Activation and Immune Complex-induced Inflammation", *J Biol. Chem.*, 283(48):33296-303 (2008).
Lee et al., "Phosphoinositide 3-kinase-δ inhibitor reduces vascular permeability in a murine model of asthma", *J Allergy Clin Immunol.*, 118(2):403-9 (2006).
Lee et al., "Inhibition of phosphoinositide 3-kinase delta attenuates allergic airway inflammation and hyperresponsiveness in murine asthma model", *FASEB J.*, 20(3):455-65 (2006).
Liu et al., "The p110 delta isoform of phosphatidylinositol 3-kinase controls the quality of secondary anti-Leishmania immunity by

(56) References Cited

OTHER PUBLICATIONS regulating expansion and effector function of memory T cell subsets", *J Immunol.*, 184(6):3098-105 (2010).
Markman et al., "Status of PI3K inhibition and biomarker development in cancer therapeutics", *Ann. Oncol.*, 21(4):683-691 (2010).
Marwick et al., "Inhibition of PI3Kδ Restores Glucocorticoid Function in Smoking-induced Airway Inflammation in Mice", *Am J Respir Crit. Care Med.*, 179(7):542-8 (2009).
Mazzoletti et al., "PI3K/Akt/mTOR inhibitors in ovarian cancer", *Curr Med. Chem.*, 17(36):4433-47 (2010).
Okkenhaug et al., "The p110 δ Isoform of Phosphoinositide 3-Kinase Controls Clonal Expansion and Differentiation of Th Cells", *J Immunol.*, 177(8):5122-8 (2006).
Okkenhaug et al., "Impaired B and T Cell Antigen Receptor Signaling in p110 δ PI 3-Kinase Mutant Mice", *Science*, 297(5583):1031-4 (2002).
"Phosphoinositide 3-kinase inhibitor", *Wikipedia*, https://en.wikipedia.org/w/index.php?title=Phospholnosltide_3-kinase_inhibitor&oldid=801252421, downloaded Sep. 20, 2017 (7 pages).
Pinho, "Tissue- and Stimulus-Dependent Role of Phosphatidylinositol 3-Kinase Isoforms for Neutrophil Recruitment Induced by Chemoattractants In Vivo", *J Immunol.*, 179(11):7891-8 (2007).
Porta et al., "Phosphatidylinositol-3-kinase/Akt signaling pathway and kidney cancer, and the therapeutic potential of phosphatidylinositol-3-kinase/Akt inhibitors", *J. Urol.*, 182(6):2569-77 (2009).
Randis et al., "Role of PI3Kδ and PI3Kγ in inflammatory arthritis and tissue localization of neutrophils", *Eur J. Immunol.*, 38(5):1215-24 (2008).
Reif, "Cutting Edge: Differential Roles for Phosphoinositide 3-Kinases, p110 γ and p110δ, in Lymphocyte Chemotaxis and Homing", *J Immunol.*, 2004; 173(4):2236-40 (2004).
Rommel et al., "PI3K delta and PI3K gamma: partners in crime in inflammation in rheumatoid arthritis and beyond?", *Nat Rev Immunol.*, 7(3):191-201 (2007).
Sadhu et al., "Essential Role of Phosphoinositide 3-Kinase δ in Neutrophil Directional Movement", *J Immunol.*, 170(5):2647-54 (2003).
Saif et al., "Biology of colorectal cancer", *Cancer J.*, 16(3):196-201(2010).
Salmena et al., "Tenets of PTEN Tumor Suppression", *Cell*, 133(3):403-414 (2008).
Sarker et al., "Targeting the PI3K/AKT pathway for the treatment of prostate cancer", *Clin. Cancer Res.*, 15(15):4799-4805 (2009).
Saudemont, "p110 γ and p110 δ isoforms of phosphoinositide 3-kinase differentially regulate natural killer cell migration in health and disease", *Proc Natl Acad Sci USA.*, 106(14):5795-800 (2009).
Soond et al., "PI3K p110delta regulates T-cell cytokine production during primary and secondary immune responses in mice and humans", *Blood*, 115(11):2203-2213 (2010).
Srinivasan et al., "PI3K Kinase Signals BCR-Dependent Mature B Cell Survival", *Cell*, 139:573-586 (2009).
Tassi et al., "p110 γ and p110 δ Phosphoinositide 3-Kinase Signaling Pathways Synergize to Control Development and Functions of Murine NK Cells", *Immunity*, 27(2):214-27 (2007).
Torbett et al., "A chemical screen in diverse breast cancer cell lines reveals genetic enhancers and suppressors of sensitivity to PI3K isoform-selective inhibition", *Biochem. J.*, 415(1):97-110 (2008).
Vanhaesebroeck et al., "PI3K: from the bench to the clinic and back", *Curr. Top. Microbiol. Immunol.*, 347:1-19 (2011).
Vogt et al., "Phosphoinositide 3-kinase: from viral oncoprotein to drug target", *Virology*, 344(I):131-138 (2006).
Vogt et al., "Phosphatidylinositol 3-kinase: the oncoprotein", *Curr. Top. Microbiol. Immunol.*, 347:79-104 (2011).
Ward et al., "Therapeutic potential of phosphoinositide 3-kinase inhibitors",*Chem. Biol.*, 10(3):207-213 (2003).
Webb et al., "Cutting Edge: T Cell Development Requires the Combined Activities of the p110 γ and p110δ Catalytic Isoforms of Phosphatidylinositol 3-Kinase", *J Immunol.*, 175(5):2783-7 (2005).
Williams et al., "Discovery of dual inhibitors of the immune cell PI3Ks p110δ and p110γ: a prototype for new anti-inflammatory drugs", *Chem Biol.*, 17(2):123-34 (2010).
Zhang et al., "Genetic or pharmaceutical blockade of p110 δ phosphoinositide 3-kinase enhances IgE production", *J Allergy Clin Immunol.*, 2008; 122(4):811-819.e2 (2008).

QUINOLIZINONE DERIVATIVES AS PI3K INHIBITORS

FIELD OF THE INVENTION

The present invention relates to quinolizinone derivatives, their tautomeric forms, their stereoisomers, their pharmaceutically acceptable salts, combinations with suitable medicament, pharmaceutical compositions containing them, methods of making of quinolizinone derivatives, and their use as PI3K inhibitor.

CROSS-REFERENCE TO RELATED APPLICATIONS

The present application is the U.S. national phase of International Application No. PCT/IB2015/054958, filed on Jul. 1, 2015, which claims the benefit of Indian Provisional Patent Application Number 2182/MUM/2014, filed on Jul. 4, 2014, the disclosures of which are incorporated herein by reference in their entireties for all purposes.

BACKGROUND OF THE INVENTION

Oncogenic cellular transformation and cancer is associated with enhanced PI3K signalling as a result of mutational activation and overexpression of class I PI3K and genetic or epigenetic inactivation of PTEN (Ali et al., *J. Natl. Cancer Inst.* 1991, 1922-1932; Cantley et al., *Science* 2002, 296, 1655-1657; Campbell et al., *Cancer Res.* 2004, 64, 7678-7681; Cully et al., *Nat. Rev. Cancer* 2006, 6, 184-192; Vogt et al., *Trends Biochem. Sci.* 2007, 32, 342-349). Phosphatidylinositol 3-kinases (PI3K's), a family of lipid enzymes catalyzes the phosphorylation of the 3-OH of the inositol ring. It has a central role in regulating a wide range of cellular processes including metabolism, survival, motility, differentiation and cell activation (Vanhaesebroeck et al., *Annu. Rev. Biochem.* 2001, 70, 535). Its estimated that PI3K signalling pathway has 50-100 downstream effectors in every eukaryotic cell. These lipid enzymes are classified into 3 major classes, I, II & III, based on their structure and in vitro substrate specificity (Wymann M. and Pirola L., *Biochim. Biophys. Acta* 1998, 1436, 127). These class I PI3K kinases include four isoforms: PI3K α, β, γ and δ. Both PI3K α and PI3K β are known to be expressed ubiquitously, while PI3K γ and PI3K δ are restricted mainly to hematopoietic cells (Vanhaesebroeck et al., *Proc. Natl. Acad. Sci. USA* 1997, 94, 4330-4335). The catalytic subunit of the p110α, p110β and p110δ isoforms is constitutively bound to a p85 regulatory subunit. It's also important to know that only class I isoforms phosphorylate inositol lipids to form second messenger phosphoinositides, specifically converting PIP2 to PIP3 in the cell membrane, which then recruit downstream signaling proteins such as Bruton's tyrosin kinase (Btk), phosphatidylinositol-dependent kinase (Pdk), GRP1 and Akt (Vanhaesebroeck et al., *Nat. Rev. Mol. Cell. Biol.* 2010, 11, 329-41; Cantrell et al., *J. Cell. Sci.* 2001, 114, 1439-45; Ju He et al., *J. Lipid Res.* 2008, 48, 1807-1815). The activation of PI3K pathway is not only via RTKs, but also by RAS and GPCR (Irene Brana and Lillian L Siu., *BMC Medicine* 2012, 10, 161). The activation of PI3K pathway by RAS protein is by direct interaction with p110α, p110γ, and p110δ subunits, while GPCRs can interact with p110β and p110γ subunits (Vanhaesebroeck et al., *Nat. Rev. Mol. Cell Biol.* 2010, 11, 329-341).

The mode of regulation by upstream signalling also differs among the four PI3K isoforms. The γ isoform is linked to G protein-coupled receptors, whereas the PI3K α and PI3K δ isoforms are activated by signals from receptor tyrosine kinases. However the PI3K β isoform can accept input from both receptor tyrosine kinases and from G protein-coupled receptors (Kang et al., *Proc. Natl. Acad. Sci. USA* 2006, 103, 1289-94).

PI3K activity is functionally antagonized by phosphatase and tensin homolog (PTEN), a tumor suppressor gene that encodes a lipid phosphatase that removes the phosphate from the 3-OH position of 3-phosphoinositides, reducing the cellular pool of PI(3,4,5)P3 by converting it back to PI(4,5)P2 (Liu et al., *Nat. Rev. Drug Discov.* 2009, 8, 627-44). Loss of PTEN expression has been shown to activate the PI3K/Akt/mTOR pathway and also correlates with poor prognosis and thereby reduced survival in human cancer (LoPiccolo et al., *Drug Resist. Updat.* 2008, 11, 32-50).

PIK3CA mutations are reported in several cancer types, including glioblastoma multiforme, breast cancer, endometrial cancer, colorectal cancer and hepatocellular carcinoma. PIK3CA mutations are oncogenic per se promoting tumor formation in several preclinical models without other molecular aberrations (Ikenoue et al., *Cancer Res.* 2005, 65, 4562-4567; Isakoff et al., *Cancer Res.* 2005, 65, 10992-11000; Zhao et al., *Proc. Natl. Acad. Sci. USA* 2005, 102, 18443-18448). PI3Kα is the most frequently found mutated isoform in human cancers. It's reported that in PIK3CA gene, 80% of the mutations are clustered at three hotspots in the p110α gene that encodes the catalytic subunit: two in the helical domain (E542K and E545K) and one in the kinase domain (H1047R) (Zhao et al., *Oncogene* 2008, 27, 5486-5496). However these somatic mutations are clustered in two hot spots: exon 9 in the helical domain of p110α are common in colorectal cancer, cervical squamous and squamous cell cancer of head and neck and exon 20 in the kinase domain of p110α are common in uterine, breast cancer and ovarian cancers (Janku et al., *PLOS One* 2011, 7, 6).

The non-alpha isoforms of class I PI3K have no cancer-specific mutations, but their differential expression has been observed in several cancers. Reported data also suggests involvement of non-alpha isoforms of class I PI3K in solid tumors. Recent studies show that certain PTEN-deficient human cancer cell lines are sensitive to inactivation of p110β rather than p110α (Wee et al., *Proc. Natl. Acad. Sci. USA* 2008, 105, 13057-62; Torbett et al., *Biochem. J.* 2008, 415, 97-110). In vivo studies however suggest that p110δ isoform-specific targeting may be cytotoxic to B cells with minimal toxicity to other hematopoietic cell types. To clearly understand the functional role of p110δ in B cells, forced expression of p110δ was found to enhance transforming potential in cell lines (Kang et al., *Proc. Natl. Acad. Sci. USA* 2006, 103, 1289-94). In acute myeloblastic leukemia, p110δ isoform is consistently overexpressed and p110δ inhibitors specifically interfere with the growth of these leukemic cells, suggesting a role for p110δ in leukemogenesis (Samuels et al., *Science* 2004, 304, 554; Sujobert et al., *Blood* 2005, 106, 1063-6). However, P110γ is specifically overexpressed in human pancreatic intraepithelial neoplasia and ductal carcinoma, which correlates with increased levels of PIP$_3$ and phosphorylated Akt (Edling et al., *Clin. Cancer Res.* 2010, 16, 4928-4937; El Haibi et al., *Mol. Cancer* 2010, 9, 85). Increased expression of p110γ is also seen in chronic myeloid leukemia (Hickey and Cotter., *J. Biol. Chem.* 2006, 281, 2441-50; Knobbe et al., *Neuropathol. Appl. Neurobiol.* 2005, 31, 486-90).

Hence, it is evident that class I PI3Ks are involved in survival mechanism and progression of many cancer types and therefore is one among the most sought after targets in cancer therapeutics. So, targeting PI3K itself or downstream effectors of PI3K is an approach that has the potential to be of huge therapeutic benefit.

BRIEF SUMMARY OF THE INVENTION

In one aspect, the present invention provides a compound of formula (I), its tautomeric form, its stereoisomer, its pharmaceutically acceptable salt, its combination with suitable medicament, its pharmaceutical composition and its use as PI3K inhibitor

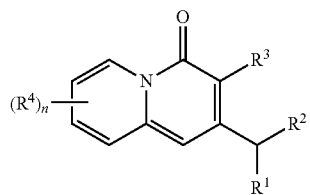
(I)

wherein,
R¹ is selected from a)

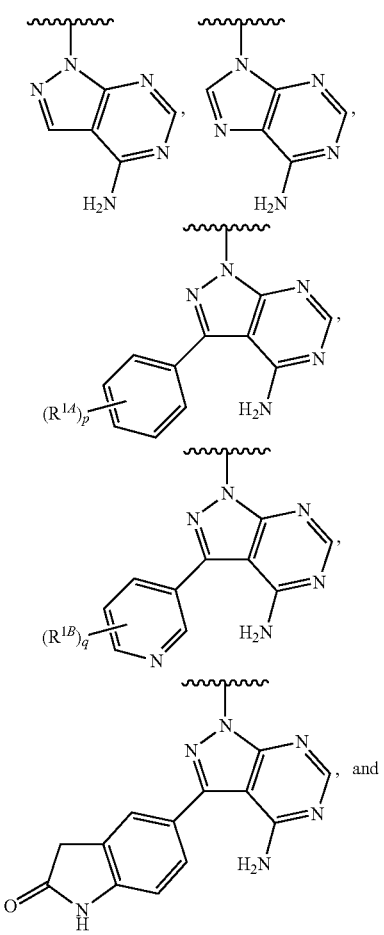

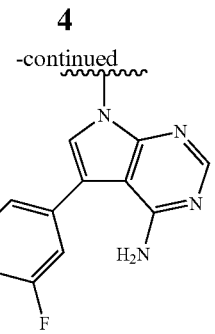

wherein,
R$^{1A}$ is independently selected at each occurrence from halogen, hydroxy, hydroxyalkyl, and —NHSO$_2$CH$_3$;
R$^{1B}$ is independently selected at each occurrence from hydroxy, alkoxy and —NHSO$_2$CH$_3$; or
b) —NH—R$^{1a}$; wherein R$^{1a}$ is selected from

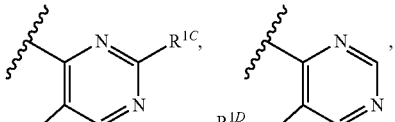

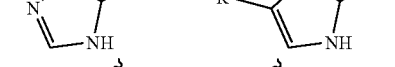

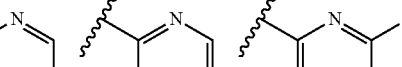

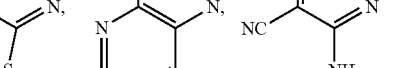

wherein,
R$^{1C}$ is selected from hydrogen, halogen, and amino; R$^{1D}$ is selected from halogen and cyano; R$^{1E}$ is selected from hydrogen and amino; R$^{1F}$ is selected from hydrogen, halogen, and alkyl;
R$^2$ is selected from hydrogen, substituted- or unsubstituted-alkyl, hydroxyalkyl, —OR$^5$, —(CH$_2$)$_m$NR$^6$R$^7$, and C(=O)—NR$^6$R$^7$;
R$^3$ is selected from substituted- or unsubstituted aryl, substituted- or unsubstituted cycloalkyl, and substituted- or unsubstituted cycloalkenyl;
R$^4$ is independently selected at each occurrence from halogen, substituted- or unsubstituted-alkyl, substituted- or unsubstituted-aryl, substituted- or unsubstituted-heteroaryl, substituted- or unsubstituted-heterocycle, substituted- or unsubstituted-carbocycle, and —OR$^5$;
R$^5$ is substituted- or unsubstituted-alkyl;
R$^6$ and R$^7$ are each independently selected from hydrogen and substituted- or unsubstituted-alkyl;
n is an integer selected from 0, 1, and 2;
m is an integer selected from 1, 2, 3, and 4;
p is an integer selected from 0, 1, and 2; and
q is an integer selected from 0, 1, and 2;
wherein:
when an 'alkyl' group is substituted, it is substituted with 1 to 3 substituents independently selected from oxo (=O), halogen, nitro, cyano, perhaloalkyl, cycloalkyl, cycloalkenyl, aryl, heteroaryl, heterocyclyl, —OR$^{8b}$, —SO$_2$R$^{8a}$, —C(=O)OR$^{8a}$, —OC(=O)R$^{8a}$, —C(=O)N(H)R$^8$, —C(=O)N(alkyl)R$^8$, —N(H)C(=O)R$^{8a}$, —N(H)R$^8$, and —N(alkyl)R$^8$;

when 'cycloalkyl', 'cycloalkenyl' and 'carbocycle' is substituted, each of them is substituted with 1 to 3 substituents independently selected from oxo (=O), halogen, nitro, cyano, alkyl, alkenyl, cycloalkyl, cycloalkenyl, perhaloalkyl, aryl, heteroaryl, heterocyclyl, —OR$^{8b}$, —SO$_2$R$^{8a}$, —C(=O)R$^{8a}$, —C(=O)OR$^{8a}$, —OC(=O)R$^{8a}$, —C(=O)N(H)R$^8$, —C(=O)N(alkyl)R$^8$, —N(H)C(=O)R$^{8a}$, —N(H)R$^8$, and —N(alkyl)R$^8$;

when the 'aryl' group is substituted, it is substituted with 1 to 3 substituents independently selected from halogen, nitro, cyano, hydroxy, alkyl, alkenyl, perhaloalkyl, cycloalkyl, cycloalkenyl, heterocyclyl, aryl, heteroaryl, —O— alkyl, —O-perhaloalkyl, —N(alkyl)alkyl, —N(H)alkyl, —NH$_2$, —SO$_2$-alkyl, —SO$_2$— perhaloalkyl, —N(alkyl)C(=O)alkyl, —N(H)C(=O)alkyl, —C(=O)N(alkyl)alkyl, —C(=O)N(H)alkyl, —C(=O)N(H)cycloalkyl, —C(=O)NH$_2$, —SO$_2$N(alkyl)alkyl, —SO$_2$N(H)alkyl, —SO$_2$NH$_2$, —C(=O)OH, and —C(=O)O-alkyl;

when the 'heteroaryl' group is substituted, it is substituted with 1 to 3 substituents independently selected from halogen, cyano, hydroxy, alkyl, alkenyl, perhaloalkyl, cycloalkyl, cycloalkenyl, heterocyclyl, —O-alkyl, O-perhaloalkyl, —N(alkyl)alkyl, —N(H)alkyl, —NH$_2$, —SO$_2$-alkyl, —SO$_2$-perhaloalkyl, —N(alkyl)C(=O)alkyl, —N(H)C(=O)alkyl, —C(=O)N(alkyl)alkyl, —C(=O)N(H)alkyl, —C(=O)NH$_2$, —SO$_2$N(alkyl)alkyl, —SO$_2$N(H)alkyl, —SO$_2$NH$_2$, —C(=O)OH, and —C(=O)O-alkyl;

when the 'heterocyclyl' and 'heterocycle' is substituted, each of them is substituted either on a ring carbon atom or on a ring hetero atom, and when it is substituted on a ring carbon atom, it is substituted with 1 to 3 substituents independently selected from halogen, nitro, cyano, oxo (=O), alkyl, alkenyl, perhaloalkyl, cycloalkyl, cycloalkenyl, aryl, heteroaryl, heterocyclyl, —SO$_2$R$^{8a}$, —OR$^{8b}$, —C(=O)OR$^{8a}$, —OC(=O)R$^{8a}$, —C(=O)N(H)R$^8$, —C(=O)N(alkyl)R$^8$, —N(H)C(=O)R$^{8a}$, —N(H)R$^8$, and —N(alkyl)R$^8$; and when the heterocyclic group is substituted on a ring nitrogen, it is substituted with substituents independently selected from alkyl, alkenyl, hydroxyalkyl, cycloalkyl, cycloalkenyl, aryl, heteroaryl, —SO$_2$R$^{8a}$, —C(=O)R$^{8c}$, C(=O)OR$^{8a}$, —C(=O)N(H)R$^8$, and —C(=O)N(alkyl)R$^8$;

R$^8$ is selected from the group consisting of hydrogen, alkyl, alkenyl, cycloalkyl, cycloalkenyl, aryl, heteroaryl, and heterocyclyl;

R$^{8a}$ is selected from the group consisting of alkyl, alkenyl, perhaloalkyl, cycloalkyl, cycloalkenyl, aryl, heteroaryl, and heterocyclyl;

R$^{8b}$ is selected from the group consisting of hydrogen, alkyl, alkenyl, perhaloalkyl, cycloalkyl, cycloalkenyl, aryl, heteroaryl, and heterocyclyl; and R$^{8c}$ is selected from the group consisting of alkyl, hydroxyalkyl, alkenyl, perhaloalkyl, cycloalkyl, cycloalkenyl, aryl, heteroaryl, and heterocyclyl.

In second aspect the invention provides a pharmaceutical composition comprising the compound of formula (I) and a pharmaceutically acceptable carrier.

In third aspect the invention provides a method of treating or preventing a disorder responsive to the inhibition of PI3K activity in a mammal suffering therefrom, comprising administering to the mammal in need of such treatment a therapeutically effective amount of a compound of formula (I).

DETAILED DESCRIPTION OF THE INVENTION

In one aspect, the present invention provides a compound of formula (I), its tautomeric form, its stereoisomer, its pharmaceutically acceptable salt, its combination with suitable medicament, its pharmaceutical composition and its use as PI3K inhibitor

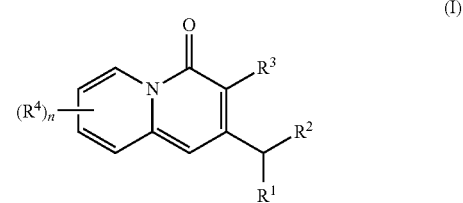

wherein,

R$^1$ is selected from a)

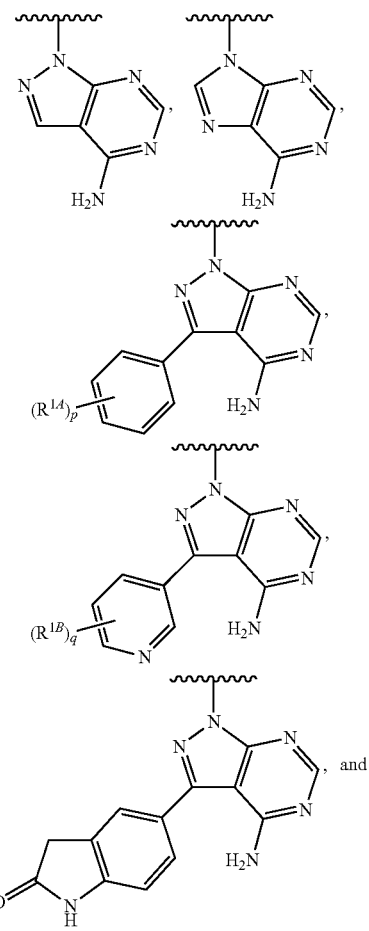

-continued

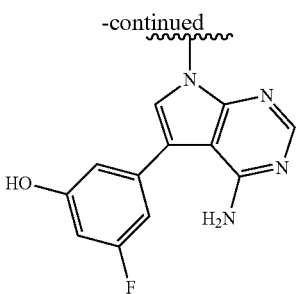

wherein,
R[1A] is independently selected at each occurrence from halogen, hydroxy, hydroxyalkyl, and —NHSO$_2$CH$_3$;
R[1B] is independently selected at each occurrence from hydroxy, alkoxy and —NHSO$_2$CH$_3$; or
b) —NH—R[1a]; wherein R[1a] is selected from

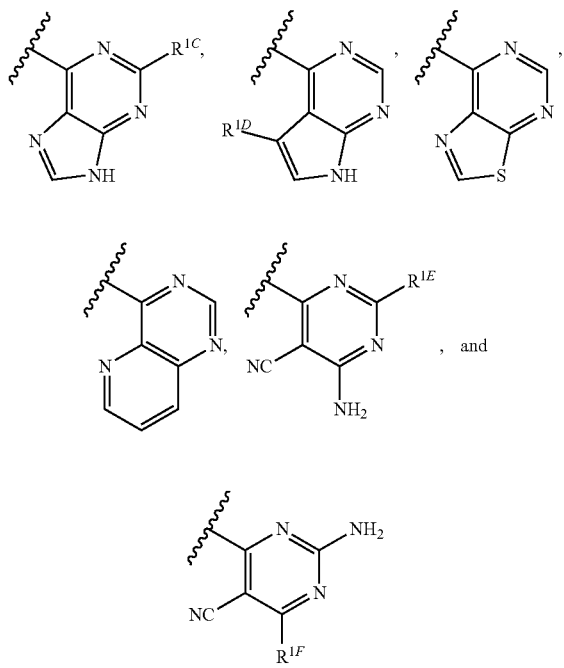

wherein,
R[1C] is selected from hydrogen, halogen, and amino; R[1D] is selected from halogen and cyano; R[1E] is selected from hydrogen and amino; R[1F] is selected from hydrogen, halogen, and alkyl;
R[2] is selected from hydrogen, substituted- or unsubstituted-alkyl, hydroxyalkyl, —OR[5], —(CH$_2$)$_m$NR[6]R[7], and C(═O)—NR[6]R[7];
R[3] is selected from substituted- or unsubstituted aryl, substituted- or unsubstituted cycloalkyl, and substituted- or unsubstituted cycloalkenyl;
R[4] is independently selected at each occurrence from halogen, substituted- or unsubstituted-alkyl, substituted- or unsubstituted-aryl, substituted- or unsubstituted-heteroaryl, substituted- or unsubstituted-heterocycle, substituted- or unsubstituted-carbocycle, and —OR[5];
R[5] is substituted- or unsubstituted-alkyl;
R[6] and R[7] are each independently selected from hydrogen and substituted- or unsubstituted-alkyl;

n is an integer selected from 0, 1, and 2;
m is an integer selected from 1, 2, 3, and 4;
p is an integer selected from 0, 1, and 2; and
q is an integer selected from 0, 1, and 2;
wherein:
when an 'alkyl' group is substituted, it is substituted with 1 to 3 substituents independently selected from oxo (═O), halogen, nitro, cyano, perhaloalkyl, cycloalkyl, cycloalkenyl, aryl, heteroaryl, heterocyclyl, —OR[8b], —SO$_2$R[8a], —C(═O)OR[8a], —OC(═O)R[8a], —C(═O)N(H)R[8], —C(═O)N(alkyl)R[8], —N(H)C(═O)R[8a], —N(H)R[8], and —N(alkyl)R[8];
when 'cycloalkyl', 'cycloalkenyl' and 'carbocycle' is substituted, each of them is substituted with 1 to 3 substituents independently selected from oxo (═O), halogen, nitro, cyano, alkyl, alkenyl, cycloalkyl, cycloalkenyl, perhaloalkyl, aryl, heteroaryl, heterocyclyl, —OR[8b], —SO$_2$R[8a], —C(═O)R[8a], —C(═O)OR[8a], —OC(═O)R[8a], —C(═O)N(H)R[8], —C(═O)N(alkyl)R[8], —N(H)C(═O)R[8a], —N(H)R[8], and —N(alkyl)R[8];
when the 'aryl' group is substituted, it is substituted with 1 to 3 substituents independently selected from halogen, nitro, cyano, hydroxy, alkyl, alkenyl, perhaloalkyl, cycloalkyl, cycloalkenyl, heterocyclyl, aryl, heteroaryl, —O— alkyl, —O-perhaloalkyl, —N(alkyl)alkyl, —N(H) alkyl, —NH$_2$, —SO$_2$-alkyl, —SO$_2$— perhaloalkyl, —N(alkyl)C(═O)alkyl, —N(H)C(═O)alkyl, —C(═O)N(alkyl)alkyl, —C(═O)N(H)alkyl, —C(═O)N(H)cycloalkyl, —C(═O)NH$_2$, —SO$_2$N(alkyl)alkyl, —SO$_2$N(H)alkyl, —SO$_2$NH$_2$, —C(═O)OH, and —C(═O)O-alkyl;
when the 'heteroaryl' group is substituted, it is substituted with 1 to 3 substituents independently selected from halogen, cyano, hydroxy, alkyl, alkenyl, perhaloalkyl, cycloalkyl, cycloalkenyl, heterocyclyl, —O-alkyl, O-perhaloalkyl, —N(alkyl)alkyl, —N(H)alkyl, —NH$_2$, —SO$_2$-alkyl, —SO$_2$-perhaloalkyl, —N(alkyl)C(═O)alkyl, —N(H)C(═O)alkyl, —C(═O)N(alkyl)alkyl, —C(═O)N(H)alkyl, —C(═O)NH$_2$, —SO$_2$N(alkyl)alkyl, —SO$_2$N(H)alkyl, —SO$_2$NH$_2$, —C(═O)OH, and —C(═O)O-alkyl;
when the 'heterocyclyl' and 'heterocycle' is substituted, each of them is substituted either on a ring carbon atom or on a ring hetero atom, and when it is substituted on a ring carbon atom, it is substituted with 1 to 3 substituents independently selected from halogen, nitro, cyano, oxo (═O), alkyl, alkenyl, perhaloalkyl, cycloalkyl, cycloalkenyl, aryl, heteroaryl, heterocyclyl, —SO$_2$R[8a], —OR[8b], —C(═O)OR[8a], —OC(═O)R[8a], —C(═O)N(H)R[8], —C(═O)N(alkyl)R[8], —N(H)C(═O)R[8a], —N(H)R[8], and —N(alkyl)R[8]; and when the heterocyclic group is substituted on a ring nitrogen, it is substituted with substituents independently selected from alkyl, alkenyl, hydroxyalkyl, cycloalkyl, cycloalkenyl, aryl, heteroaryl, —SO$_2$R[8a], —C(═O)R[8c], C(═O)OR[8a], —C(═O)N(H)R[8], and —C(═O)N(alkyl)R[8];
R[8] is selected from the group consisting of hydrogen, alkyl, alkenyl, cycloalkyl, cycloalkenyl, aryl, heteroaryl, and heterocyclyl;
R[8a] is selected from the group consisting of alkyl, alkenyl, perhaloalkyl, cycloalkyl, cycloalkenyl, aryl, heteroaryl, and heterocyclyl;
R[8b] is selected from the group consisting of hydrogen, alkyl, alkenyl, perhaloalkyl, cycloalkyl, cycloalkenyl, aryl, heteroaryl, and heterocyclyl; and $R^{8c}$ is selected from the group consisting of alkyl, hydroxyalkyl, alkenyl, perhaloalkyl, cycloalkyl, cycloalkenyl, aryl, heteroaryl, and heterocyclyl.

In particular embodiments, $R^1$ is selected from a)

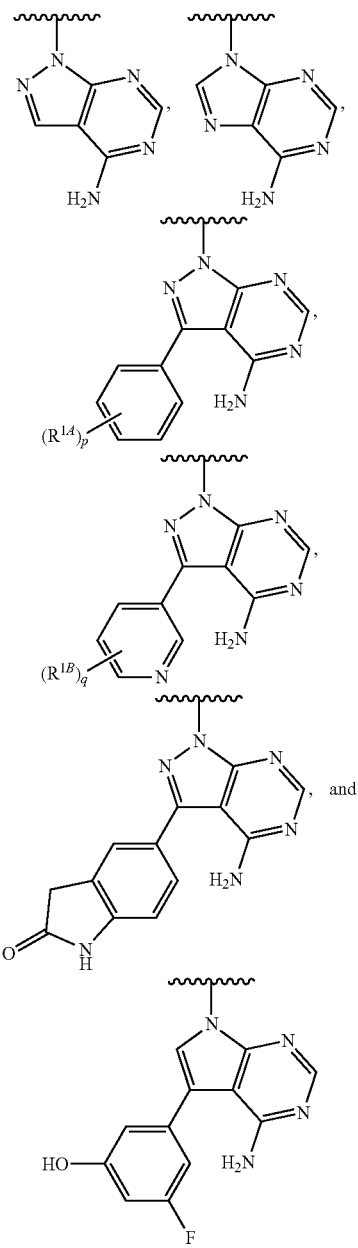

wherein,
$R^{1A}$ is independently selected at each occurrence from halogen, hydroxy, hydroxyalkyl, and —NHSO$_2$CH$_3$;
$R^{1B}$ is independently selected at each occurrence from hydroxy, alkoxy and —NHSO$_2$CH$_3$; or b) —NH—$R^{1a}$; wherein $R^{1a}$ is selected from

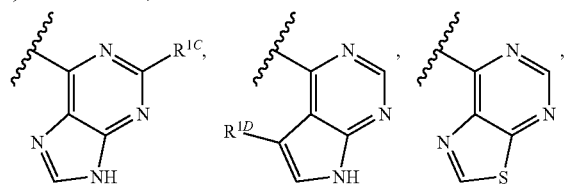

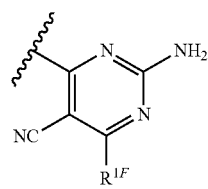

wherein,
$R^{1C}$ is selected from hydrogen, halogen, and amino; $R^{1D}$ is selected from halogen and cyano; $R^{1E}$ is selected from hydrogen and amino; $R^{1F}$ is selected from hydrogen, halogen, and alkyl.

More particularly, $R^1$ is selected from a)

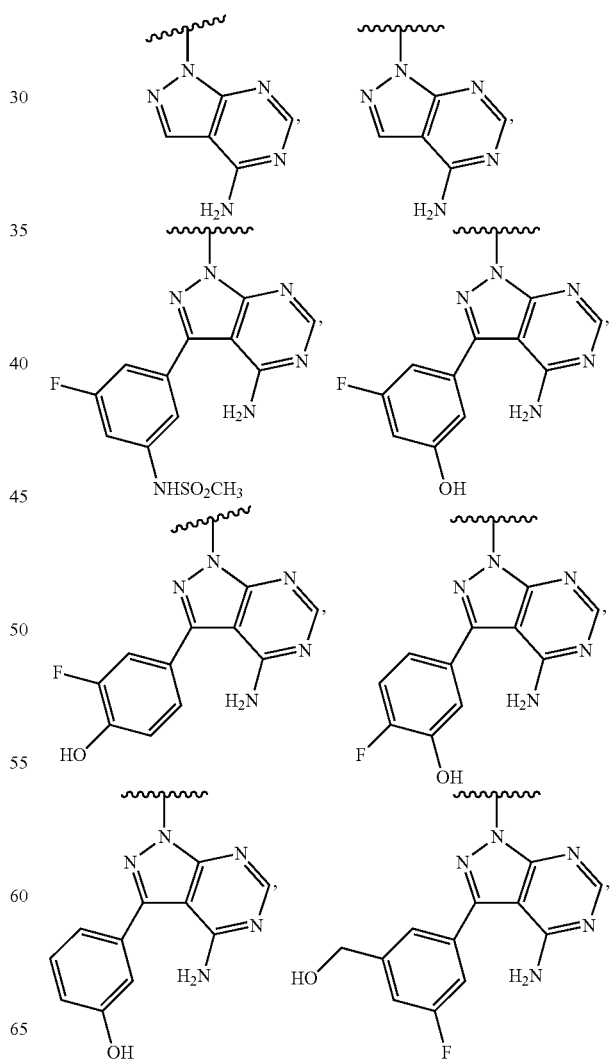

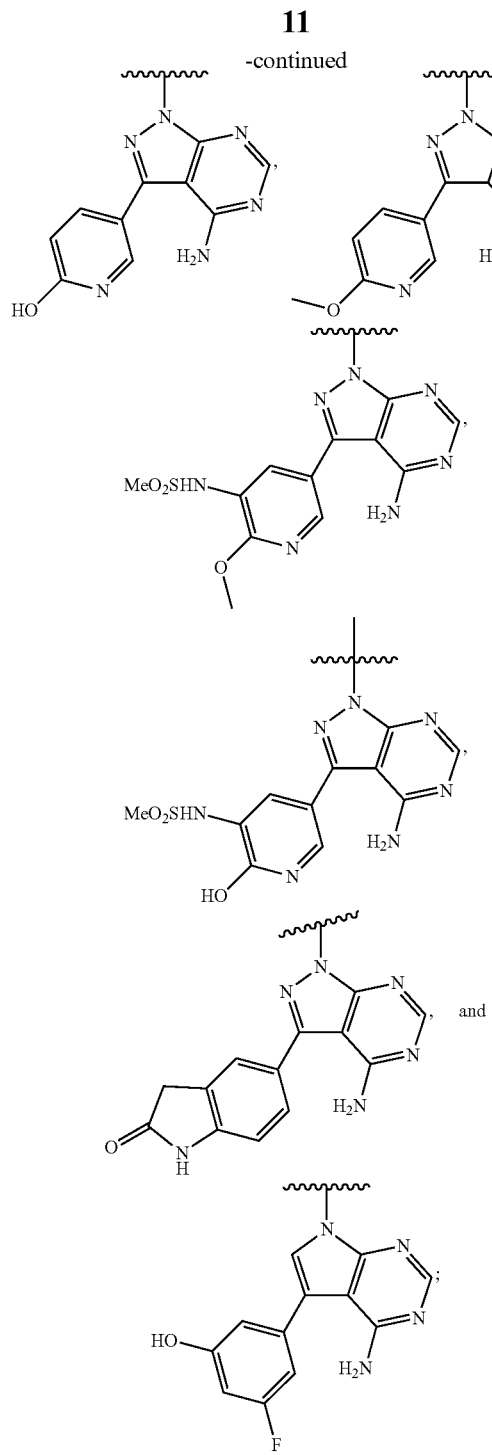

or a) —NH—R[1a]; wherein R[1a] is selected from

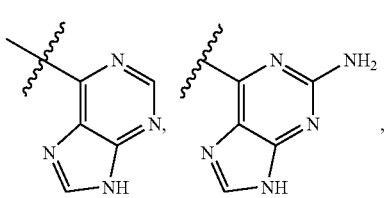

In particular embodiments, R[2] is selected from hydrogen and alkyl. More particularly, R[2] is selected from hydrogen, methyl and ethyl.

In particular embodiments, R[3] is substituted- or unsubstituted aryl.

More particularly, R[3] is selected from phenyl, 3-fluorophenyl, 4-fluorophenyl, 3,5-difluorophenyl, 3,4-difluorophenyl, 3-fluoro-5-methylphenyl, 3-methylphenyl and 3-trifluoromethoxyphenyl.

In particular embodiments, R[4] is independently selected at each occurrence from halogen and alkyl.

More particularly, R[4] is independently selected at each occurrence from fluoro and methyl.

In particular embodiments, n is an integer selected from 0 to 2.

In particular embodiments, p is an integer selected from 1 and 2.

In particular embodiments, q is an integer selected from 1 and 2.

In particular embodiments, R[1] is selected from a)

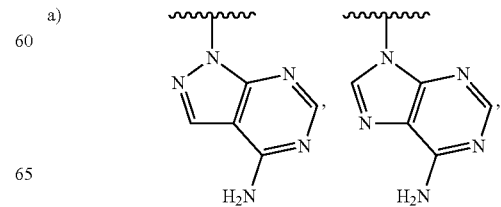

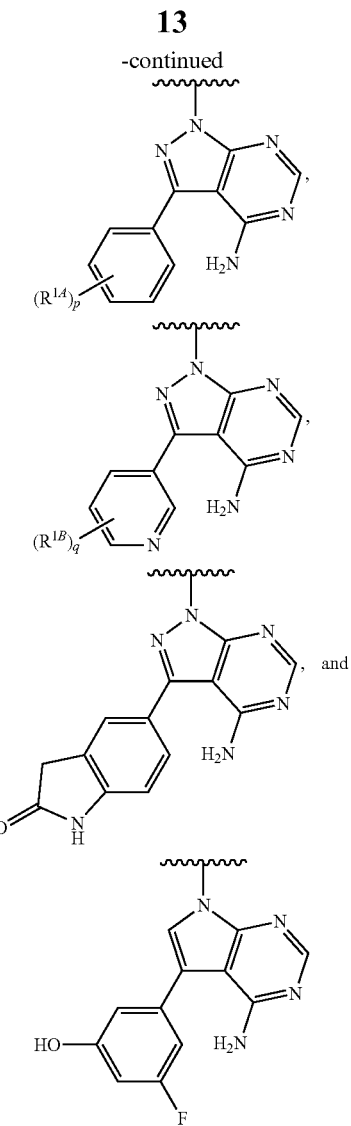

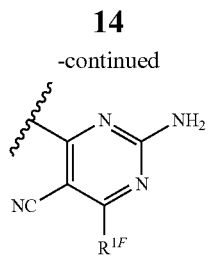

wherein, $R^{1C}$ is selected from hydrogen, halogen, and amino; $R^{1D}$ is selected from halogen and cyano; $R^{1E}$ is selected from hydrogen and amino; $R^{1F}$ is selected from hydrogen, halogen, and alkyl; $R^2$ is selected from hydrogen and alkyl; $R^3$ is substituted- or unsubstituted aryl; $R^4$ is independently selected at each occurrence from halogen and alkyl; n is an integer selected from 0 to 2; p is an integer selected from 1 and 2; and q is an integer selected from 1 and 2.

More particularly, $R^1$ is selected from b)

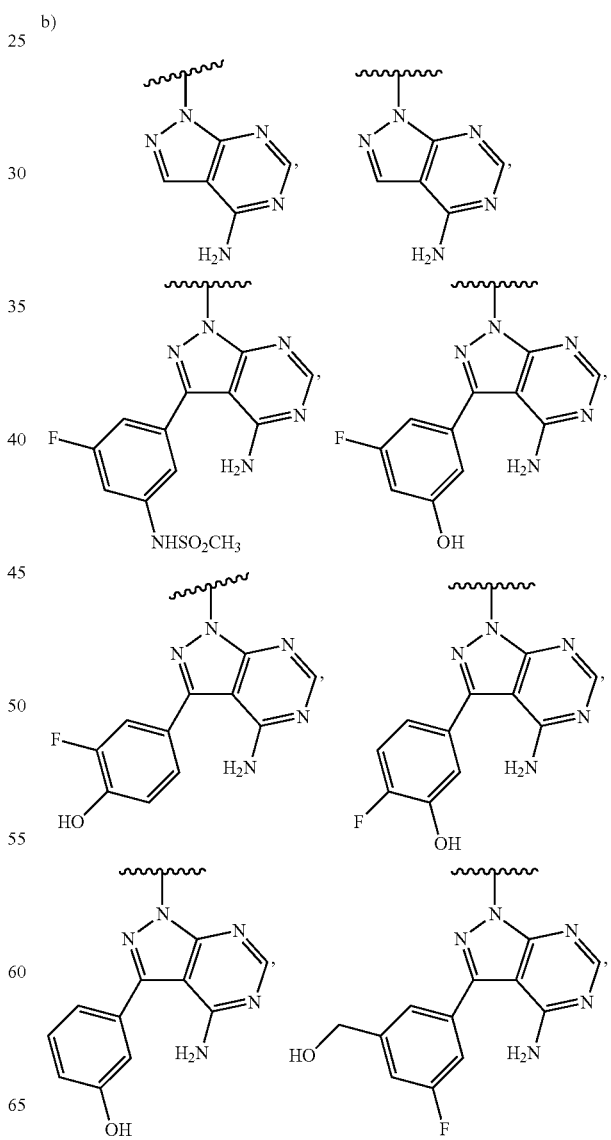

wherein, $R^{1A}$ is independently selected at each occurrence from halogen, hydroxy, hydroxyalkyl, and —NHSO$_2$CH$_3$;

$R^{1B}$ is independently selected at each occurrence from hydroxy, alkoxy and —NHSO$_2$CH$_3$; or b) —NH—$R^{1a}$; wherein $R^{1a}$ is selected from

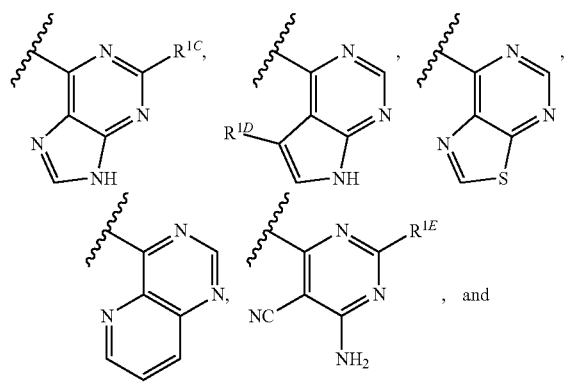

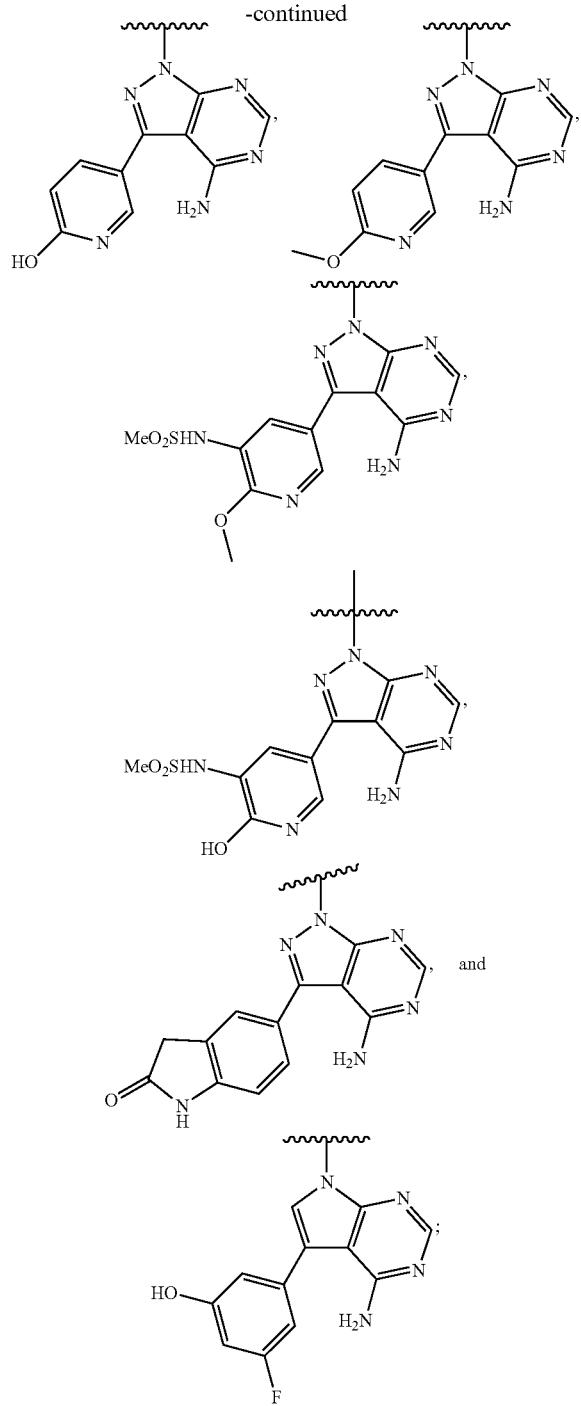

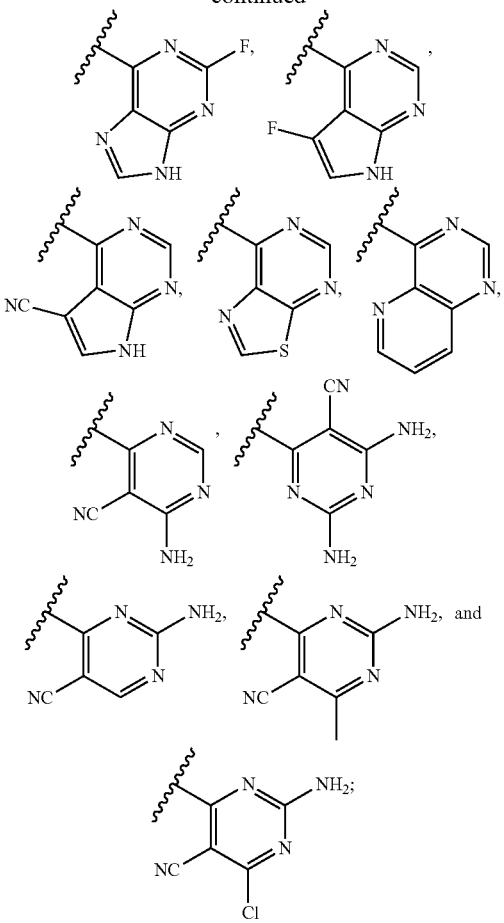

or b) —NH—R$^{1a}$; wherein R$^{1a}$ is selected from

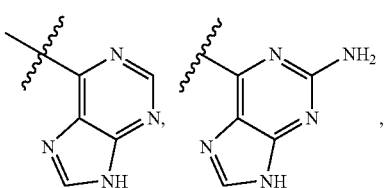

R$^2$ is selected from hydrogen, methyl and ethyl; R$^3$ is selected from phenyl, 3-fluorophenyl, 4-fluorophenyl, 3,5-difluorophenyl, 3,4-difluorophenyl, 3-fluoro-5-methylphenyl, 3-methylphenyl and 3-trifluoromethoxyphenyl; R$^4$ is independently selected at each occurrence from fluoro and methyl; n is an integer selected from 0 to 2; p is an integer selected from 1 and 2; and q is an integer selected from 1 and 2.

The term 'alkyl', as used herein, means a straight chain or branched hydrocarbon containing from 1 to 20 carbon atoms. Preferably the alkyl chain may contain 1 to 10 carbon atoms. More preferably alkyl chain may contain up to 6 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term 'alkenyl', as used herein, means an alkyl group containing at least one double bond.

The terms 'alkyl', and 'alkenyl' as defined hereinabove may be substituted with 1 to 3 substituents independently selected from oxo (=O), halogen, nitro, cyano, perhaloalkyl, cycloalkyl, cycloalkenyl, aryl, heteroaryl, heterocyclyl, —OR$^{8b}$, —SO$_2$R$^{8a}$, —C(=O)OR$^{8a}$, —OC(=O)R$^{8a}$, —C(=O)N(H)R$^8$, —C(=O)N(alkyl)R$^8$, —N(H)C(=O)R$^{8a}$, —N(H)R$^8$, and —N(alkyl)R$^8$; R$^8$ is selected from the group consisting of hydrogen, alkyl, alkenyl, cycloalkyl, cycloalkenyl, aryl, heteroaryl, and heterocyclyl; R$^{8a}$ is selected from the group consisting of alkyl, alkenyl, perhaloalkyl, cycloalkyl, cycloalkenyl, aryl, heteroaryl, heterocyclyl; and $R^{8b}$ is selected from the group consisting of hydrogen, alkyl, alkenyl, perhaloalkyl, cycloalkyl, cycloalkenyl, aryl, heteroaryl, and heterocyclyl.

The term 'perhaloalkyl', as used herein, means an alkyl group as defined hereinabove wherein all the hydrogen atoms of the said alkyl group are substituted with halogen. The perhaloalkyl group is exemplified by trifluoromethyl, pentafluoroethyl, and the like.

The term 'amino', as used herein, means —$NH_2$.

The term 'cycloalkyl' as used herein, means a monocyclic, bicyclic, or tricyclic non-aromatic ring system containing from 3 to 14 carbon atoms, preferably monocyclic cycloalkyl ring containing 3 to 6 carbon atoms. Examples of monocyclic ring systems include cyclopropyl, cyclobutyl, cyclopentyl, cyclohexyl, cycloheptyl, and cyclooctyl. Bicyclic ring systems include monocyclic ring system fused across a bond with another cyclic system which may be an alicyclic ring or an aromatic ring. Bicyclic rings also include spirocyclic systems wherein the second ring gets annulated on a single carbon atom. Bicyclic ring systems are also exemplified by a bridged monocyclic ring system in which two non-adjacent carbon atoms of the monocyclic ring are linked by an alkylene bridge. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane, bicyclo[3.3.2]decane, bicyclo[3.1.0]hexane, bicyclo[4.1.0]heptane, bicyclo[3.2.0]heptanes, octahydro-1H-indene, spiro[2.5]octane, spiro[4.5]decane, spiro[bicyclo[4.1.0]heptane-2, 1'-cyclopentane], hexahydro-2'H-spiro[cyclopropane-1,1'-pentalene]. Tricyclic ring systems are the systems wherein the bicyclic systems as described above are further annulated with third ring, which may be an alicyclic ring or aromatic ring. Tricyclic ring systems are also exemplified by a bicyclic ring system in which two non-adjacent carbon atoms of the bicyclic ring are linked by a bond or an alkylene bridge. Representative examples of tricyclic-ring systems include, but are not limited to, tricyclo[$3.3.1.0^{3,7}$] nonane, and tricyclo[$3.3.1.1^{3,7}$]decane (adamantane).

The term 'cycloalkenyl', as used herein, means a cycloalkyl group containing at least one double bond.

The term 'carbocycle', as used herein, means a cyclic system made up of carbon atoms, which includes cycloalkyl, cycloalkenyl and aryl.

The 'cycloalkyl', 'cycloalkenyl' and 'carbocycle' as defined hereinabove may be substituted with 1 to 3 substituents independently selected from oxo (═O), halogen, nitro, cyano, alkyl, alkenyl, cycloalkyl, cycloalkenyl, perhaloalkyl, aryl, heteroaryl, heterocyclyl, —$OR^{8b}$, —$SO_2R^{8a}$, —C(═O)$R^{8a}$, —C(═O)O$R^{8a}$, —OC(═O)$R^{8a}$, —C(═O)N(H)$R^8$, —C(═O)N(alkyl)$R^8$, —N(H)C(═O)$R^{8a}$, —N(H)$R^8$, and —N(alkyl)$R^8$; $R^8$ is selected from the group consisting of hydrogen, alkyl, alkenyl, cycloalkyl, cycloalkenyl, aryl, heteroaryl, and heterocyclyl; $R^{8a}$ is selected from the group consisting of alkyl, alkenyl, perhaloalkyl, cycloalkyl, cycloalkenyl, aryl, heteroaryl, heterocyclyl; and $R^{8b}$ is selected from the group consisting of hydrogen, alkyl, alkenyl, perhaloalkyl, cycloalkyl, cycloalkenyl, aryl, heteroaryl, and heterocyclyl.

The term 'aryl', as used herein, refers to a monovalent monocyclic, bicyclic or tricyclic aromatic hydrocarbon ring system. Examples of aryl groups include phenyl, naphthyl, anthracenyl, fluorenyl, indenyl, azulenyl, and the like. Aryl group also include partially saturated bicyclic and tricyclic aromatic hydrocarbons, e.g., tetrahydro-naphthalene.

The 'aryl' as defined hereinabove may be substituted with 1 to 3 substituents selected from halogen, nitro, cyano, hydroxy, alkyl, alkenyl, perhaloalkyl, cycloalkyl, cycloalkenyl, heterocyclyl, aryl, heteroaryl, —O-alkyl, —O— perhaloalkyl, —N(alkyl)alkyl, —N(H)alkyl, —$NH_2$, —$SO_2$-alkyl, —$SO_2$-perhaloalkyl, —N(alkyl)C(═O)alkyl, —N(H)C(═O)alkyl, —C(═O)N(alkyl)alkyl, —C(═O)N(H)alkyl, —C(═O)N(H)cycloalkyl, —C(═O)$NH_2$, —$SO_2$N(alkyl)alkyl, —$SO_2$N(H)alkyl, —$SO_2NH_2$, —C(═O)OH, and —C(═O)O-alkyl.

The term 'heteroaryl', as used herein, refers to a 5-14 membered monocyclic, bicyclic, or tricyclic ring system having 1-4 ring heteroatoms selected from O, N, or S, and the remainder ring atoms being carbon (with appropriate hydrogen atoms unless otherwise indicated), wherein at least one ring in the ring system is aromatic. Heteroaryl groups may be optionally substituted with one or more substituents. In one embodiment, 0, 1, 2, 3, or 4 atoms of each ring of a heteroaryl group may be substituted by a substituent. Examples of heteroaryl groups include, but not limited to, pyridyl, 1-oxo-pyridyl, furanyl, thienyl, pyrrolyl, oxazolyl, oxadiazolyl, imidazolyl, thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, benzoxazolyl, benzofuranyl, indolizinyl, imidazopyridyl, tetrazolyl, benzimidazolyl, benzothiazolyl, benzothiadiazolyl, benzoxadiazolyl, indolyl, azaindolyl, imidazopyridyl, quinazolinyl, purinyl, pyrrolo[2, 3]pyrimidinyl, pyrazolo[3,4]pyrimidinyl, and benzo(b)thienyl, 2,3-thiadiazolyl, 1H-pyrazolo[5,1-c]-1,2,4-triazolyl, pyrrolo[3,4-d]-1,2,3-triazolyl, cyclopentatriazolyl, 3H-pyrrolo[3,4-c]isoxazolyl, 2,3-dihydro-benzo[1,4] dioxin-6-yl, 2,3-dihydro-benzo[1,4]dioxin-5-yl, 2,3-dihydro-benzofuran-5-yl, 2,3-dihydro-benzofuran-4-yl, 2,3-dihydro-benzofuran-6-yl, 2,3-dihydro-benzofuran-6-yl, 2,3-dihydro-1H-indol-5-yl, 2,3-dihydro-1H-indol-4-yl, 2,3-dihydro-1H-indol-6-yl, 2,3-dihydro-1H-indol-7-yl, benzo[1, 3]dioxol-4-yl, benzo[1,3]dioxol-5-yl, 1,2,3,4-tetrahydroquinolinyl, 1,2,3,4-tetrahydroisoquinolinyl, 2,3-dihydrobenzothien-4-yl, 2-oxoindolin-5-yl and the like.

The term 'heteroaryl' as defined hereinabove may be optionally substituted with 1 to 4 substituents selected from halogen, nitro, cyano, hydroxy, alkyl, alkenyl, perhaloalkyl, cycloalkyl, cycloalkenyl, heterocyclyl, —O-alkyl, O-perhaloalkyl, —N(alkyl)alkyl, —N(H)alkyl, —$NH_2$, —$SO_2$-alkyl, —$SO_2$-perhaloalkyl, —N(alkyl)C(═O)alkyl, —N(H)C(═O)alkyl, —C(═O)N(alkyl)alkyl, —C(═O)N(H)alkyl, —C(═O)$NH_2$, —$SO_2$N(alkyl)alkyl, —$SO_2$N(H)alkyl, —$SO_2NH_2$, —C(═O)OH, and —C(═O)O-alkyl.

The term 'heterocycle' or 'heterocyclic' as used herein, means a 'cycloalkyl' group wherein one or more of the carbon atoms replaced by heteroatom selected from N, S and O. The heterocycle may be connected to the parent molecular moiety through any carbon atom or any nitrogen atom contained within the heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1.1-dioxidothiomorpholinyl (thiomorpholine sulfone), thiopyranyl, and trithianyl. Representative examples of bicyclic heterocycle include, but are not limited to, 1,2,3,4-tetrahydroisoquinolin-2-yl, 1,2,3,4-tetrahydroquinolin-1-yl, 1,3-benzodioxolyl, 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl, and 1,2,3,4-tetrahydroquinolinyl. The term heterocycle also includes bridged and spiro heterocyclic systems such as azabicyclo[3.2.1]octane, azabicyclo[3.3.1]nonane, 8-oxa-3-azabicyclo[3.2.1]octan-3-yl, 3-oxa-8-azabicyclo[3.2.1]octan-8-yl, 6-oxa-3-azabicyclo[3.1.1]heptan-3-yl, 8-azabicyclo[3.2.1]octan-8-yl, 3-azabicyclo[3.2.1]octan-3-yl, 3-azabicyclo[3.1.0]hexan-3-yl, 6-azaspiro[2.5]octan-6-yl, 5-azaspiro[2.5]octan-5-yl, 4-azaspiro[2.4]heptan-4-yl, and the like. The 'heterocycle' as defined hereinabove, wherein the ring carbon may be optionally substituted with 1 to 3 substituents selected from halogen, nitro, cyano, oxo (=O), alkyl, alkenyl, perhaloalkyl, cycloalkyl, cycloalkenyl, aryl, heteroaryl, heterocyclyl, —SO$_2$R$^{8a}$, —OR$^{8b}$, —C(=O)OR$^{8a}$, —OC(=O)R$^{8a}$, —C(=O)N(H)R$^8$, —C(=O)N(alkyl)R$^8$, —N(H)C(=O)R$^{8a}$, —N(H)R$^8$, and —N(alkyl)R$^8$; R$^8$ is selected from the group consisting of hydrogen, alkyl, alkenyl, cycloalkyl, cycloalkenyl, aryl, heteroaryl, and heterocyclyl; R$^{8a}$ is selected from the group consisting of alkyl, alkenyl, perhaloalkyl, cycloalkyl, cycloalkenyl, aryl, heteroaryl, heterocyclyl; and R$^{8b}$ is selected from the group consisting of hydrogen, alkyl, alkenyl, perhaloalkyl, cycloalkyl, cycloalkenyl, aryl, heteroaryl, and heterocyclyl.

The term 'heterocycle' as defined hereinabove, wherein the ring nitrogen may be optionally substituted with a substituent selected from alkyl, alkenyl, hydroxyalkyl, cycloalkyl, cycloalkenyl, aryl, heteroaryl, —SO$_2$R$^{8a}$, —C(=O)R$^{8c}$, C(=O)OR$^{8a}$, —C(=O)N(H)R$^8$, —C(=O)N(alkyl)R$^8$; R$^8$ is selected from the group consisting of hydrogen, alkyl, alkenyl, cycloalkyl, cycloalkenyl, aryl, heteroaryl, and heterocyclyl; R$^{8a}$ is selected from the group consisting of alkyl, alkenyl, perhaloalkyl, cycloalkyl, cycloalkenyl, aryl, heteroaryl, heterocyclyl; R$^{8c}$ is selected from the group consisting of alkyl, hydroxylalkyl, alkenyl, perhaloalkyl, cycloalkyl, cycloalkenyl, aryl, heteroaryl, heterocyclyl.

The term 'oxo' means a divalent oxygen (=O) attached to the parent group. For example oxo attached to carbon forms a carbonyl, oxo substituted on cyclohexane forms a cyclohexanone, and the like.

The term 'annulated' means the ring system under consideration is either annulated with another ring at a carbon atom of the cyclic system or across a bond of the cyclic system as in the case of fused or spiro ring systems.

The term 'bridged' means the ring system under consideration contain an alkylene bridge having 1 to 4 methylene units joining two non-adjacent ring atoms.

Whenever a range of the number of atoms in a structure is indicated (e.g., a $C_1$ to $C_{20}$ alkyl, $C_2$ to $C_{20}$ alkenyl etc.), it is specifically contemplated that any sub-range or individual number of carbon atoms falling within the indicated range also can be used. Thus, for instance, the recitation of a range of 1-6 carbon atoms (e.g., $C_1$ to $C_6$), 2-6 carbon atoms (e.g., $C_2$ to $C_6$), 3-6 carbon atoms (e.g., $C_3$ to $C_6$), as used with respect to any chemical group (e.g., alkyl, alkenyl, etc.) referenced herein encompasses and specifically describes 1, 2, 3,4, 5, and/or 6 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 2-3 carbon atoms, 2-4 carbon atoms, 2-5 carbon atoms, 2-6 carbon atoms, 3-4 carbon atoms, 3-5 carbon atoms, 3-6 carbon atoms, 4-5 carbon atoms, 4-6 carbon atoms as appropriate).

In accordance with an embodiment, the invention provides a compound, its stereoisomers, racemates, and pharmaceutically acceptable salt thereof as described hereinabove wherein the compound of general formula (I) is selected from:

2-(1-((9H-purin-6-yl)amino)ethyl)-3-phenyl-4H-quinolizin-4-one;
2-(1-((9H-purin-6-yl)amino)ethyl)-6-methyl-3-phenyl-4H-quinolizin-4-one;
2-(1-((9H-purin-6-yl)amino)ethyl)-7-methyl-3-phenyl-4H-quinolizin-4-one;
4-Amino-6-((1-(4-oxo-3-phenyl-4H-quinolizin-2-yl)ethyl)amino)pyrimidine-5-carbonitrile;
2-(1-((9H-purin-6-yl)amino)ethyl)-3-(3-fluorophenyl)-4H-quinolizin-4-one;
4-Amino-6-((1-(3-(3-fluorophenyl)-4-oxo-4H-quinolizin-2-yl)ethyl)amino)-pyrimidine-5-carbonitrile;
4-Amino-6-((1-(6-methyl-4-oxo-3-phenyl-4H-quinolizin-2-yl)ethyl)amino)-pyrimidine-5-carbonitrile;
2-(1-((2-Amino-9H-purin-6-yl)amino)ethyl)-6-methyl-3-phenyl-4H-quinolizin-4-one;
2-(1-((2-Fluoro-9H-purin-6-yl)amino)ethyl)-6-methyl-3-phenyl-4H-quinolizin-4-one;
4-Amino-6-((1-(3-(3-fluorophenyl)-6-methyl-4-oxo-4H-quinolizin-2-yl)ethyl)amino)pyrimidine-5-carbonitrile;
2-(1-((9H-purin-6-yl)amino)ethyl)-3-(3-fluorophenyl)-6-methyl-4H-quinolizin-4-one;
2-(1-((2-Amino-9H-purin-6-yl)amino)ethyl)-3-(3-fluorophenyl)-6-methyl-4H-quinolizin-4-one;
2-(1-((9H-purin-6-yl)amino)ethyl)-7-fluoro-3-phenyl-4H-quinolizin-4-one;
4-Amino-6-((1-(7-fluoro-4-oxo-3-phenyl-4H-quinolizin-2-yl)ethyl)amino)-pyrimidine-5-carbonitrile;
2-(1-((2-Amino-9H-purin-6-yl)amino)ethyl)-7-fluoro-3-(3-fluorophenyl)-4H-quinolizin-4-one;
4-Amino-6-((1-(7-fluoro-3-(3-fluorophenyl)-4-oxo-4H-quinolizin-2-yl)ethyl)amino)pyrimidine-5-carbonitrile;
4-Amino-6-((1-(3-(3,5-difluorophenyl)-6-methyl-4-oxo-4H-quinolizin-2-yl)ethyl)amino)pyrimidine-5-carbonitrile;
2-(1-((2-amino-9H-purin-6-yl)amino)ethyl)-3-(3,5-difluorophenyl)-6-methyl-4H-quinolizin-4-one;
4-Amino-6-((1-(3-(3,4-difluorophenyl)-6-methyl-4-oxo-4H-quinolizin-2-yl)ethyl)amino)pyrimidine-5-carbonitrile;
2-Amino-4-((1-(7-fluoro-3-(3-fluorophenyl)-4-oxo-4H-quinolizin-2-yl)ethyl)amino)pyrimidine-5-carbonitrile;
2-Amino-4-((1-(7-fluoro-3-(3-fluorophenyl)-4-oxo-4H-quinolizin-2-yl)ethyl)amino)-6-methylpyrimidine-5-carbonitrile;
4-Amino-6-((1-(7-fluoro-6-methyl-4-oxo-3-phenyl-4H-quinolizin-2-yl)ethyl)amino)pyrimidine-5-carbonitrile;
4-Amino-6-((1-(7-fluoro-3-(3-fluorophenyl)-6-methyl-4-oxo-4H-quinolizin-2-yl)ethyl)amino)pyrimidine-5-carbonitrile;
2-(1-((9H-purin-6-yl)amino)ethyl)-7-fluoro-6-methyl-3-phenyl-4H-quinolizin-4-one;
(S)-2,4-diamino-6-((1-(7-fluoro-4-oxo-3-phenyl-4H-quinolizin-2-yl)ethyl)amino)-pyrimidine-5-carbonitrile;
(S)-2-amino-4-((1-(7-fluoro-4-oxo-3-phenyl-4H-quinolizin-2-yl)ethyl)amino)pyrimidine-5-carbonitrile;
(S)-2-amino-4-((1-(7-fluoro-4-oxo-3-phenyl-4H-quinolizin-2-yl)ethyl)amino)-6-methylpyrimidine-5-carbonitrile;
(S)-4-((1-(7-fluoro-4-oxo-3-phenyl-4H-quinolizin-2-yl)ethyl)amino)-7H-pyrrolo[2,3-d]pyrimidine-5-carbonitrile;
(S)-4-amino-6-((1-(7-fluoro-3-(3-fluoro-5-methylphenyl)-4-oxo-4H-quinolizin-2-yl)ethyl)amino)pyrimidine-5-carbonitrile;
(S)-2,4-diamino-6-((1-(7-fluoro-3-(3-fluoro-5-methylphenyl)-4-oxo-4H-quinolizin-2-yl)ethyl)amino)pyrimidine-5-carbonitrile;
(S)-4-amino-6-((1-(7-fluoro-4-oxo-3-(m-tolyl)-4H-quinolizin-2-yl)ethyl)amino)pyrimidine-5-carbonitrile;

(S)-2,4-diamino-6-((1-(7-fluoro-4-oxo-3-(m-tolyl)-4H-quinolizin-2-yl)ethyl)-amino)pyrimidine-5-carbonitrile;
(S)-2-(1-((2-amino-9H-purin-6-yl)amino)ethyl)-7-fluoro-3-phenyl-4H-quinolizin-4-one;
(S)-4-amino-6-((1-(7-fluoro-4-oxo-3-(3-(trifluoromethoxy)phenyl)-4H-quinolizin-2-yl)ethyl)amino)pyrimidine-5-carbonitrile;
(S)-2-(1-((2-amino-9H-purin-6-yl)amino)ethyl)-7-fluoro-3-(3-(trifluoromethoxy)-phenyl)-4H-quinolizin-4-one;
(S)-4-amino-6-((1-(7-fluoro-3-(4-fluorophenyl)-4-oxo-4H-quinolizin-2-yl)ethyl)amino)pyrimidine-5-carbonitrile;
(S)-2,4-diamino-6-((1-(7-fluoro-3-(4-fluorophenyl)-4-oxo-4H-quinolizin-2-yl)ethyl)amino)pyrimidine-5-carbonitrile;
(S)-2-(1-((9H-purin-6-yl)amino)ethyl)-7-fluoro-3-(4-fluorophenyl)-4H-quinolizin-4-one;
(S)-2-(1-((2-amino-9H-purin-6-yl)amino)ethyl)-7-fluoro-3-(4-fluorophenyl)-4H-quinolizin-4-one;
(S)-7-fluoro-2-(1-((5-fluoro-7H-pyrrolo[2,3-d]pyrimidin-4-yl)amino)ethyl)-3-phenyl-4H-quinolizin-4-one;
4-Amino-6-((1-(7-fluoro-4-oxo-3-phenyl-4H-quinolizin-2-yl)propyl)amino)pyrimidine-5-carbonitrile;
2,4-diamino-6-((1-(7-fluoro-4-oxo-3-phenyl-4H-quinolizin-2-yl)propyl)amino)pyrimidine-5-carbonitrile;
2-(1-((9H-purin-6-yl)amino)propyl)-7-fluoro-3-phenyl-4H-quinolizin-4-one;
4-Amino-6-((1-(7-fluoro-3-(3-fluorophenyl)-4-oxo-4H-quinolizin-2-yl)propyl)amino)pyrimidine-5-carbonitrile;
2,4-diamino-6-((1-(7-fluoro-3-(3-fluorophenyl)-4-oxo-4H-quinolizin-2-yl)propyl)amino)pyrimidine-5-carbonitrile;
2-(1-((9H-purin-6-yl)amino)propyl)-7-fluoro-3-(3-fluorophenyl)-4H-quinolizin-4-one;
2-(1-((2-amino-9H-purin-6-yl)amino)propyl)-7-fluoro-3-(3-fluorophenyl)-4H-quinolizin-4-one;
(S)-4-amino-6-((1-(3-(3,5-difluorophenyl)-7-fluoro-4-oxo-4H-quinolizin-2-yl)ethyl)amino)pyrimidine-5-carbonitrile;
(S)-2,4-diamino-6-((1-(3-(3,5-difluorophenyl)-7-fluoro-4-oxo-4H-quinolizin-2-yl)ethyl)amino)pyrimidine-5-carbonitrile;
(S)-2-(1-((9H-purin-6-yl)amino)ethyl)-3-(3,5-difluorophenyl)-7-fluoro-4H-quinolizin-4-one;
(S)-2-(1-((2-amino-9H-purin-6-yl)amino)ethyl)-3-(3,5-difluorophenyl)-7-fluoro-4H-quinolizin-4-one;
(S)-7-fluoro-3-phenyl-2-(1-(thiazolo[5,4-d]pyrimidin-7-ylamino)ethyl)-4H-quinolizin-4-one;
(S)-2-amino-4-chloro-6-((1-(7-fluoro-4-oxo-3-phenyl-4H-quinolizin-2-yl)ethyl)amino)pyrimidine-5-carbonitrile;
(S)-7-fluoro-3-phenyl-2-(1-(pyrido[3,2-d]pyrimidin-4-ylamino)ethyl)-4H-quinolizin-4-one;
2-((4-Amino-1H-pyrazolo[3,4-d]pyrimidin-1-yl)methyl)-6-methyl-3-phenyl-4H-quinolizin-4-one;
2-((6-Amino-9H-purin-9-yl)methyl)-3-phenyl-4H-quinolizin-4-one;
2-(1-(4-Amino-1H-pyrazolo[3,4-d]pyrimidin-1-yl)ethyl)-3-(3-fluorophenyl)-6-methyl-4H-quinolizin-4-one;
N-(3-(4-amino-1-(1-(7-fluoro-4-oxo-3-phenyl-4H-quinolizin-2-yl)ethyl)-1H-pyrazolo[3,4-d]pyrimidin-3-yl)-5-fluorophenyl)methanesulfonamide;
2-(1-(4-amino-3-(3-fluoro-5-hydroxyphenyl)-1H-pyrazolo[3,4-d]pyrimidin-1-yl)ethyl)-7-fluoro-3-phenyl-4H-quinolizin-4-one;
2-(1-(4-amino-3-(3-fluoro-4-hydroxyphenyl)-1H-pyrazolo[3,4-d]pyrimidin-1-yl)ethyl)-7-fluoro-3-phenyl-4H-quinolizin-4-one;
2-(1-(4-amino-3-(4-fluoro-3-hydroxyphenyl)-1H-pyrazolo[3,4-d]pyrimidin-1-yl)ethyl)-7-fluoro-3-phenyl-4H-quinolizin-4-one;
2-(1-(4-amino-3-(3-hydroxyphenyl)-1H-pyrazolo[3,4-d]pyrimidin-1-yl)ethyl)-7-fluoro-3-phenyl-4H-quinolizin-4-one;
2-(1-(4-amino-5-(3-fluoro-5-hydroxyphenyl)-7H-pyrrolo[2,3-d]pyrimidin-7-yl)ethyl)-7-fluoro-3-phenyl-4H-quinolizin-4-one;
2-(1-(4-amino-3-(6-methoxypyridin-3-yl)-1H-pyrazolo[3,4-d]pyrimidin-1-yl)ethyl)-7-fluoro-3-phenyl-4H-quinolizin-4-one;
2-(1-(4-amino-3-(2-oxoindolin-5-yl)-1H-pyrazolo[3,4-d]pyrimidin-1-yl)ethyl)-7-fluoro-3-phenyl-4H-quinolizin-4-one;
(S)-2-(1-(4-amino-3-(6-hydroxypyridin-3-yl)-1H-pyrazolo[3,4-d]pyrimidin-1-yl)ethyl)-7-fluoro-3-phenyl-4H-quinolizin-4-one;
N-(5-(4-amino-1-(1-(7-fluoro-4-oxo-3-phenyl-4H-quinolizin-2-yl)ethyl)-1H-pyrazolo[3,4-d]pyrimidin-3-yl)-2-methoxypyridin-3-yl)methanesulfonamide;
(S)—N-(5-(4-amino-1-(1-(7-fluoro-4-oxo-3-phenyl-4H-quinolizin-2-yl)ethyl)-1H-pyrazolo[3,4-d]pyrimidin-3-yl)-2-hydroxypyridin-3-yl)methanesulfonamide; and
2-(1-(4-amino-3-(3-fluoro-5-(hydroxymethyl)phenyl)-1H-pyrazolo[3,4-d]pyrimidin-1-yl)ethyl)-7-fluoro-3-phenyl-4H-quinolizin-4-one.

According to a feature of the present invention, the compound of general formula I where all the symbols are defined earlier, can be prepared by methods given in schemes 1, and 2 and the examples. Representative procedures are shown in, but not limited to, these schemes or examples.

The compounds of formula (I), wherein $R^1$ is —NH—$R^{1a}$ and $R^2$—$R^4$ are as defined herein above, can be prepared by the following procedure depicted in Scheme 1.

Scheme 1 wherein R1 is —NH—R1a

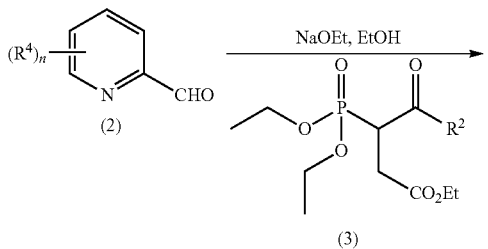

-continued

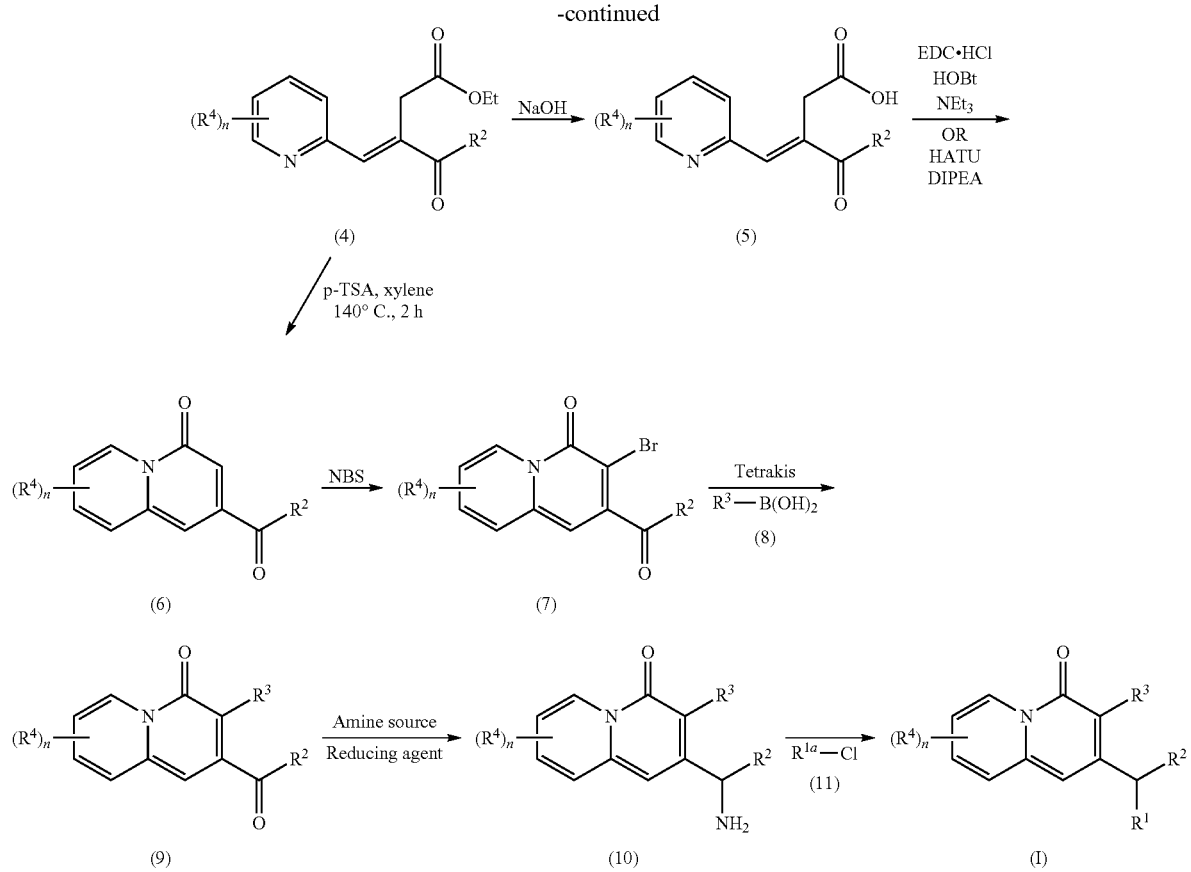

The pyridine carboxyaldehyde compound of formula (2) undergoes Wittig reaction with phosphate compound (3) to give compound of formula (4) which undergoes cyclization with suitable reagent such as p-TSA, PPA to give quinolizin-4-one compound of formula (6). The compound of formula (4) may also undergo hydrolysis with basic condition such as NaOH, KOH etc. to give compound (5). Cyclization of compound (5) with EDC.HCl/HOBt/NEt$_3$ or HATU/DIPEA gives the quinolizine-4-one compound (6). Bromination of quinolizin-4-one (6) with NBS gives compound (7) which undergoes Suzuki coupling with boronic acid (8) to give compound of formula (9). The compound (9) reacts with sulfinamide to form imine which undergoes reductive amination with NaBH$_4$ followed by hydrolysis with hydrochloric acid to give compound of formula (10). The compound (10) couples with the compound (11) to give compound of formula (I).

The compounds of formula (I), wherein $R^1$ is not —NH—$R^{1a}$ and $R^2$-$R^4$, are as defined herein above, can be prepared by the following procedure depicted in Scheme 2.

Scheme 2

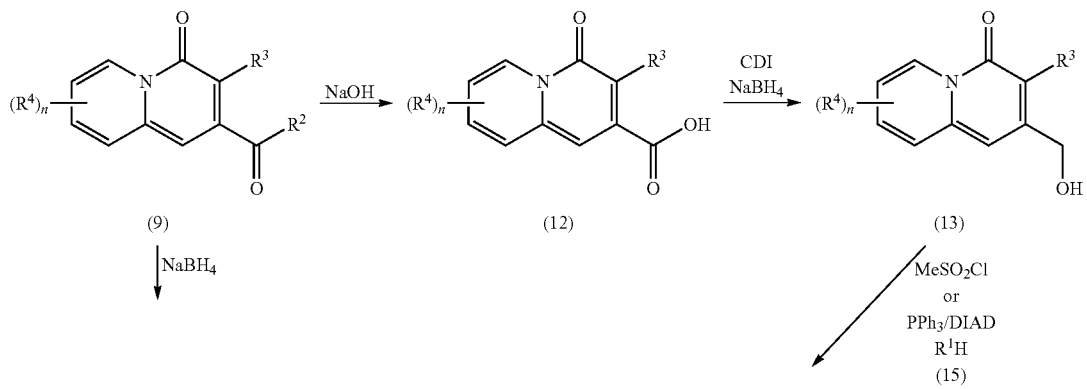

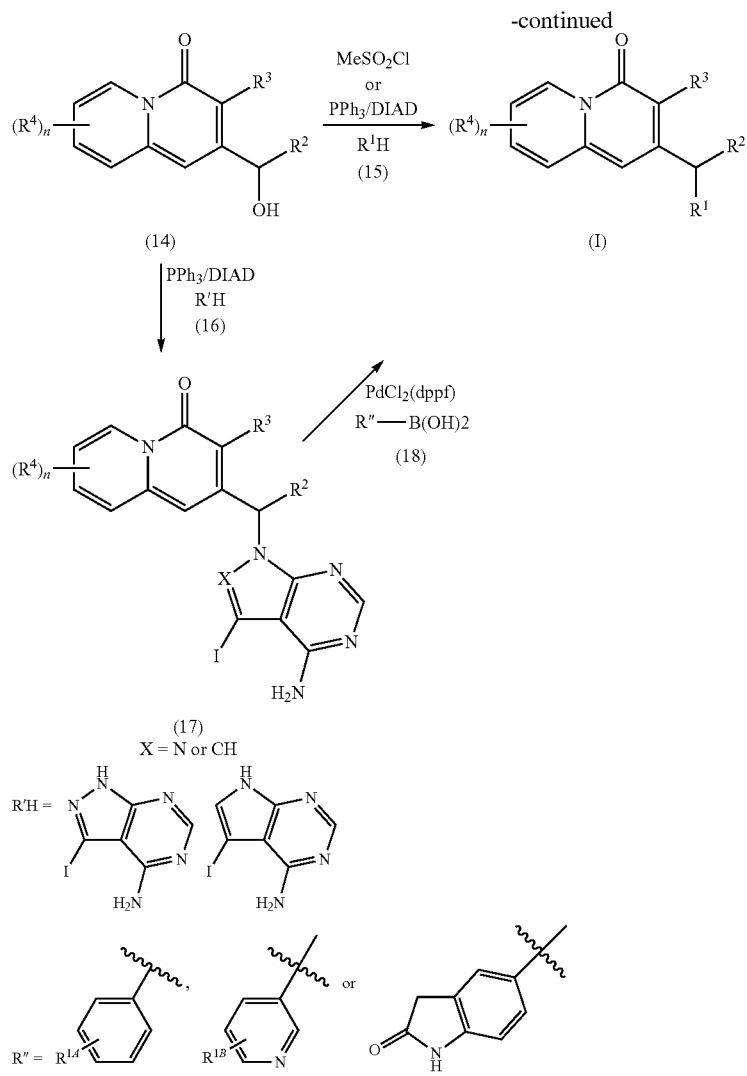

The compound of formula (9) undergoes hydrolysis with basic condition such as NaOH, KOH etc. to give compound (12). The compound of formula (12) reacts with CDI/NaBH$_4$ to form compound of formula (13). The compound of formula (9) undergoes reduction to form compound of formula (14). The compound of formula 13 or 14 reacts with methanesulfonyl chloride to form mesylate which couples with compound of formula (15) in heating condition to give the compound of formula (I). Alternatively, compound of formula 14 reacts with PPh$_3$/DIAD and compound (16) in heating condition to give the compound of formula (17) which undergoes Suzuki coupling with compound of formula (18) to give the compound of formula (I).

The intermediates and the compounds of the present invention can be obtained in a pure form in any manner known per se, for example, by distilling off the solvent in vacuum and/or re-crystallizing the residue obtained from a suitable solvent, such as pentane, diethyl ether, isopropyl ether, chloroform, dichloromethane, ethyl acetate, acetone or their combinations or subjecting it to one of the purification methods, such as column chromatography (e.g. flash chromatography) on a suitable support material such as alumina or silica gel using an eluent such as dichloromethane, ethyl acetate, hexane, methanol, acetone and their combinations. Preparative LC-MS method can also be used for the purification of molecules described herein.

Unless otherwise stated, work-up includes distribution of the reaction mixture between the organic and aqueous phase indicated within parentheses, separation of layers and drying the organic layer over sodium sulphate, filtration and evaporation of the solvent. Purification, unless otherwise mentioned, includes purification by silica gel chromatographic techniques, generally using a mobile phase with suitable polarity.

Salts of compound of formula I can be obtained by dissolving the compound in a suitable solvent, for example in a chlorinated hydrocarbon, such as methyl chloride or chloroform or a low molecular weight aliphatic alcohol, for example, ethanol or isopropanol, which was then treated with the desired acid or base as described in Berge S. M. et al., "Pharmaceutical Salts, a review article in Journal of Pharmaceutical sciences volume 66, page 1-19 (1977)" and in "*Handbook of Pharmaceutical Salts—Properties, Selection, and Use,*" by P. H. Einrich Stahland Camille G. wermuth, Wiley-VCH (2002). Lists of suitable salts can also be found in *Remington's Pharmaceutical Sciences,* 18th ed., Mack Publishing Company, Easton, Pa., 1990, p. 1445, and *Journal of Pharmaceutical Science,* 66, 2-19 (1977). For example, the salt can be of an alkali metal (e.g., sodium or potassium), alkaline earth metal (e.g., calcium), or ammonium.

The compounds of the invention or a composition thereof can potentially be administered as a pharmaceutically acceptable acid-addition, base neutralized or addition salt, formed by reaction with inorganic acids, such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base, such as sodium hydroxide, potassium hydroxide. The conversion to a salt is accomplished by treatment of the base compound with at least a stoichiometric amount of an appropriate acid. Typically, the free base is dissolved in an inert organic solvent such as diethyl ether, ethyl acetate, chloroform, ethanol, methanol, and the like, and the acid is added in a similar solvent. The mixture is maintained at a suitable temperature (e.g., between 0° C. and 50° C.). The resulting salt precipitates spontaneously or can be brought out of solution with a less polar solvent.

The stereoisomers of the compounds of formula I of the present invention may be prepared by stereospecific syntheses or resolution of racemic compound using an optically active amine, acid or complex forming agent, and separating the diastereomeric salt/complex by fractional crystallization or by column chromatography.

The compounds of formula I of the present invention can exist in tautomeric forms, such as keto-enol tautomers. Such tautomeric forms are contemplated as an aspect of the present invention and such tautomers may be in equilibrium or predominant in one of the forms.

Thus the present invention further provides a pharmaceutical composition comprising compounds of the general formula (I) as defined above, its tautomeric form, its stereoisomer, or its pharmaceutically acceptable salt, and a pharmaceutically acceptable carrier.

Thus the present invention further provides a pharmaceutical composition, containing the compounds of the general formula (I) as defined above, its tautomeric forms, its stereoisomers, and its pharmaceutically acceptable salts in combination with the usual pharmaceutically acceptable carriers, diluents, excipients, and the like.

The pharmaceutically acceptable carrier or excipient is preferably one that is chemically inert to the compound of the invention and one that has no detrimental side effects or toxicity under the conditions of use. Such pharmaceutically acceptable carriers or excipients include saline (e.g., 0.9% saline), Cremophor EL® (which is a derivative of castor oil and ethylene oxide available from Sigma Chemical Co., St. Louis, Mo.) (e.g., 5% Cremophor EL/5% ethanol/90% saline, 10% Cremophor EL/90% saline, or 50% Cremophor EL/50% ethanol), propylene glycol (e.g., 40% propylene glycol/10% ethanol/50% water), polyethylene glycol (e.g., 40% PEG 400/60% saline), and alcohol (e.g., 40% ethanol/60% water). A preferred pharmaceutical carrier is polyethylene glycol, such as PEG 400, and particularly a composition comprising 40% PEG 400 and 60% water or saline. The choice of carrier will be determined in part by the particular compound chosen, as well as by the particular method used to administer the composition. Accordingly, there is a wide variety of suitable formulations of the pharmaceutical composition of the present invention.

The following formulations for oral, aerosol, parenteral, subcutaneous, intravenous, intraarterial, intramuscular, intrathecal, intraperitoneal, rectal, and vaginal administration are merely exemplary and are in no way limiting.

The pharmaceutical compositions can be administered parenterally, e.g., intravenously, intraarterially, subcutaneously, intradermally, intrathecally, or intramuscularly. Thus, the invention provides compositions for parenteral administration that comprise a solution of the compound of the invention dissolved or suspended in an acceptable carrier suitable for parenteral administration, including aqueous and non-aqueous, isotonic sterile injection solutions.

Overall, the requirements for effective pharmaceutical carriers for parenteral compositions are well known to those of ordinary skill in the art. See *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Toissel, 4th ed., pages 622-630 (1986). Such compositions include solutions containing anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol (for example in topical applications), or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride, with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils useful in parenteral formulations include petroleum, animal, vegetable, and synthetic oils. Specific examples of oils useful in such formulations include peanut, soybean, sesame, cottonseed, corn, olive, petrolatum, and mineral oil. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl-β-aminopropionates, and 2-alkyl-imidazoline quaternary ammonium salts, and (e) mixtures thereof.

The parenteral formulations typically will contain from about 0.5% or less to about 25% or more by weight of a compound of the invention in solution. Preservatives and buffers can be used. In order to minimize or eliminate irritation at the site of injection, such compositions can contain one or more nonionic surfactants having a hydrophile-lipophile balance (HLB) of from about 12 to about 17. The quantity of surfactant in such formulations will typically range from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Topical formulations, including those that are useful for transdermal drug release, are well known to those of skill in the art and are suitable in the context of the present invention for application to skin.

Formulations suitable for oral administration can consist of (a) liquid solutions, such as an effective amount of a compound of the invention dissolved in diluents, such as water, saline, or orange juice; (b) capsules, sachets, tablets, lozenges, and troches, each containing a pre-determined amount of the compound of the invention, as solids or granules; (c) powders; (d) suspensions in an appropriate liquid; and (e) suitable emulsions. Liquid formulations can include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the compound ingredient in a flavor, usually sucrose and acacia or tragacanth, as well as pastilles comprising a compound of the invention in an inert base, such as gelatin and glycerin, or sucrose and acacia, emulsions, gels, and the like containing, in addition to the compound of the invention, such excipients as are known in the art.

A compound of the present invention, alone or in combination with other suitable components, can be made into aerosol formulations to be administered via inhalation. A compound or epimer of the invention is preferably supplied in finely divided form along with a surfactant and propellant. Typical percentages of the compounds of the invention can be about 0.01% to about 20% by weight, preferably about 1% to about 10% by weight. The surfactant must, of course, be nontoxic, and preferably soluble in the propellant. Representative of such surfactants are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides can be employed. The surfactant can constitute from about 0.1% to about 20% by weight of the composition, preferably from about 0.25% to about 5%. The balance of the composition is ordinarily propellant. A carrier can also be included as desired, e.g., lecithin, for intranasal delivery. These aerosol formulations can be placed into acceptable pressurized propellants, such as dichlorodifluoromethane, propane, nitrogen, and the like. They also can be formulated as pharmaceuticals for non-pressured preparations, such as in a nebulizer or an atomizer. Such spray formulations can be used to spray mucosa.

Additionally, the compounds of the invention can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the compound ingredient, such carriers as are known in the art to be appropriate.

The concentration of the compound in the pharmaceutical formulations can vary, e.g., from less than about 1% to about 10%, to as much as about 20% to about 50% or more by weight, and can be selected primarily by fluid volumes, and viscosities, in accordance with the particular mode of administration selected.

For example, a typical pharmaceutical composition for intravenous infusion could be made up to contain 250 ml of sterile Ringer's solution, and 100 mg of at least one compound of the invention. Actual methods for preparing parenterally administrable compounds of the invention will be known or apparent to those skilled in the art and are described in more detail in, for example, *Remington's Pharmaceutical Science* (17th ed., Mack Publishing Company, Easton, Pa., 1985).

It will be appreciated by one of ordinary skill in the art that, in addition to the afore described pharmaceutical compositions, the compound of the invention can be formulated as inclusion complexes, such as cyclodextrin inclusion complexes, or liposomes. Liposomes can serve to target a compound of the invention to a particular tissue, such as lymphoid tissue or cancerous hepatic cells. Liposomes can also be used to increase the half-life of a compound of the invention. Many methods are available for preparing liposomes, as described in, for example, Szoka et al., *Ann. Rev. Biophys. Bioeng.*, 9, 467 (1980) and U.S. Pat. Nos. 4,235,871, 4,501,728, 4,837,028, and 5,019,369.

The compounds of the invention can be administered in a dose sufficient to treat the disease, condition or disorder. Such doses are known in the art (see, for example, the *Physicians' Desk Reference* (2004)). The compounds can be administered using techniques such as those described in, for example, Wasserman et al., *Cancer*, 36, pp. 1258-1268 (1975) and *Physicians' Desk Reference*, 58th ed., Thomson P D R (2004).

Suitable doses and dosage regimens can be determined by conventional range-finding techniques known to those of ordinary skill in the art. Generally, treatment is initiated with smaller dosages that are less than the optimum dose of the compound of the present invention. Thereafter, the dosage is increased by small increments until the optimum effect under the circumstances is reached. The present method can involve the administration of about 0.1 µg to about 50 mg of at least one compound of the invention per kg body weight of the individual. For a 70 kg patient, dosages of from about 10 µg to about 200 mg of the compound of the invention would be more commonly used, depending on a patient's physiological response.

By way of example and not intending to limit the invention, the dose of the pharmaceutically active agent(s) described herein for methods of treating or preventing a disease or condition as described above can be about 0.001 to about 1 mg/kg body weight of the subject per day, for example, about 0.001 mg, 0.002 mg, 0.005 mg, 0.010 mg, 0.015 mg, 0.020 mg, 0.025 mg, 0.050 mg, 0.075 mg, 0.1 mg, 0.15 mg, 0.2 mg, 0.25 mg, 0.5 mg, 0.75 mg, or 1 mg/kg body weight per day. The dose of the pharmaceutically active agent(s) described herein for the described methods can be about 1 to about 1000 mg/kg body weight of the subject being treated per day, for example, about 1 mg, 2 mg, 5 mg, 10 mg, 15 mg, 0.020 mg, 25 mg, 50 mg, 75 mg, 100 mg, 150 mg, 200 mg, 250 mg, 500 mg, 750 mg, or 1000 mg/kg body weight per day.

Another aspect of the present invention is provision of a method of treatment or prevention of a disorder responsive to the inhibition of PI3K activity in a mammal suffering therefrom, comprising administering to the mammal in need of such treatment a therapeutically effective amount of a compound of formula I.

Another aspect of the present invention is provision of a method of treating or preventing a disorder responsive to the inhibition of PI3K activity in a mammal suffering therefrom, comprising administering to the mammal in need of such treatment a therapeutically effective amount of a compound of formula I, its tautomeric form, its stereoisomer, or its pharmaceutically acceptable salt.

A compound formula (I), its tautomeric form, its stereoisomer, or its pharmaceutically acceptable salt, for use in treating or preventing a disorder responsive to the inhibition of PI3K activity in a mammal suffering therefrom.

A compound formula (I), its tautomeric form, its stereoisomer, or its pharmaceutically acceptable salt, for use in treating or preventing a disorder responsive to the inhibition of PI3K activity in a mammal suffering therefrom, wherein said disorder is cancer, inflammatory disorders or an autoimmune disorders.

PI3K inhibitors reported herein can be used for the treatment of diseases and/or disorders that include but are not limited to cancer, inflammatory disorders or auto-immune disorders. PI3K inhibitors mentioned herein can be used as single agents and/or in combination with other chemotherapeutic agents.

Cancers that can be treated and/or prevented with PI3K inhibitors include but are not, limited to acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS-related (e.g. Lymphoma and Kaposi's Sarcoma) or viral-induced cancer. In some embodiments, said method relates to the treatment of a non-cancerous hyperproliferative disorder such as benign hyperplasia of the skin (e. g., psoriasis), restenosis, or prostate (e.g., benign prostatic hypertrophy (BPH)).

In some embodiments, the disclosure provides to a method of treating a hyperproliferative disorder in a subject that comprises administering to said subject a therapeutically effective amount of a compound, or a pharmaceutically acceptable form (e.g., pharmaceutically acceptable salts, hydrates, solvates, isomers, prodrugs, and isotopically labeled derivatives) thereof, or pharmaceutical compositions as provided herein. In some embodiments, said method relates to the treatment of cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS-related (e.g., Lymphoma and Kaposi's Sarcoma) or viral-induced cancer. In some embodiments, said method relates to the treatment of a non-cancerous hyperproliferative disorder such as benign hyperplasia of the skin (e. g., psoriasis), restenosis, or prostate (e. g., benign prostatic hypertrophy (BPH)).

Patients that can be treated with compounds, or a pharmaceutically acceptable form (e.g., pharmaceutically acceptable salts, hydrates, solvates, isomers, prodrugs, and isotopically labeled derivatives) thereof, or pharmaceutical compositions as provided herein, according to the methods as provided herein include, for example, but not limited to, patients that have been diagnosed as having psoriasis; restenosis; atherosclerosis; BPH; breast cancer such as a ductal carcinoma in duct tissue in a mammary gland, medullary carcinomas, colloid carcinomas, tubular carcinomas, and inflammatory breast cancer; ovarian cancer, including epithelial ovarian tumors such as adenocarcinoma in the ovary and an adenocarcinoma that has migrated from the ovary into the abdominal cavity; uterine cancer; cervical cancer such as adenocarcinoma in the cervix epithelial including squamous cell carcinoma and adenocarcinomas; prostate cancer, such as a prostate cancer selected from the following: an adenocarcinoma or an adenocarinoma that has migrated to the bone; pancreatic cancer such as epitheliod carcinoma in the pancreatic duct tissue and an adenocarcinoma in a pancreatic duct; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute myeloid leukemia (AML), acute lymphocytic leukemia, chronic lymphocytic leukemia, chronic myeloid leukemia, hairy cell leukemia, myelodysplasia, myeloproliferative disorders, NK cell leukemia (e.g., blastic plasmacytoid dendritic cell neoplasm), acute myelogenous leukemia (AML), chronic myelogenous leukemia (CML), mastocytosis, chronic lymphocytic leukemia (CLL), multiple myeloma (MM), and myelodysplasia syndrome (MDS); bone cancer; lung cancer such as non-small cell lung cancer (NSCLC), which is divided into squamous cell carcinomas, adenocarcinomas, and large cell undifferentiated carcinomas, and small cell lung cancer; skin cancer such as basal cell carcinoma, melanoma, squamous cell carcinoma and actinic keratosis, which is a skin condition that sometimes develops into squamous cell carcinoma; eye retinoblastoma; cutaneous or intraocular (eye) melanoma; primary liver cancer (cancer that begins in the liver); kidney cancer; thyroid cancer such as papillary, follicular, medullary and anaplastic; lymphoma such as diffuse large B-cell lymphoma, B-cell immunoblastic lymphoma, NK cell lymphoma (e.g., blastic plasmacytoid dendritic cell neoplasm), and small non-cleaved cell lymphoma; Kaposi's Sarcoma; viral-induced cancers including hepatitis B virus (HBV), hepatitis C virus (HCV), and hepatocellular carcinoma; human lymphotropic virus-type 1 (HTLV-1) and adult T-cell leukemia/lymphoma; and human papilloma virus (HPV) and cervical cancer; central nervous system cancers (CNS) such as primary brain tumor, which includes gliomas (astrocytoma, anaplastic astrocytoma, or glioblastoma multiforme), Oligodendroglioma, Ependymoma, Meningioma, Lymphoma, Schwannoma, and Medulloblastoma; peripheral nervous system (PNS) cancers such as acoustic neuromas and malignant peripheral nerve sheath tumor (MPNST) including neurofibromas and schwannomas, malignant fibrous cytoma, malignant fibrous histiocytoma, malignant meningioma, malignant mesothelioma, and malignant mixed Miillerian tumor; oral cavity and oropharyngeal cancer such as, hypopharyngeal cancer, laryngeal cancer, nasopharyngeal cancer, and oropharyngeal cancer; stomach cancer such as lymphomas, gastric stromal tumors, and carcinoid tumors;

testicular cancer such as germ cell tumors (GCTs), which include seminomas and nonseminomas, and gonadal stromal tumors, which include Leydig cell tumors and Sertoli cell tumors; thymus cancer such as to thymomas, thymic carcinomas, Hodgkin disease, non-Hodgkin lymphomas carcinoids or carcinoid tumors; rectal cancer; and colon cancer.

Exemplary inflammatory conditions include, but are not limited to, inflammation associated with acne, anemia (e.g., aplastic anemia, haemolytic autoimmune anaemia), asthma, arteritis (e.g., polyarteritis, temporal arteritis, periarteritis nodosa, Takayasu's arteritis), arthritis (e.g., crystalline arthritis, osteoarthritis, psoriatic arthritis, gout flare, gouty arthritis, reactive arthritis, rheumatoid arthritis and Reiter's arthritis), ankylosing spondylitis, amylosis, amyotrophic lateral sclerosis, autoimmune diseases, allergies or allergic reactions, atherosclerosis, bronchitis, bursitis, chronic prostatitis, conjunctivitis, Chagas disease, chronic obstructive pulmonary disease, cermatomyositis, diverticulitis, diabetes (e.g., type I diabetes mellitus, type 2 diabetes mellitus), a skin condition (e.g., psoriasis, eczema, burns, dermatitis, pruritus (itch)), endometriosis, Guillain-Barre syndrome, infection, ischaemic heart disease, Kawasaki disease, glomerulonephritis, gingivitis, hypersensitivity, headaches (e.g., migraine headaches, tension headaches), ileus (e.g., postoperative ileus and ileus during sepsis), idiopathic thrombocytopenic purpura, interstitial cystitis (painful bladder syndrome), gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), lupus, multiple sclerosis, morphea, myeasthenia gravis, myocardial ischemia, nephrotic syndrome, pemphigus vulgaris, pernicious aneaemia, peptic ulcers, polymyositis, primary biliary cirrhosis, neuroinflammation associated with brain disorders (e.g., Parkinson's disease, Huntington's disease, and Alzheimer's disease), prostatitis, chronic inflammation associated with cranial radiation injury, pelvic inflammatory disease, polymyalgia rheumatic, reperfusion injury, regional enteritis, rheumatic fever, systemic lupus erythematosus, scleroderma, scierodoma, sarcoidosis, spondyloarthopathies, Sjogren's syndrome, thyroiditis, transplantation rejection, tendonitis, trauma or injury (e.g., frostbite, chemical irritants, toxins, scarring, burns, physical injury), vasculitis, vitiligo and Wegener's granulomatosis. In certain embodiments, the inflammatory disorder is selected from arthritis (e.g., rheumatoid arthritis), inflammatory bowel disease, inflammatory bowel syndrome, asthma, psoriasis, endometriosis, interstitial cystitis and prostatistis. In certain embodiments, the inflammatory condition is an acute inflammatory condition (e.g., for example, inflammation resulting from infection). In certain embodiments, the inflammatory condition is a chronic inflammatory condition (e.g., conditions resulting from asthma, arthritis and inflammatory bowel disease). The compounds can also be useful in treating inflammation associated with trauma and non-inflammatory myalgia.

Immune disorders, such as auto-immune disorders, include, but are not limited to, arthritis (including rheumatoid arthritis, spondyloarthopathies, gouty arthritis, degenerative joint diseases such as osteoarthritis, systemic lupus erythematosus, Sjogren's syndrome, ankylosing spondylitis, undifferentiated spondylitis, Behcet's disease, haemolytic autoimmune anaemias, multiple sclerosis, amyotrophic lateral sclerosis, amylosis, acute painful shoulder, psoriatic, and juvenile arthritis), asthma, atherosclerosis, osteoporosis, bronchitis, tendonitis, bursitis, skin condition (e.g., psoriasis, eczema, burns, dermatitis, pruritus (itch)), enuresis, eosinophilic disease, gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g. Crohn's disease, ulcerative colitis, collagenous colitis, lymphocytic colitis, ischaemic colitis, diversion colitis, Behcet's syndrome, indeterminate colitis) and inflammatory bowel syndrome (IBS)), relapsing polychondritis (e.g., atrophic polychondritis and systemic polychondromalacia), and disorders ameliorated by a gastroprokinetic agent (e.g., ileus, postoperative ileus and ileus during sepsis; gastroesophageal reflux disease (GORD, or its synonym GERD); eosinophilic esophagitis, gastroparesis such as diabetic gastroparesis; food intolerances and food allergies and other functional bowel disorders, such as nonulcerative dyspepsia (NUD) and non-cardiac chest pain (NCCP, including costo-chondritis)). In certain embodiments, a method of treating inflammatory or autoimmune diseases is provided comprising administering to a subject (e.g., a mammal) a therapeutically effective amount of a compound, or a pharmaceutically acceptable form (e.g., pharmaceutically acceptable salts, hydrates, solvates, isomers, prodrugs, and isotopically labeled derivatives) thereof, or pharmaceutical compositions as provided herein.

Other aspect of the present invention is provision of a compound formula (I), its tautomeric form, its stereoisomer, or its pharmaceutically acceptable salt, for use in treating or preventing a disorder responsive to the inhibition of PI3Kγ and PI3Kδ activity in a mammal suffering therefrom.

Further aspect of the present invention is provision of a compound formula (I), its tautomeric form, its stereoisomer, or its pharmaceutically acceptable salt, for use in treating or preventing a disorder responsive to the inhibition of PI3Kγ and PI3Kδ activity in a mammal suffering therefrom, wherein said disorder is cancer, inflammatory disorders or auto-immune disorders.

Yet another aspect of the present invention is provision of a compound formula (I), its tautomeric form, its stereoisomer, or its pharmaceutically acceptable salt, for use in treating or preventing a disorder responsive to the inhibition of PI3Kδ activity in a mammal suffering therefrom.

Further aspect of the present invention is provision of a compound formula (I), its tautomeric form, its stereoisomer, or its pharmaceutically acceptable salt, for use in treating or preventing a disorder responsive to the inhibition of PI3Kδ activity in a mammal suffering therefrom, wherein said disorder is cancer, inflammatory disorders or auto-immune disorders.

The terms "treat," "prevent," "ameliorate," and "inhibit," as well as words stemming therefrom, as used herein, do not necessarily imply 100% or complete treatment, prevention, amelioration, or inhibition. Rather, there are varying degrees of treatment, prevention, amelioration, and inhibition of which one of ordinary skill in the art recognizes as having a potential benefit or therapeutic effect. In this respect, the disclosed methods can provide any amount of any level of treatment, prevention, amelioration, or inhibition of the disorder in a mammal. For example, a disorder, including symptoms or conditions thereof, may be reduced by, for example, 100%, 90%, 80%, 70%, 60%, 50%, 40%, 30%, 20%, or 10%. Furthermore, the treatment, prevention, amelioration, or inhibition provided by the inventive method can include treatment, prevention, amelioration, or inhibition of one or more conditions or symptoms of the disorder, e.g., cancer. Also, for purposes herein, "treatment," "prevention," "amelioration," or "inhibition" can encompass delaying the onset of the disorder, or a symptom or condition thereof.

The terms "effective amount" or "therapeutically effective amount," as used herein, refer to a sufficient amount of an agent or a compound being administered which will relieve to some extent one or more of the symptoms of the disease or condition being treated. In some embodiments, the result is a reduction and! or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. In some embodiments, an appropriate "effective" amount in any individual case is determined using techniques, such as a dose escalation study.

In accordance with the invention, the term subject includes an "animal" which in turn includes a mammal such as, without limitation, the order Rodentia, such as mice, and the order Lagomorpha, such as rabbits. In one aspect, the mammals are from the order Carnivora, including Felines (cats) and Canines (dogs). In another aspect, the mammals are from the order Artiodactyla, including Bovines (cows) and Swine (pigs) or of the order Perssodactyla, including Equines (horses). In a further aspect, the mammals are of the order Primates, Ceboids, or Simoids (monkeys) or of the order Anthropoids (humans and apes). In yet another aspect, the mammal is human.

The term "patient" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

Another aspect of the present invention is a pharmaceutical composition of compound of formula I in combination with at least one other known anticancer agent, or a pharmaceutically acceptable salt of said agent.

The following abbreviations are used in the text: DMSO-d$_6$: Hexadeuterodimethyl sulfoxide; DMF: N,N-dimethyl formamide, THF: Tetrahydrofuran, J: Coupling constant in units of Hz, HOBt: Hydroxybenzotriazole, pTsOH, p-TSA: p-Toluenesulfonic acid, NBS: N-Bromosuccinimide, MeOH: Methanol, EtOH: Ethanol, HCl: Hydrochloric acid, TEA: Triethyl amine, PPA: Polyphosphoric Acid, CDI: 1,1'-Carbonyldiimidazole, DIAD: Diisopropyl azodicarboxylate, HATU: 1-[Bis(dimethylamino)methylene]-1H-1,2,3-triazolo[4,5-b]pyridinium 3-oxid hexafluorophosphate, DIPEA: N,N-Diisopropylethylamine.

Following examples further illustrate a method of preparation of compounds embodied in formula I; however, the examples should not be constructed as limiting in any way the scope of the invention.

EXAMPLES

Example 1: Preparation of 2-(1-Aminoethyl)-3-phenyl-4H-quinolizin-4-one

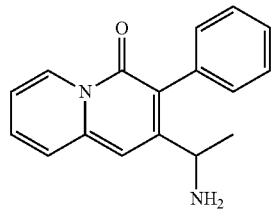 [SMILES: CC(N)c1cc2ccccn2c(=O)c1-c1ccccc1]

Step-1: ethyl 4-oxo-3-(pyridin-2-ylmethylene)pentanoate

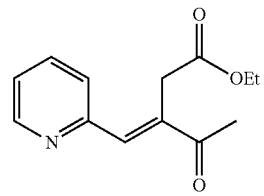 [SMILES: CCOC(=O)C/C(=C\c1ccccn1)C(C)=O]

To a stirred solution of ethyl 3-(diethoxyphosphoryl)-4-oxopentanoate (14.39 g, 51.3 mmol) and picolinaldehyde (5 g, 46.7 mmol) in ethanol was added sodium ethoxide (4.76 g, 70.0 mmol) at room temperature. The reaction mixture was stirred at room temperature for 2 h and then heated at 50° C. for 1 h. The solvent was removed under reduced pressure and the resultant residue was extracted with DCM (3×200 mL), the combined organic layer was washed with water (1×200 mL), dried over anhydrous Na$_2$SO$_4$, filtered and concentrated under reduced pressure to obtain crude product. The crude product was purified by Combiflash using 10% ethyl acetate-hexane as an eluent to yield ethyl 4-oxo-3-(pyridin-2-ylmethylene)pentanoate (7.4 g, 68.0% yield).

m/z 234.

Step-2: 2-acetyl-4H-quinolizin-4-one

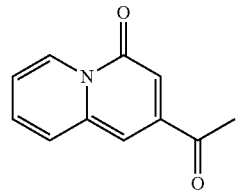

A stirred solution of ethyl 4-oxo-3-(pyridin-2-ylmethylene)pentanoate (1.7 g, 7.29 mmol) and pTsOH (0.139 g, 0.729 mmol) in xylene (75 mL) was heated at 140° C. for 2 h. The solvent was removed from the reaction mixture under reduced pressure, the resultant residue was then diluted with cold water and extracted with DCM (2×200 mL), the combined organic layer was washed with water (1×200 mL), dried over anhydrous $Na_2SO_4$, filtered and concentrated under reduced pressure to obtain crude product. The crude product was purified by Combiflash using 2% MeOH-DCM as an eluent to yield 2-acetyl-4H-quinolizin-4-one (1.205 g, 88% yield).

m/z 188.

Step-3: 2-acetyl-3-bromo-4H-quinolizin-4-one

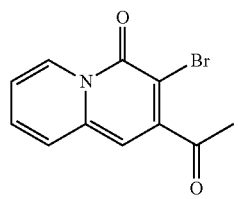

To a stirred solution of 2-acetyl-4H-quinolizin-4-one (1.5 g, 8.01 mmol) in $CCl_4$ (30 mL) was added NBS (1.426 g, 8.01 mmol) at room temperature and stirred for 45 minutes. The reaction mixture was diluted with water and extracted with DCM (2×100 mL), the combined organic layer was dried over anhydrous $Na_2SO_4$, filtered and concentrated under reduced pressure to obtain crude product. The crude product was purified by Combiflash using 25% ethyl acetate-hexane as an eluent to yield 2-acetyl-3-bromo-4H-quinolizin-4-one (1.52 g, 71.3% yield).

m/z 266, 268.

Step-4: 2-acetyl-3-phenyl-4H-quinolizin-4-one

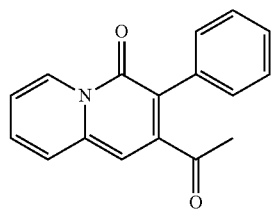 [SMILES: CC(=O)c1cc2ccccn2c(=O)c1-c1ccccc1]

To a stirred solution of 2-acetyl-3-bromo-4H-quinolizin-4-one (1.59 g, 5.98 mmol), phenylboronic acid (0.874 g, 7.17 mmol) and $Na_2CO_3$ (1.900 g, 17.93 mmol) in water:ethanol:toluene (30 mL, 1:2:2) was added Palladium tetrakis (0.345 g, 0.299 mmol) under nitrogen purging for 15 minutes. The reaction mixture was heated at 80° C. for 12 h. The solvent was evaporated from the reaction mixture and the residue was purified by Combiflash using 25% ethyl acetate-hexane as an eluent to yield 2-acetyl-3-phenyl-4H-quinolizin-4-one (1.45 g, 92% yield).

m/z 264.

Step-5: 2-(1-aminoethyl)-3-phenyl-4H-quinolizin-4-one

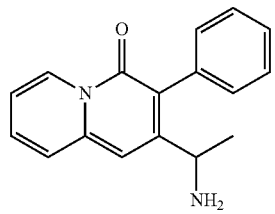 [SMILES: CC(N)c1cc2ccccn2c(=O)c1-c1ccccc1]

To a stirred solution of 2-acetyl-3-phenyl-4H-quinolizin-4-one (1.45 g, 5.51 mmol) in titanium isopropoxide (9.68 mL, 33.0 mmol) was added (S)-2-methylpropane-2-sulfinamide (0.667 g, 5.51 mmol) at 0° C. Then the reaction mixture was heated at 100° C. for 12-18 h. The reaction mixture was extracted with DCM and evaporated under reduced pressure to obtain crude residue. The crude residue was dissolve in MeOH and cooled to −78° C. then added $NaBH_4$ (0.833 g, 22.03 mmol) and stirred at −10° C. for 2 h. The reaction mixture was diluted with ethyl acetate and cold water. The organic layer was separated and concentrated under reduced pressure to yield crude compound which was then stirred in dioxane-HCl (4M, 10 mL) for 15 minutes. The reaction mixture was basified with sodium bicarbonate and extracted in ethyl acetate (3×200 mL), the combined organic layer was washed with water (1×200 mL), dried over anhydrous $Na_2SO_4$, filtered and concentrated under reduced pressure to obtain crude product which was purified by Combiflash using 4-6% MeOH-DCM as an eluent to yield 2-(1-aminoethyl)-3-phenyl-4H-quinolizin-4-one (402 mg, 27.6% yield).

m/z 265.

Example 2

The following intermediate compounds were prepared using the procedure described in Example 1 with appropriate changes to the reactants and reaction conditions.

2-(1-aminoethyl)-3-(3-fluorophenyl)-4H-quinolizin-4-one
m/z 283.

2-(1-Aminoethyl)-7-methyl-3-phenyl-4H-quinolizin-4-one
m/z 279.

2-(1-aminoethyl)-7-fluoro-3-(3-fluorophenyl)-4H-quinolizin-4-one
m/z 301.

2-(1-aminoethyl)-7-fluoro-3-(m-tolyl)-4H-quinolizin-4-one
m/z 297.

2-(1-aminoethyl)-7-fluoro-3-(3-fluoro-5-methylphenyl)-4H-quinolizin-4-one
m/z 315.

2-(1-aminoethyl)-7-fluoro-3-(3-(trifluoromethoxy)phenyl)-4H-quinolizin-4-one
m/z 367.

2-(1-aminoethyl)-7-fluoro-3-(4-fluorophenyl)-4H-quinolizin-4-one
m/z 301.

2-(1-aminoethyl)-3-(3,5-difluorophenyl)-7-fluoro-4H-quinolizin-4-one
m/z 319.

2-(1-aminopropyl)-7-fluoro-3-phenyl-4H-quinolizin-4-one
m/z 297.

2-(1-aminopropyl)-7-fluoro-3-(3-fluorophenyl)-4H-quinolizin-4-one
m/z 315.

2-(1-Aminoethyl)-7-fluoro-3-phenyl-4H-quinolizin-4-one
m/z 283.

Example 3: Preparation of (S)-2-(1-Aminoethyl)-7-fluoro-3-phenyl-4H-quinolizin-4-one

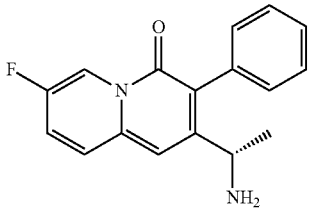 [SMILES: C[C@H](N)c1cc2ccc(F)cn2c(=O)c1-c1ccccc1]

Step-1: Ethyl 3-((5-fluoropyridin-2-yl)methylene)-4-oxopentanoate

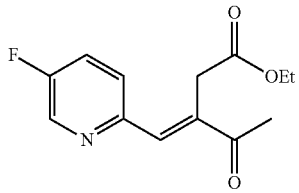 [SMILES: CCOC(=O)C/C(=C\c1ccc(F)cn1)C(C)=O]

To a stirred solution of ethyl 3-(diethoxyphosphoryl)-4-oxopentanoate (224 g, 799 mmol) and 5-fluoropicolinaldehyde (100 g, 799 mmol) in THF (250 mL) was added a solution of K₂CO₃ (122 g, 879 mmol) in water (250 mL) at room temperature and heated at 45° C. for 3-4 h. The reaction mixture was poured slowly into ice cold water (2000 mL) under sonication. The solid product precipitated was filtered and dried under vacuum to obtain Ethyl 3-((5-fluoropyridin-2-yl)methylene)-4-oxopentanoate (135 g, 67.2% yield).
m/z 252.

Step-2: 3-((5-fluoropyridin-2-yl)methylene)-4-oxopentanoic acid

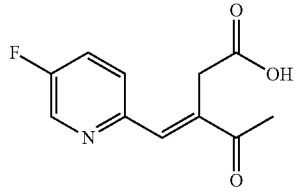 [SMILES: CC(=O)/C(=C/c1ccc(F)cn1)CC(=O)O]

To a stirred solution of ethyl 3-((5-fluoropyridin-2-yl) methylene)-4-oxopentanoate (134 g, 533 mmol) in THF:water:MeOH (2:2:1, 500 mL) was added lithium hydroxide (24.2 g, 587 mmol) and stirred at room temperature for 1 h. The solvent was removed under reduced pressure and added water (500 mL) to the residue. The mixture so formed was neutralized using 1N HCl solution, a solid product precipitated was filtered and dried under high vacuum to obtain 3-((5-fluoropyridin-2-yl)methylene)-4-oxopentanoic acid (110 g, 92% yield).
m/z 224.

Step-3: 2-Acetyl-7-fluoro-4H-quinolizin-4-one

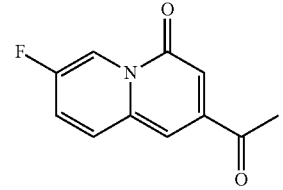

A stirred solution of 3-((5-fluoropyridin-2-yl)methylene)-4-oxopentanoic acid (109 g, 488 mmol) in dry DMF (300 mL) was cooled to 0° C., to which was added EDC.HCl (112 g, 586 mmol) and the reaction mixture stirred for 10 min. HOBT (82 g, 537 mmol) and TEA (102 mL, 733 mmol) was added to the reaction mixture at this temperature. The resulting reaction mixture was stirred at room temperature for 18 h. The reaction mixture was then poured into ice-water, the solid product precipitated was filtered, dried under vacuum to obtain 2-Acetyl-7-fluoro-4H-quinolizin-4-one (90 g, 90% yield).
m/z 206.

Step-4: 2-Acetyl-3-bromo-7-fluoro-4H-quinolizin-4-one

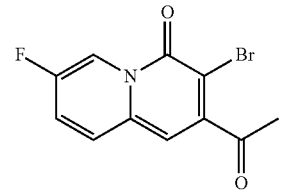 [SMILES: CC(=O)c1cc2ccc(F)cn2c(=O)c1Br]

To a stirred solution of 2-acetyl-7-fluoro-4H-quinolizin-4-one (75 g, 366 mmol) in DMF (400 mL) was added a solution of NBS (65.1 g, 366 mmol, 200 mL DMF) drop wise at 0-5° C. and stirred at 0-5° C. for 15 min. The reaction mixture was stirred at room temperature for 10 min. The reaction mixture was then poured into cold water; a solid product precipitated was filtered and dried under high vacuum to obtain 2-acetyl-3-bromo-7-fluoro-4H-quinolizin-4-one (85 g, 82% yield).
m/z 284, 286.

Step-5: 2-Acetyl-7-fluoro-3-phenyl-4H-quinolizin-4-one

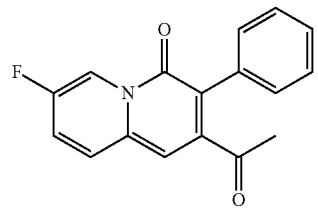 [SMILES: CC(=O)c1cc2ccc(F)cn2c(=O)c1-c1ccccc1]

To a stirred solution of 2-acetyl-3-bromo-7-fluoro-4H-quinolizin-4-one (85 g, 299 mmol), phenylboronic acid (39.8 g, 329 mmol) and Na₂CO₃ (95 g, 897 mmol) in water:ethanol:toluene (750 mL, 1:2:2) was added Tetrakis (triphenylphosphine)-palladium(0) (8.63 g, 7.47 mmol) with nitrogen purging for 10 min. The reaction mixture was then heated at 85° C. for 9 h. The solvent was removed from the reaction mixture under reduced pressure and the concentrate was extracted with ethyl acetate (3×500 mL), the combined organic layer was washed with water (1×500 mL), dried over anhydrous Na₂SO₄, filtered and concentrated under reduced pressure to obtain crude product. The crude was washed with 12% ethyl acetate-hexane to give 2-Acetyl-7-fluoro-3-phenyl-4H-quinolizin-4-one (77 g, 92% yield).

m/z 282.

Step-6: 2-(1-Aminoethyl)-7-fluoro-3-phenyl-4H-quinolizin-4-one

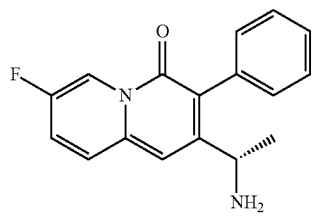 [SMILES: C[C@H](N)c1cc2ccc(F)cn2c(=O)c1-c1ccccc1]

To a stirred solution of 2-acetyl-7-fluoro-3-phenyl-4H-quinolizin-4-one (77 g, 273 mmol) in titanium(IV) isopropoxide (321 ml, 1095 mmol) was added (S)-2-methylpropane-2-sulfinamide (38 g, 314 mmol) at room temperature. The reaction mixture was heated at 100° C. for 9 h. The reaction mixture was diluted with DCM (2 L), saturated NaCl solution (750 mL), water (1.5 L) and stirred for 25 min at room temperature. The organic layer was separated and the aqueous layer was again stirred with DCM (3×500 mL). The combined organic layer was filtered through Celite bed and the bed was washed with DCM, the combined filtrate was then dried over anhydrous Na₂SO₄, filtered and concentrated under reduced pressure to obtain the crude product. The crude product was purified by flash column chromatography which yielded N-(1-(7-fluoro-4-oxo-3-phenyl-4H-quinolizin-2-yl)ethylidene)-2-methylpropane-2-sulfinamide (66 g, 62.7% yield).

To a stirred suspension of NaBH₄ (6.35 g, 171.8 mmol) in THF (500 mL) was added N-(1-(7-fluoro-4-oxo-3-phenyl-4H-quinolizin-2-yl)ethylidene)-2-methylpropane-2-sulfinamide (66 g, 171.8 mmol) at room temperature and the reaction mixture was heated at 45° C. for 1 to 1.5 h. The reaction mixture was quenched with NH₄Cl solution and extracted with ethyl acetate (3×500 mL), the combined organic layer was washed with saturated brine solution (1×500 mL), dried over anhydrous Na₂SO₄, filtered and concentrated under reduced pressure to obtain (S)—N-1-(7-fluoro-4-oxo-3-phenyl-4H-quinolizin-2-yl)ethyl)-2-methylpropane-2-sulfinamide.

In a round bottom flask (S)—N-1-(7-fluoro-4-oxo-3-phenyl-4H-quinolizin-2-yl)ethyl)-2-methylpropane-2-sulfinamide (66 g, 171 mmol) was taken in water (330 mL) and heated at 45° C., then added 330 mL of ethanol and heated at 80° C. for 10 min. The reaction mixture was stirred at room temperature for 3 h followed by cooling at 0-5° C. for 1 h. The solid product was filtered and washed with a chilled water-ethanol (330 mL, 4:1) and dried under high vacuum to obtain pure, (S)—N—(S)-1-(7-fluoro-4-oxo-3-phenyl-4H-quinolizin-2-yl)ethyl)-2-methylpropane-2-sulfinamide (36 g, 54.5% yield, purity=99.28%, Chiral purity=98.52%). The structure was confirmed by X-ray Diffractometry.

To a stirred solution of (S)—N—(S)-(1-(7-fluoro-4-oxo-3-phenyl-4H-quinolizin-2-yl)ethyl)-2-methylpropane-2-sulfinamide (36 g, 93 mmol) at 0° C. was slowly added methanolic-HCl (140 mL, 421 mmol) and stirred at room temperature for 30 min. The solvent was removed from the mixture under reduced pressure, following which, the residue was basified with saturated NaHCO₃ solution and extracted with ethyl acetate (5×300 mL), the combined organic layer was washed with water (1×100 mL), dried over anhydrous Na₂SO₄, filtered and concentrated under reduced pressure to obtain yellow solid compound (S)-2-(1-aminoethyl)-7-fluoro-3-phenyl-4H-quinolizin-4-one (23.6 g, 90% yield).

m/z 283.

Example 4: Preparation of 2-(1-Aminoethyl)-6-methyl-3-phenyl-4H-quinolizin-4-one

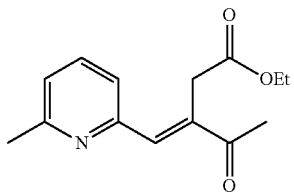 [SMILES: CCOC(=O)C/C(=C\c1cccc(C)n1)C(C)=O]

Step-1: ethyl 3-((6-methylpyridin-2-yl)methylene)-4-oxopentanoate

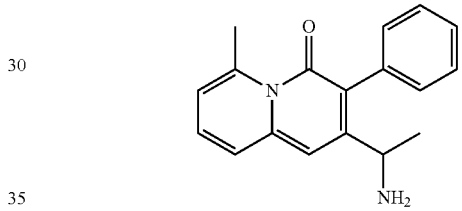

To a stirred solution of ethyl 3-(diethoxyphosphoryl)-4-oxopentanoate (12.72 g, 45.4 mmol) and 6-methylpicolinaldehyde (5 g, 41.3 mmol) in ethanol was added sodium ethoxide (3.09 g, 45.4 mmol) drop wise at 0° C. and stirred at this temperature for 1 h. The solvent was removed from the reaction mixture under reduced pressure and extracted with DCM (3×200 mL), the combined organic layer was washed with water (1×200 mL), dried over anhydrous Na₂SO₄, filtered and concentrated under reduced pressure to obtain crude product. The crude product was purified by Combiflash using 20% ethyl acetate-hexane as an eluent to yield ethyl 3-((6-methylpyridin-2-yl)methylene)-4-oxopentanoate (4.1 g, 40.2% yield).

m/z 248.

Step-2: 3-((6-methylpyridin-2-yl)methylene)-4-oxopentanoic acid

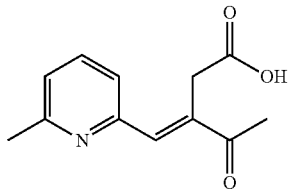 [SMILES: CC(=O)/C(=C/c1cccc(C)n1)CC(=O)O]

To a stirred solution of ethyl 3-((6-methylpyridin-2-yl)methylene)-4-oxopentanoate (15 g, 60.72 mmol) in THF-water (200 mL) was added sodium hydroxide (4.9 g, 121.44 mmol) and stirred at room temperature for 2 h. The reaction mixture was neutralized with 1N aqueous HCl and evaporated the solvent.

m/z 220.

Step-3: 2-acetyl-6-methyl-4H-quinolizin-4-one

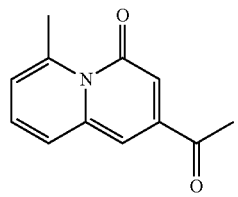

To a stirred solution of 3-((6-methylpyridin-2-yl)methylene)-4-oxopentanoic acid (12 g, 54.7 mmol) in dry DMF (50 mL) was added EDC.HCl (20.99 g, 109 mmol) at room temperature and stirred for 10 minutes. HOBT (12.57 g, 82 mmol) and TEA (22.89 mL, 164 mmol) were added to the reaction mixture and stirred at room temperature for 18 h. The reaction mixture was quenched with cold water and extracted with DCM (3×200 mL), the combined organic layer was washed with water (1×200 mL), dried over anhydrous Na$_2$SO$_4$, filtered and concentrated under reduced pressure to obtain crude product. The crude product was purified through Combiflash using 40% ethyl acetate-hexane as an eluent to obtain 2-acetyl-6-methyl-4H-quinolizin-4-one (7.1 g, 64.5% yield).

m/z 202.

Step-4: 2-acetyl-3-bromo-6-methyl-4H-quinolizin-4-one

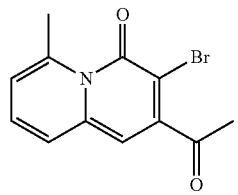 [SMILES: CC(=O)c1cc2cccc(C)n2c(=O)c1Br]

To a stirred solution of 2-acetyl-6-methyl-4H-quinolizin-4-one (7 g, 34.8 mmol) in DCM (50 mL) was added NBS (4.95 g, 27.8 mmol) lot wise at −10° C. and the reaction mixture was stirred at this temperature for 45 minutes. The reaction mixture was then diluted with water and extracted with DCM (3×200 mL), the combined organic layer was dried over anhydrous Na$_2$SO$_4$, filtered and concentrated under reduced pressure to obtain crude product. The crude product was purified by Combiflash using 25% ethyl acetate-hexane as an eluent to yield 2-acetyl-3-bromo-6-methyl-4H-quinolizin-4-one (7.3 g, 74.9% yield).

m/z 280, 282.

Step-5: 2-acetyl-6-methyl-3-phenyl-4H-quinolizin-4-one

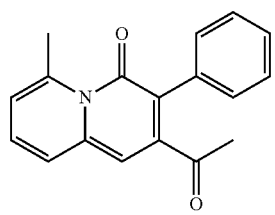 [SMILES: CC(=O)c1cc2cccc(C)n2c(=O)c1-c1ccccc1]

To the stirred solution of 2-acetyl-3-bromo-6-methyl-4H-quinolizin-4-one (5.8 g, 20.71 mmol), phenylboronic acid (3.03 g, 24.85 mmol) and Na$_2$CO$_3$ (6.58 g, 62.1 mmol) in water:ethanol:toluene (60 mL, 1:2:2) was added Tetrakis(triphenylphosphine)palladium(0) (1.196 g, 1.035 mmol) under nitrogen purging for 15 minutes. The reaction mixture was then heated at 80° C. for 12 h. The solvent was evaporated from the reaction mixture and the residue was purified by Combiflash using 25% ethyl acetate-hexane as an eluent to obtain 2-acetyl-6-methyl-3-phenyl-4H-quinolizin-4-one (5.41 g, 94% yield).

m/z 278.

Step-6: 2-(1-aminoethyl)-6-methyl-3-phenyl-4H-quinolizin-4-one

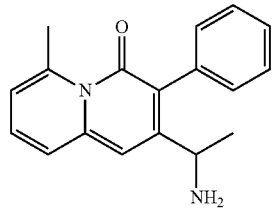

Method A: To a stirred solution of 2-acetyl-6-methyl-3-phenyl-4H-quinolizin-4-one (5.4 g, 19.47 mmol) in titanium isopropoxide (34.2 mL, 117 mmol) was added (S)-2-methylpropane-2-sulfinamide (2.83 g, 23.37 mmol) at 0° C. The reaction mixture was heated at 100° C. for 12-18 h. Then the reaction mixture was extracted with DCM and evaporated under reduced pressure to obtain a residue. The residue was then dissolved in MeOH and cooled to −78° C., to the mixture was then added NaBH$_4$ (2.95 g, 78 mmol) and stirred at −10° C. for 2 h. The reaction mixture was diluted with ethyl acetate and cold water. The organic layer was separated and concentrated under reduced pressure, the residue so obtained was stirred in dioxane-HCl (4M, 20 mL) for 15 minutes. The reaction mixture was basified with sodium bicarbonate and extracted in ethyl acetate (3×200 mL), the combined organic layer was washed with water (1×200 mL), dried over anhydrous Na$_2$SO$_4$, filtered and concentrated under reduced pressure to obtain crude product which was purified by Combiflash using 4-6% MeOH-DCM as an eluent to yield 2-(1-aminoethyl)-6-methyl-3-phenyl-4H-quinolizin-4-one (2.5 g) in 46% yield.

m/z 279.

Method B: To a stirred solution of 2-acetyl-6-methyl-3-phenyl-4H-quinolizin-4-one (150 mg, 0.541 mmol) in methanolic ammonia (5.02 mL, 35.2 mmol) was added NH$_4$Cl (289 mg, 5.41 mmol) at room temperature and heated at 60° C. for 9 h. After imine formation the reaction mixture was cooled to 0° C. and added NaBH$_4$ (30.7 mg, 0.811 mmol) and stirred at 0-5° C. for 15 minutes. The reaction mixture was quenched with cold water and evaporated the solvent from the reaction mixture under reduced pressure. The concentrate was then extracted with ethyl acetate (2×100 mL), dried over anhydrous Na$_2$SO$_4$, filtered and concentrated under reduced pressure to obtain crude product. The crude product was purified through Combiflash using 4-6% MeOH-DCM as an eluent to yield 2-(1-aminoethyl)-6-methyl-3-phenyl-4H-quinolizin-4-one (110 mg) in 73.1% yield.

Example 5

The following compounds were prepared using the procedure described in Example 4 with appropriate changes to the reactants and reaction conditions.
2-(1-aminoethyl)-3-(3-fluorophenyl)-6-methyl-4H-quinolizin-4-one
  m/z 297.
2-(1-aminoethyl)-3-(3,5-difluorophenyl)-6-methyl-4H-quinolizin-4-one
  m/z 315.
2-(1-aminoethyl)-3-(3,4-difluorophenyl)-6-methyl-4H-quinolizin-4-one
  m/z 315.
2-(1-aminoethyl)-7-fluoro-6-methyl-3-phenyl-4H-quinolizin-4-one
  m/z 297.
2-(1-aminoethyl)-7-fluoro-3-(3-fluorophenyl)-6-methyl-4H-quinolizin-4-one
  m/z 315.

Example 6: 2-(Hydroxymethyl)-6-methyl-3-phenyl-4H-quinolizin-4-one

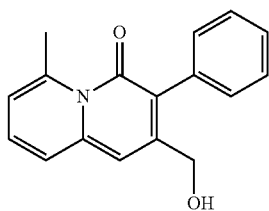 [SMILES: Cc1cccc2cc(CO)c(-c3ccccc3)c(=O)n12]

Step-1: Diethyl 2-((6-methylpyridin-2-yl)methylene)succinate

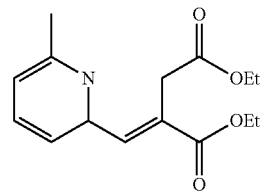 [SMILES: CCOC(=O)C/C(=C\C1C=CC=C(C)N1)C(=O)OCC]

To a stirred solution of diethyl 2-(diethoxyphosphoryl)succinate (7.5 g, 24.17 mmol) and sodium ethoxide (2.467 g, 36.3 mmol) in ethanol was added 6-methylpicolinaldehyde (3.51 g, 29.0 mmol) at room temperature. The reaction mixture was stirred at room temperature for 2 h and then heated at 50° C. for 1 h. The solvent was removed under reduced pressure and the residue so obtained was diluted with cold water and extracted with DCM (2×150 mL), the combined organic layer was washed with water (1×150 mL), dried over anhydrous Na$_2$SO$_4$, filtered and concentrated under reduced pressure to yield the crude product. The crude product was purified by flash chromatography using 10% ethyl acetate-hexane as an eluent to obtain diethyl 2-((6-methylpyridin-2-yl)methylene)succinate (2.5 g, 37.3%) yield.

m/z 278.

Step-2: Ethyl 6-methyl-4-oxo-4H-quinolizine-2-carboxylate

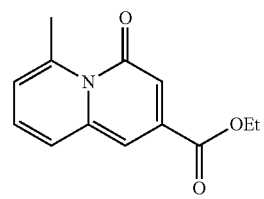 [SMILES: CCOC(=O)c1cc(=O)n2c(C)cccc2c1]

In a round bottom flask, PPA (1200 mg, 2.164 mmol) was taken and heated at 60° C., to which was added Diethyl 2-((6-methylpyridin-2-yl)methylene)succinate (600 mg, 2.164 mmol) during 1 h and then the temperature was slowly increased to 140° C. within 2 h and heated at 140° C. for 1 h. The reaction mixture was then allowed to cool to room temperature. The reaction mixture was then added to 20 mL of water and neutralized with saturated NaHCO$_3$ solution and the mixture was then extracted with DCM (2×100 mL), the combined organic layer was washed with water (1×100 mL), dried over anhydrous Na$_2$SO$_4$, filtered and concentrated under reduced pressure to obtain the crude product. The crude product was purified through Combiflash using 40% ethyl acetate-hexane as an eluent to obtain ethyl 6-methyl-4-oxo-4H-quinolizine-2-carboxylate (70 mg, 13.99%).

m/z 232.

Step-3: Ethyl 3-bromo-6-methyl-4-oxo-4H-quinolizine-2-carboxylate

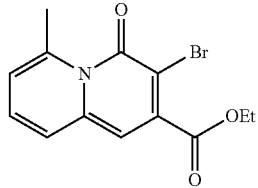 [SMILES: CCOC(=O)c1cc2cccc(C)n2c(=O)c1Br]

This compound was prepared by following the bromination method as described in step 3 of example 1 or step 4 of example 4.

m/z 310, 312.

Step-4: Ethyl 6-methyl-4-oxo-3-phenyl-4H-quinolizine-2-carboxylate

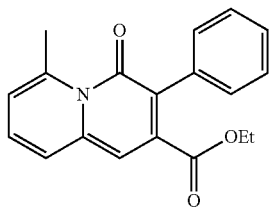

This compound was prepared by following the Suzuki coupling reaction method described in step 4 of example 1 or step 5 of example 4.

m/z 308.

Step-5: 6-methyl-4-oxo-3-phenyl-4H-quinolizine-2-carboxylic acid

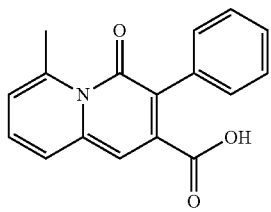 [SMILES: Cc1cccc2cc(C(=O)O)c(-c3ccccc3)c(=O)n12]

To a stirred solution of ethyl 6-methyl-4-oxo-3-phenyl-4H-quinolizine-2-carboxylate (300 mg, 0.976 mmol) in THF:ethanol:water (15 mL) was added NaOH (78 mg, 1.952 mmol) at room temperature and stirred for 12 h. The solvent was removed from the reaction mixture under reduced pressure, water was added to the residue and neutralized with 1 N aqueous HCl and the mixture was extracted with ethyl acetate (2×100 mL), the combined organic layer was washed with water (1×100 mL), dried over anhydrous Na$_2$SO$_4$, filtered and concentrated under reduced pressure to obtain a crude product. The crude product was purified by Combiflash to yield 6-methyl-4-oxo-3-phenyl-4H-quinolizine-2-carboxylic acid (250 mg, 92% yield).

m/z 280.

Step-6: 2-(hydroxymethyl)-6-methyl-3-phenyl-4H-quinolizin-4-one

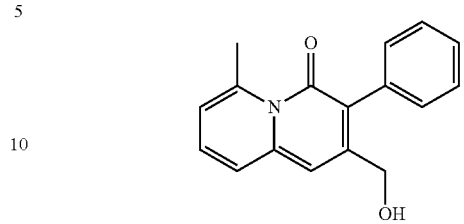

To a stirred solution of 6-methyl-4-oxo-3-phenyl-4H-quinolizine-2-carboxylic acid (250 mg, 0.895 mmol) in THF (20 mL) was added CDI (160 mg, 0.985 mmol) and heated at 55° C. for 30 minutes. The mixture so obtained was added drop wise to the suspension of NaBH$_4$ (135 mg, 3.58 mmol) in THF (20 mL) at 0° C. and stirred for 10 minutes at 0° C. The reaction mixture was then poured into 10 ml of saturated ammonium chloride solution and stirred at room temperature for 30 minutes. The mixture was then extracted with ethyl acetate (3×50 mL), the combined organic layer was washed with water (1×50 mL), dried over anhydrous Na$_2$SO$_4$, filtered and concentrated under reduced pressure to obtain crude product. The crude product was purified by Combiflash to obtain 2-(hydroxymethyl)-6-methyl-3-phenyl-4H-quinolizin-4-one (120 mg) in 50.5% yield.

m/z 266.

Example 7: 3-(3-Fluorophenyl)-2-(1-hydroxyethyl)-6-methyl-4H-quinolizin-4-one

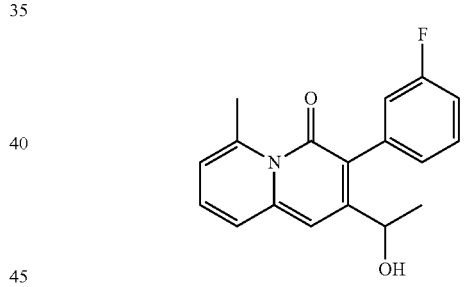

To a stirred solution of 2-acetyl-3-(3-fluorophenyl)-6-methyl-4H-quinolizin-4-one (1 g, 3.39 mmol) in EtOH (25 mL) was added NaBH$_4$ (0.512 g, 13.55 mmol) at room temperature and stirred for 30 minutes. The reaction mixture was then quenched with cold water and extracted with ethyl acetate (3×50 mL), the combined organic layer was washed with water (1×50 mL), dried over anhydrous Na$_2$SO$_4$, filtered and concentrated under reduced pressure to obtain 3-(3-Fluorophenyl)-2-(1-hydroxyethyl)-6-methyl-4H-quinolizin-4-one (950 mg) in 94% yield.

m/z 298.

Example 8

The following compounds were prepared using the procedure described in Example 6 and 7 with appropriate changes to the reactants and reaction conditions.

2-(hydroxymethyl)-3-phenyl-4H-quinolizin-4-one
m/z 252.

7-fluoro-2-(1-hydroxyethyl)-3-phenyl-4H-quinolizin-4-one
m/z 284.

Example 9: Preparation of 2-(1-((9H-purin-6-yl)amino)ethyl)-3-phenyl-4H-quinolizin-4-one (Compound 1)

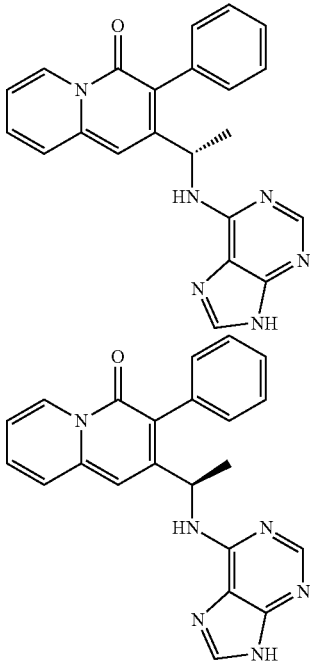

A stirred solution of 2-(1-aminoethyl)-3-phenyl-4H-quinolizin-4-one (300 mg, 1.136 mmol) and 6-chloro-9H-purine (227 mg, 1.477 mmol) in a mixture of ethanol-water (30 mL, 1:1) was heated at 100° C. for 20 h. The solvent was evaporated from the reaction mixture and the residue so obtained was purified through preparative HPLC to obtain a racemic product which was further purified through chiral HPLC to obtain two fractions. The first-eluting enantiomer on Chiral IA column is 1a (RT-5.87) and the second-eluting enantiomer on Chiral IA column is 1b (RT-10.36).

1a: $^1$H NMR (400 MHz, DMSO-d6) δ 8.87 (t, J=6.1 Hz, 1H), 8.38 (s, 2H), 8.14 (d, J=10.3 Hz, 2H), 7.89-7.26 (m, 7H), 7.21-6.91 (m, 2H), 5.23 (m, 1H), 1.33 (d, J=7.0 Hz, 3H).

m/z 383.

Example 10: Preparation of 2-(1-((9H-purin-6-yl)amino)ethyl)-6-methyl-3-phenyl-4H-quinolizin-4-one (Compound 2)

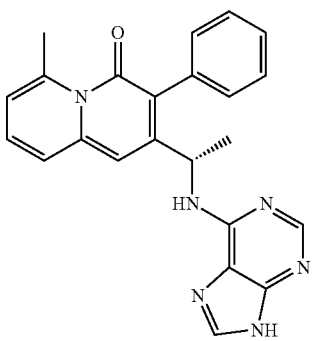

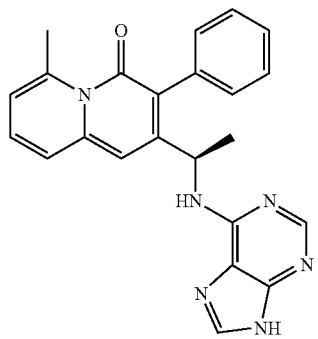

A stirred solution of 2-(1-Aminoethyl)-6-methyl-3-phenyl-4H-quinolizin-4-one (300 mg, 1.078 mmol) and 6-chloro-9H-purine (217 mg, 1.401 mmol) in a mixture of ethanol-water (30 mL, 1:1) and TEA (0.225 mL, 1.617 mmol) was heated at 100° C. for 20 h. The solvent was evaporated from the reaction mixture and the residue so obtained was purified through preparative HPLC to obtain racemic product which was further purified through chiral HPLC to obtain two fractions. The first-eluting enantiomer on Chiral IA column is 2a (RT-6.33) and the second-eluting enantiomer on Chiral IA column is 2b (RT-8.88).

2a: $^1$H NMR (400 MHz, DMSO-d6) δ 12.94 (s, 1H), 8.14 (s, 2H), 7.46 (m, 5H), 7.38-7.30 (m, 1H), 7.25 (d, J=8.9 Hz, 1H), 7.06 (m, 1H), 6.81 (s, 1H), 6.58 (d, J=6.7 Hz, 1H), 5.15 (m, 1H), 2.80 (s, 3H), 1.31 (d, J=7.0 Hz, 3H).

m/z 397.

Example: 11

The following compounds were prepared using the process described in Examples 9 and 10 with appropriate starting materials/intermediates and under appropriate reaction conditions.

2-(1-((9H-purin-6-yl)amino)ethyl)-7-methyl-3-phenyl-4H-quinolizin-4-one (Compound 3)

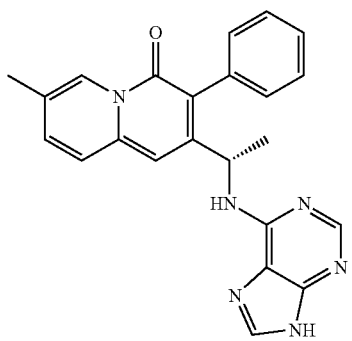

-continued

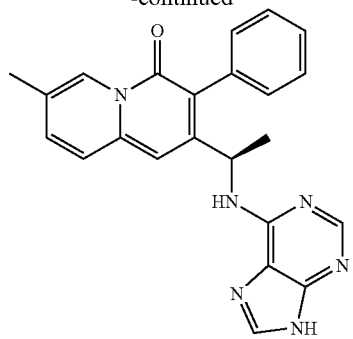

The racemic product was purified through chiral HPLC to obtain two fractions. The first-eluting enantiomer on Chiral IA column is 3a (RT-3.83) and the second-eluting enantiomer on Chiral IA column is 3b (RT-6.06).

3a: $^1$H NMR (400 MHz, DMSO-d6) δ 12.87 (s, 1H), 8.71 (s, 1H), 8.14 (d, J=8.6 Hz, 3H), 7.75-7.11 (m, 7H), 6.99 (s, 1H), 5.22 (m, 1H), 2.31 (s, 3H), 1.33 (d, J=7.0 Hz, 3H).

m/z 397.

4-Amino-6-((1-(4-oxo-3-phenyl-4H-quinolizin-2-yl)ethyl)amino)pyrimidine-5-carbonitrile (Compound 4)

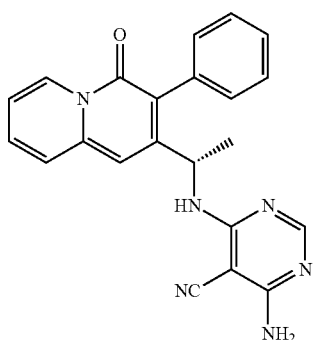

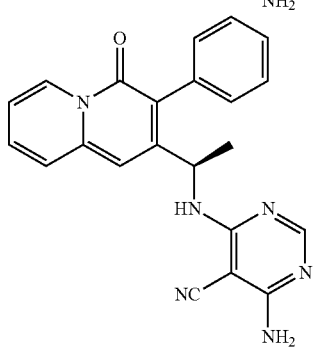

The racemic product was purified through chiral HPLC to obtain two fractions. The first-eluting enantiomer on CHIRALPAK IA column is 4a (RT-6.68) and the second-eluting enantiomer on CHIRALPAK IA column is 4b (RT-9.17).

4a: $^1$H NMR (400 MHz, DMSO-d6) δ 8.87 (dd, J=7.3, 1.2 Hz, 1H), 7.93 (s, 1H), 7.75-7.63 (m, 3H), 7.56-7.39 (m, 4H), 7.39-7.29 (m, 1H), 7.24 (s, 2H), 7.11 (m, 1H), 7.00 (s, 1H), 5.07 (m, 1H), 1.25 (d, J=7.1 Hz, 3H).

m/z 383.

2-(1-((9H-purin-6-yl)amino)ethyl)-3-(3-fluorophenyl)-4H-quinolizin-4-one (Compound 5)

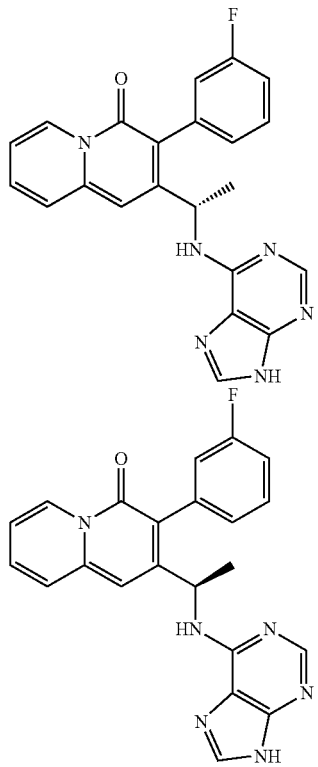

The racemic product was purified through chiral HPLC to obtain two fractions. The first-eluting enantiomer on Chiral IA column is 5a (RT-4.80) and the second-eluting enantiomer on Chiral IA column is 5b (RT-9.62).

5a: $^1$H NMR (400 MHz, DMSO-d6) δ 12.79 (s, 1H), 8.88 (d, J=7.4 Hz, 1H), 8.21 (s, 1H), 8.14 (d, J=10.6 Hz, 2H), 7.63 (d, J=8.9 Hz, 1H), 7.56-7.36 (m, 4H), 7.20 (m, 1H), 7.12 (t, J=7.0 Hz, 1H), 7.04 (s, 1H), 5.21 (m, 1H), 1.35 (d, J=6.7 Hz, 3H).

m/z 401.

4-Amino-6-((1-(3-(3-fluorophenyl)-4-oxo-4H-quinolizin-2-yl)ethyl)amino)-pyrimidine-5-carbonitrile (Compound 6)

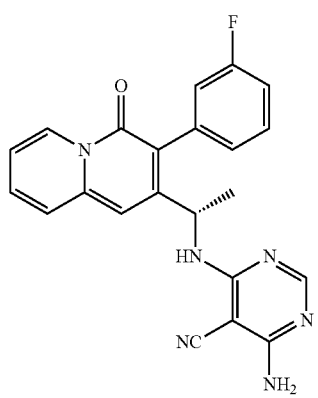

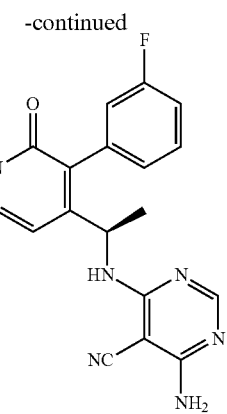

The racemic product was purified through chiral HPLC to obtain two fractions. The first-eluting enantiomer on CHIRALPAK IA column is 6a (RT-5.61) and the second-eluting enantiomer on CHIRALPAK IA column is 6b (RT-8.54).

6a: $^1$H NMR (400 MHz, DMSO-d6) δ 8.88 (d, J=7.4 Hz, 1H), 7.93 (s, 1H), 7.70 (t, J=7.2 Hz, 2H), 7.48 (q, J=7.6 Hz, 2H), 7.30-7.10 (m, 6H), 7.02 (s, 1H), 5.05 (q, J=7.2 Hz, 1H), 1.30 (d, J=7.0 Hz, 3H).

m/z 401.

4-Amino-6-((1-(6-methyl-4-oxo-3-phenyl-4H-quinolizin-2-yl)ethyl)amino)-pyrimidine-5-carbonitrile (Compound 7)

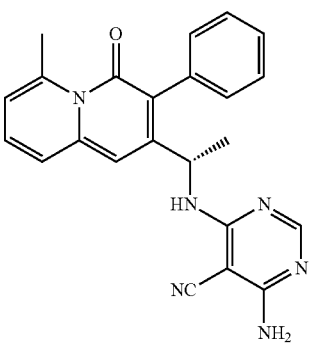

The racemic product was purified through chiral HPLC to obtain two fractions. The first-eluting enantiomer on Chiral IA column is 7a (RT-7.27) and the second-eluting enantiomer on Chiral IA column is 7b (RT-9.36).

7a: $^1$H NMR (400 MHz, DMSO-d6) δ 7.94 (s, 1H), 7.59 (d, J=7.0 Hz, 1H), 7.40 (d, J=5.7 Hz, 4H), 7.32 (d, J=8.5 Hz, 2H), 7.24 (s, 1H), 7.10 (t, J=7.8 Hz, 1H), 6.78 (s, 1H), 6.61 (d, J=6.7 Hz, 1H), 4.99 (m, 1H), 2.80 (s, 3H), 1.24 (d, J=7.1 Hz, 3H).

m/z 397.

2-(1-((2-Amino-9H-purin-6-yl)amino)ethyl)-6-methyl-3-phenyl-4H-quinolizin-4-one (Compound 8)

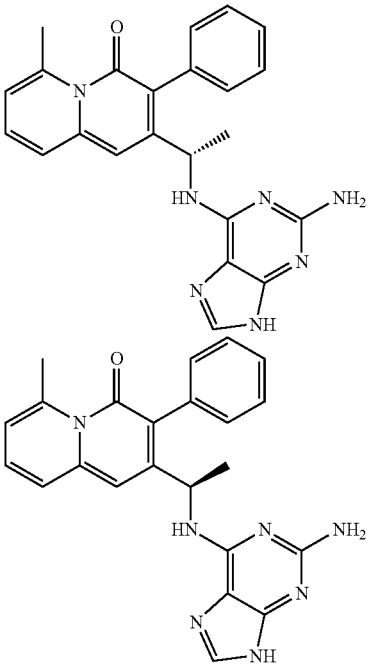

The racemic product was purified through chiral HPLC to obtain two fractions. The first-eluting enantiomer on CHIRALPAK IA column is 8a (RT-4.82) and the second-eluting enantiomer on CHIRALPAK IA column is 8b (RT-7.14).

8a: $^1$H NMR (400 MHz, DMSO-d6) δ 12.13 (s, 1H), 7.69 (s, 1H), 7.64 (s, 2H), 7.47 (t, J=6.8 Hz, 3H), 7.35 (s, 1H), 7.23 (d, J=8.8 Hz, 1H), 7.06 (m, 1H), 6.81 (s, 1H), 6.58 (m, 1H), 5.45-5.39 (m, 2H), 5.11 (m, 1H), 2.80 (s, 3H), 1.25 (d, J=6.5 Hz, 3H).

m/z 412.

2-(1-((2-Fluoro-9H-purin-6-yl)amino)ethyl)-6-methyl-3-phenyl-4H-quinolizin-4-one (Compound 9)

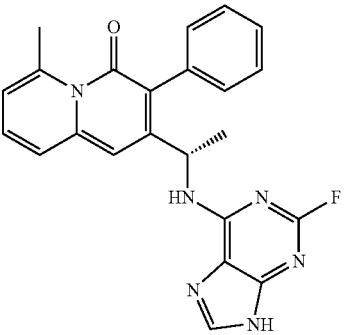

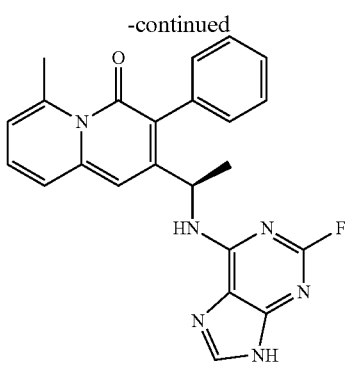

The racemic product was purified through chiral HPLC to obtain two fractions. The first-eluting enantiomer on CHIRALPAK IA column is 9a (RT-9.10) and the second-eluting enantiomer on CHIRALPAK IA column is 9b (RT-12.63).

9a: $^1$H NMR (400 MHz, DMSO-d6) δ 12.82 (s, 1H), 8.72 (s, 1H), 8.15 (s, 1H), 7.63 (s, 1H), 7.47-7.25 (m, 5H), 7.09 (m, 1H), 6.77 (s, 1H), 6.60 (d, J=6.7 Hz, 1H), 5.01 (m, 1H), 2.80 (s, 3H), 1.36 (d, J=6.7 Hz, 3H).

m/z 415.

4-Amino-6-((1-(3-(3-fluorophenyl)-6-methyl-4-oxo-4H-quinolizin-2-yl)ethyl)amino)pyrimidine-5-carbonitrile (Compound 10)

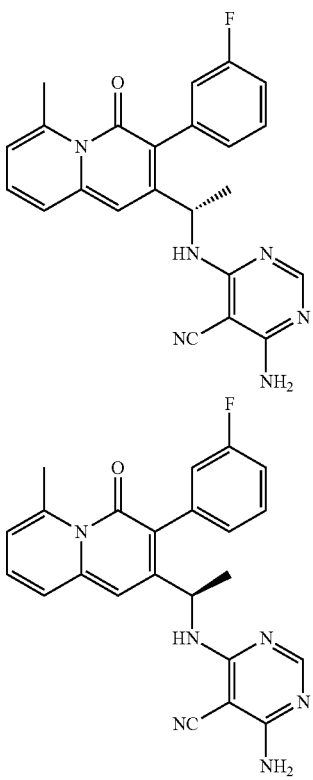

The racemic product was purified through chiral HPLC to obtain two fractions. The first-eluting enantiomer on CHIRALPAK IA column is 10a (RT-7.67) and the second-eluting enantiomer on CHIRALPAK IA column is 10b (RT-10.45).

10a: $^1$H NMR (400 MHz, DMSO-d6) δ 7.94 (s, 1H), 7.64 (d, J=6.9 Hz, 1H), 7.50-7.31 (m, 3H), 7.28-7.09 (m, 5H), 6.80 (s, 1H), 6.63 (d, J=6.7 Hz, 1H), 4.98 (m, 1H), 2.81 (s, 3H), 1.28 (d, J=7.0 Hz, 3H).

m/z 415.

2-(1-((9H-purin-6-yl)amino)ethyl)-3-(3-fluorophenyl)-6-methyl-4H-quinolizin-4-one (Compound 11)

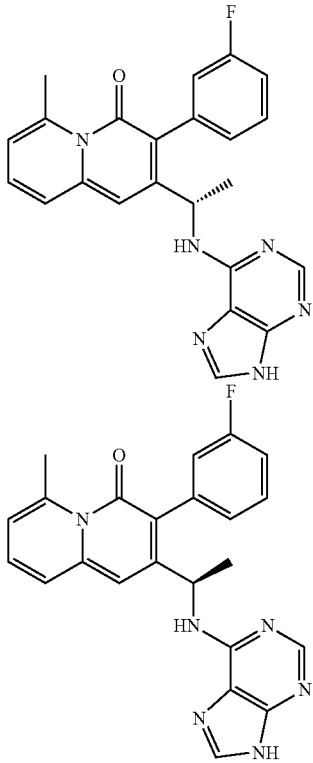

The racemic product was purified through chiral HPLC to obtain two fractions. The first-eluting enantiomer on CHIRALPAK IA column is 11a (RT-5.78) and the second-eluting enantiomer on CHIRALPAK IA column is 11b (RT-8.61).

11a: $^1$H NMR (400 MHz, DMSO-d6) δ 12.66 (s, 1H), 8.14 (d, J=5.2 Hz, 3H), 7.48 (q, J=7.3 Hz, 1H), 7.36 (s, 2H), 7.28 (d, J=8.7 Hz, 1H), 7.13 (m, 2H), 6.82 (s, 1H), 6.61 (d, J=6.6 Hz, 1H), 5.14 (m, 1H), 2.82 (s, 3H), 1.33 (d, J=6.7 Hz, 3H).

m/z 415.

2-(1-((2-Amino-9H-purin-6-yl)amino)ethyl)-3-(3-fluorophenyl)-6-methyl-4H-quinolizin-4-one (Compound 12)

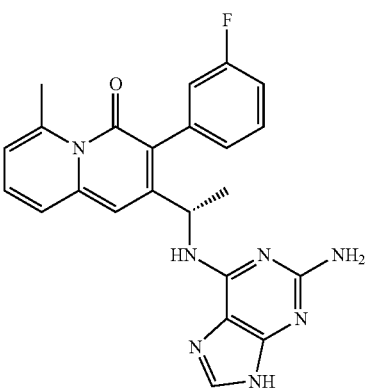

-continued

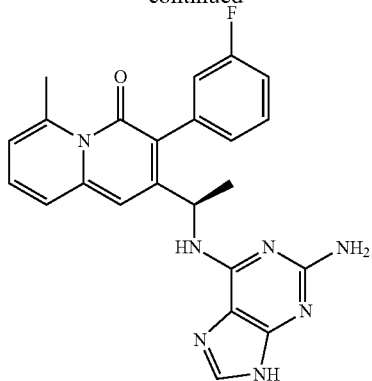

The racemic product was purified through chiral HPLC to obtain two fractions. The first-eluting enantiomer on CHIRALPAK IA column is 12a (RT-8.62) and the second-eluting enantiomer on CHIRALPAK IA column is 12b (RT-14.78).

12a: $^1$H NMR (400 MHz, DMSO-d6) δ 12.14 (s, 1H), 7.70 (s, 2H), 7.51 (q, J=7.5 Hz, 1H), 7.36 (s, 3H), 7.29-7.05 (m, 3H), 6.83 (s, 1H), 6.61 (d, J=6.8 Hz, 1H), 5.43 (s, 2H), 5.09 (m, 1H), 2.81 (s, 3H), 1.26 (d, J=6.7 Hz, 3H).

m/z 430.

2-(1-((9H-purin-6-yl)amino)ethyl)-7-fluoro-3-phenyl-4H-quinolizin-4-one (Compound 13)

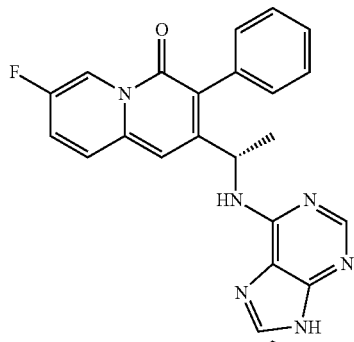

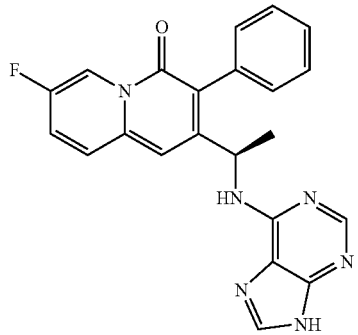

The racemic product was purified through chiral HPLC to obtain two fractions. The first-eluting enantiomer on CHIRALPAK IA column is 13a (RT-4.40) and the second-eluting enantiomer on CHIRALPAK IA column is 13b (RT-6.12).

13a: $^1$H NMR (400 MHz, DMSO-d6) δ 8.80 (m, 1H), 8.14 (d, J=10.1 Hz, 3H), 7.77 (m, 2H), 7.63-7.24 (m, 5H), 7.14 (s, 1H), 5.22 (m, 1H), 1.33 (d, J=7.0 Hz, 3H).

m/z 401.

4-Amino-6-((1-(7-fluoro-4-oxo-3-phenyl-4H-quinolizin-2-yl)ethyl)amino)-pyrimidine-5-carbonitrile (Compound 14)

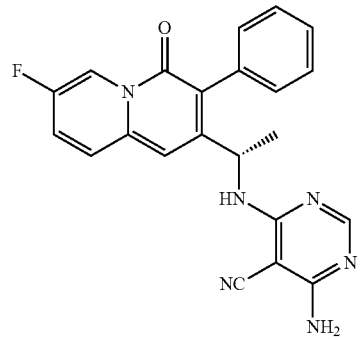

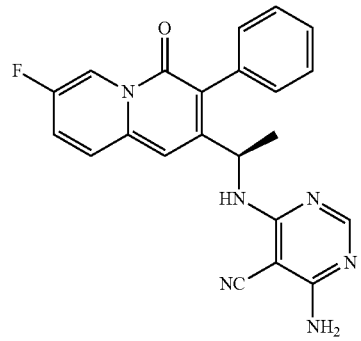

The racemic product was purified through chiral HPLC to obtain two fractions. The first-eluting enantiomer on CHIRALPAK IA column is 14a (RT-5.89) and the second-eluting enantiomer on CHIRALPAK IA column is 14b (RT-8.38).

14a: $^1$H NMR (400 MHz, DMSO-d6) δ 8.80 (dd, J=6.0, 2.5 Hz, 1H), 7.93 (s, 1H), 7.83 (m, 1H), 7.68 (d, J=6.7 Hz, 1H), 7.59 (m, 1H), 7.49-7.32 (m, 4H), 7.25 (s, 2H), 7.13 (d, J=3.1 Hz, 1H), 5.06 (m, 1H), 1.27 (d, J=6.7 Hz, 3H).

m/z 401.

2-(1-((2-Amino-9H-purin-6-yl)amino)ethyl)-7-fluoro-3-(3-fluorophenyl)-4H-quinolizin-4-one (Compound 15)

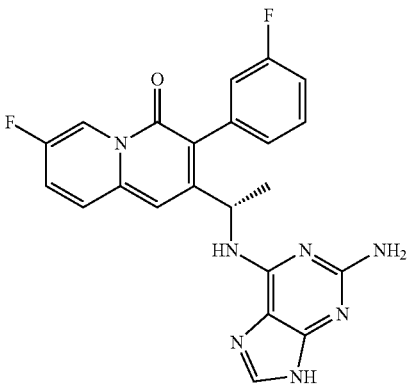

-continued

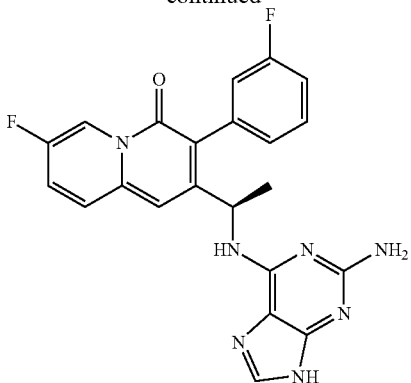

The racemic product was purified through chiral HPLC to obtain two fractions. The first-eluting enantiomer on Chiral IA column is 15a (RT-5.46) and the second-eluting enantiomer on Chiral IA column is 15b (RT-7.30).

15a: ¹H NMR (400 MHz, DMSO-d6) δ 12.26-12.07 (m, 1H), 8.82 (m, 1H), 8.06-7.67 (m, 3H), 7.67-7.30 (m, 4H), 7.31-7.01 (m, 2H), 5.39 (s, 2H), 5.16 (m, 1H), 1.23 (d, J=3.9 Hz, 3H).

m/z 434.

4-Amino-6-((1-(7-fluoro-3-(3-fluorophenyl)-4-oxo-4H-quinolizin-2-yl)ethyl)amino)pyrimidine-5-carbonitrile (Compound 16)

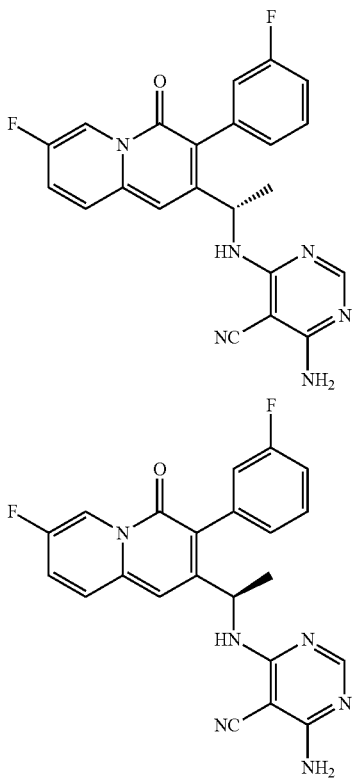

The racemic product was purified through chiral HPLC to obtain two fractions. The first-eluting enantiomer on Chiral IA column is 16a (RT-5.00) and the second-eluting enantiomer on Chiral IA column is 16b (RT-6.53).

16a: ¹H NMR (400 MHz, DMSO-d6) δ 8.82 (m, 1H), 7.93 (s, 1H), 7.85 (m, 1H), 7.72 (d, J=6.7 Hz, 1H), 7.63 (m, 1H), 7.58-7.00 (m, 7H), 5.05 (m, 1H), 1.31 (d, J=7.0 Hz, 3H).

m/z 419.

4-Amino-6-((1-(3-(3,5-difluorophenyl)-6-methyl-4-oxo-4H-quinolizin-2-yl)ethyl)amino)pyrimidine-5-carbonitrile (Compound 17)

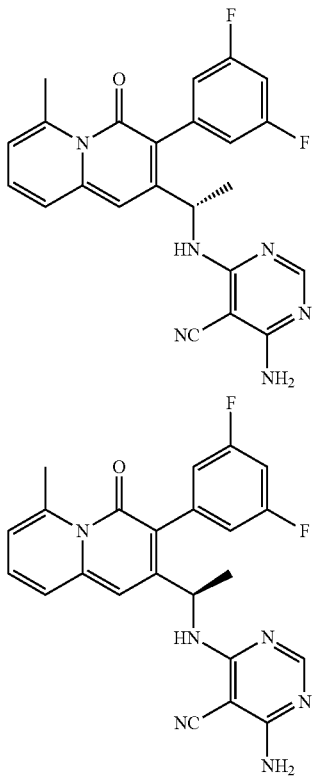

The racemic product was purified through chiral HPLC to obtain two fractions. The first-eluting enantiomer on Chiral IA column is 17a (RT-8.74) and the second-eluting enantiomer on Chiral IA column is 17b (RT-11.42).

17a: ¹H NMR (400 MHz, DMSO-d6) δ 7.93 (s, 1H), 7.65 (d, J=6.9 Hz, 1H), 7.37 (d, J=8.6 Hz, 1H), 7.27 (d, J=8.5 Hz, 2H), 7.16 (m, 4H), 6.82 (s, 1H), 6.66 (m, 1H), 4.98 (m, 1H), 2.83 (s, 3H), 1.30 (d, J=6.5 Hz, 3H).

m/z 433.

2-(1-((2-amino-9H-purin-6-yl)amino)ethyl)-3-(3,5-difluorophenyl)-6-methyl-4H-quinolizin-4-one (Compound 18)

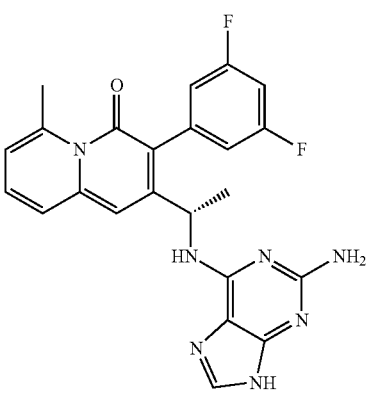

-continued

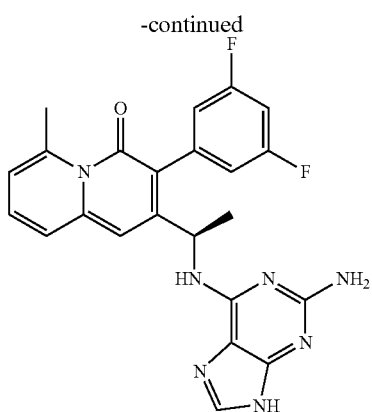

The racemic product was purified through chiral HPLC to obtain two fractions. The first-eluting enantiomer on CHIRALPAK IA column is 18a (RT-8.00) and the second-eluting enantiomer on CHIRALPAK IA column is 18b (RT-13.75).

18a: $^1$H NMR (400 MHz, DMSO-d6) δ 12.18 (s, 1H), 7.71 (s, 2H), 7.29 (m, 5H), 6.84 (s, 1H), 6.64 (d, J=6.8 Hz, 1H), 5.49 (s, 2H), 5.08 (m, 1H), 2.83 (s, 3H), 1.29 (d, J=6.8 Hz, 3H).

m/z 448.

4-Amino-6-((1-(3-(3,4-difluorophenyl)-6-methyl-4-oxo-4H-quinolizin-2-yl)ethyl)amino)pyrimidine-5-carbonitrile (Compound 19)

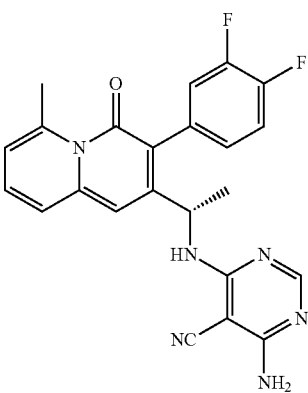

The racemic product was purified through chiral HPLC to obtain two fractions. The first-eluting enantiomer on Chiral IA column is 19a (RT-8.41) and the second-eluting enantiomer on Chiral IA column is 19b (RT-12.91).

19a: $^1$H NMR (400 MHz, DMSO-d6) δ 7.94 (s, 1H), 7.64 (d, J=7.0 Hz, 1H), 7.44 (m, 2H), 7.38-7.32 (m, 1H), 7.26 (s, 3H), 7.15 (m, 1H), 6.81 (s, 1H), 6.64 (m, 1H), 5.03-4.84 (m, 1H), 2.82 (s, 3H), 1.30 (d, J=7.0 Hz, 3H).

m/z 433.

2-Amino-4-((1-(7-fluoro-3-(3-fluorophenyl)-4-oxo-4H-quinolizin-2-yl)ethyl)amino)pyrimidine-5-carbonitrile (Compound 20)

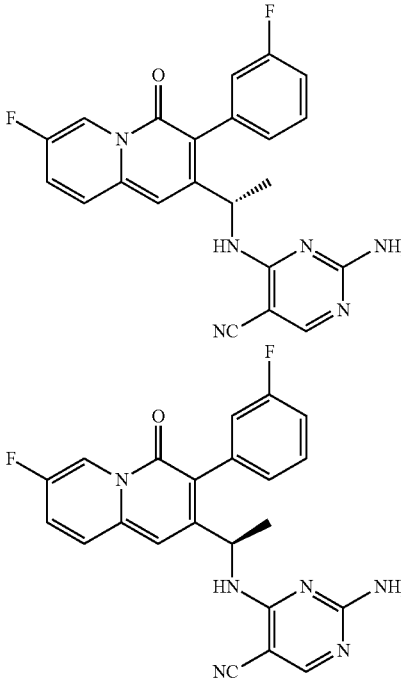

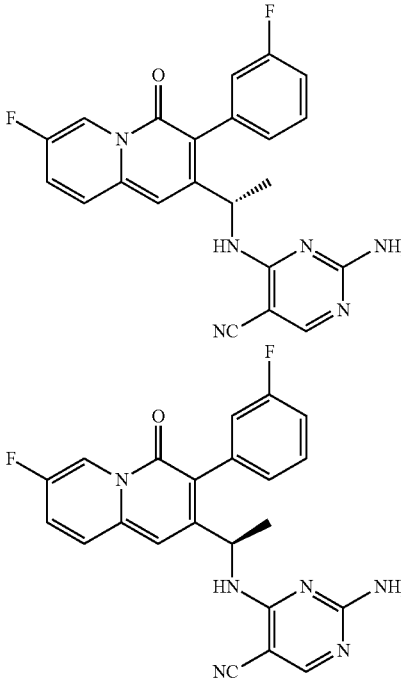

The racemic product was purified through chiral HPLC to obtain two fractions. The first-eluting enantiomer on CHIRALPAK IA column is 20a (RT-6.19) and the second-eluting enantiomer on CHIRALPAK IA column is 20b (RT-8.98).

20a: $^1$H NMR (400 MHz, DMSO-d6) δ 8.84 (m, 1H), 8.17 (s, 1H), 7.89 (m, 1H), 7.77-7.59 (m, 2H), 7.59-7.23 (m, 3H), 7.19 (m, 2H), 7.10 (s, 1H), 6.52 (s, 1H), 5.14-4.99 (m, 1H), 1.25 (d, J=7.0 Hz, 3H).

m/z 419.

2-Amino-4-((1-(7-fluoro-3-(3-fluorophenyl)-4-oxo-4H-quinolizin-2-yl)ethyl)amino)-6-methylpyrimidine-5-carbonitrile (Compound 21)

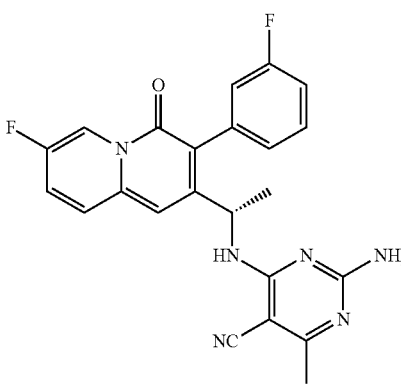

-continued

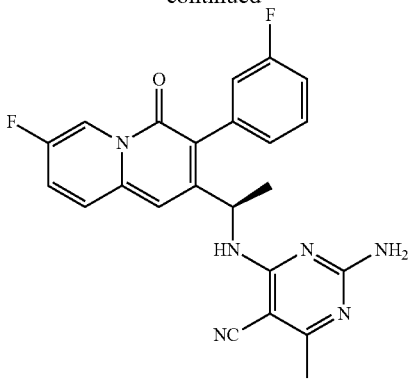

The racemic product was purified through chiral HPLC to obtain two fractions. The first-eluting enantiomer on CHIRALPAK IA column is 21a (RT-5.39) and the second-eluting enantiomer on CHIRALPAK IA column is 21b (RT-8.61).

21a: ¹H NMR (400 MHz, DMSO-d6) δ 8.84 (m, 1H), 7.88 (m, 1H), 7.64 (m, 1H), 7.50 (m, 2H), 7.44-7.13 (m, 3H), 7.10 (s, 1H), 6.42 (s, 1H), 5.17-4.95 (m, 1H), 2.24 (s, 3H), 1.27 (d, J=7.2 Hz, 3H).

m/z 433.

4-Amino-6-((1-(7-fluoro-6-methyl-4-oxo-3-phenyl-4H-quinolizin-2-yl)ethyl)amino)pyrimidine-5-carbonitrile (Compound 22)

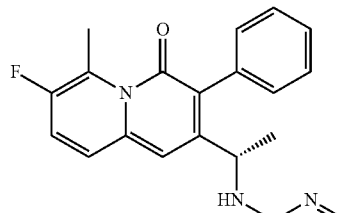

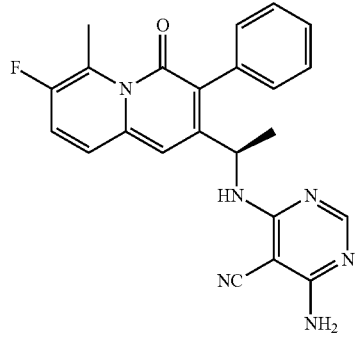

The racemic product was purified through chiral HPLC to obtain two fractions. The first-eluting enantiomer on CHIRALPAK IA column is 22a (RT-4.86) and the second-eluting enantiomer on CHIRALPAK IA column is 22b (RT-5.63).

22a: ¹H NMR (400 MHz, Chloroform-δ 8.12 (s, 1H), 7.47 (m, 5H), 7.18 (m 1H), 7.10-6.96 (m, 1H), 6.49 (s, 1H), 5.66 (s, 2H), 5.48 (s, 1H), 5.18 (m, 1H), 2.89 (d, J=4.3 Hz, 3H), 1.39 (d, J=6.9 Hz, 3H).

m/z 415.

4-Amino-6-((1-(7-fluoro-3-(3-fluorophenyl)-6-methyl-4-oxo-4H-quinolizin-2-yl)ethyl)amino)pyrimidine-5-carbonitrile (Compound 23)

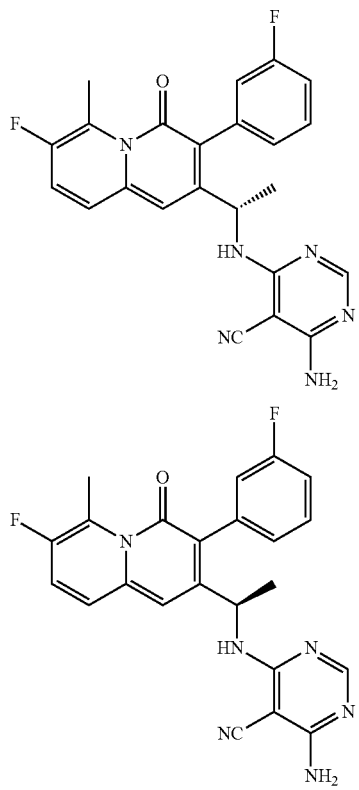

The racemic product was purified through chiral HPLC to obtain two fractions. The first-eluting enantiomer on CHIRALPAK IA column is 23a (RT-5.72) and the second-eluting enantiomer on CHIRALPAK IA column is 23b (RT-6.87).

23a: ¹H NMR (400 MHz, Chloroform-d) δ 8.13 (s, 1H), 7.44 (m, 1H), 7.38-7.14 (m, 2H), 7.15-6.96 (m, 2H), 6.50 (s, 1H), 5.67 (s, 2H), 5.51 (s, 1H), 5.16 (m, 1H), 5.09-4.86 (m, 1H), 2.90 (d, J=4.3 Hz, 3H), 1.40 (d, J=7.0 Hz, 3H).

m/z 433.

2-(1-((9H-purin-6-yl)amino)ethyl)-7-fluoro-6-methyl-3-phenyl-4H-quinolizin-4-one (Compound 24)

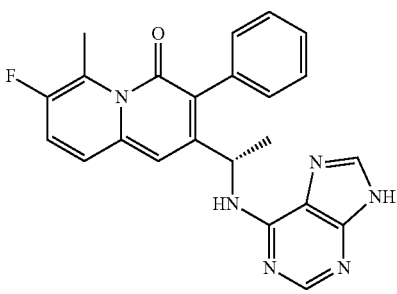

-continued

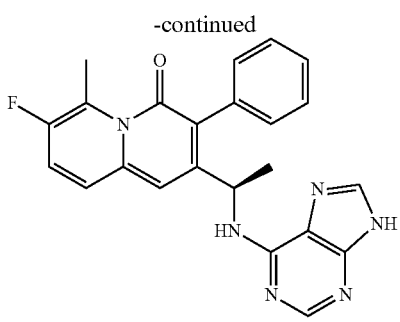

The racemic product was purified through chiral HPLC to obtain two fractions. The first-eluting enantiomer on CHIRALPAK IA column is 24a (RT-7.18) and the second-eluting enantiomer on CHIRALPAK IA column is 24b (RT-9.17).

24a: $^1$H NMR (400 MHz, Chloroform-d) δ 8.36 (s, 1H), 7.93 (s, 1H), 7.49 (m, 4H), 7.16-7.01 (m, 1H), 6.96 (m, 1H), 6.72-6.50 (m, 1H), 6.18 (d, J=9.9 Hz, 1H), 5.33 (s, 1H), 4.98 (m, 1H), 2.89 (d, J=4.3 Hz, 3H), 1.44 (d, J=7.1 Hz, 3H).

m/z 415.

(S)-2,4-diamino-6-((1-(7-fluoro-4-oxo-3-phenyl-4H-quinolizin-2-yl)ethyl)amino)-pyrimidine-5-carbonitrile (Compound 25)

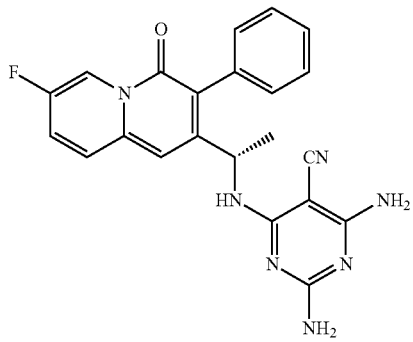 [SMILES: C[C@H](Nc1nc(N)nc(N)c1C#N)c1cc2ccc(F)cn2c(=O)c1-c1ccccc1]

$^1$H NMR (400 MHz, DMSO-d6) δ 12.76 (s, 1H), 8.82 (dd, J=6.0, 2.5 Hz, 1H), 8.14 (s, 1H), 7.91-7.79 (m, 1H), 7.59 (m, 1H), 7.47 (t, J=7.4 Hz, 3H), 7.41-7.32 (m, 2H), 7.10 (s, 1H), 7.03-6.92 (m, 1H), 6.56 (s, 2H), 5.08 (m, 1H), 1.20 (d, J=7.1 Hz, 3H).

m/z 416.

(S)-2-amino-4-((1-(7-fluoro-4-oxo-3-phenyl-4H-quinolizin-2-yl)ethyl)amino)pyrimidine-5-carbonitrile (Compound 26)

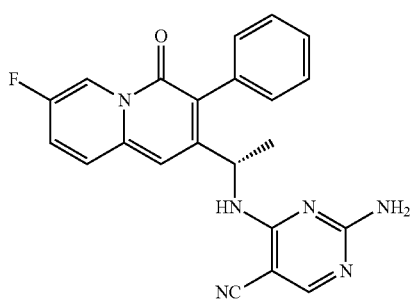 [SMILES: C[C@H](Nc1nc(N)ncc1C#N)c1cc2ccc(F)cn2c(=O)c1-c1ccccc1]

$^1$H NMR (400 MHz, DMSO-d6) δ 8.83 (dd, J=6.1, 2.5 Hz, 1H), 8.18 (s, 1H), 7.87 (dd, J=9.8, 5.7 Hz, 1H), 7.72-7.57 (m, 3H), 7.42 (m, 4H), 7.09 (s, 1H), 6.47 (brs, 1H), 5.12 (m, 1H), 1.23 (d, J=6.8 Hz, 3H).

m/z 401.

(S)-2-amino-4-((1-(7-fluoro-4-oxo-3-phenyl-4H-quinolizin-2-yl)ethyl)amino)-6-methylpyrimidine-5-carbonitrile (Compound 27)

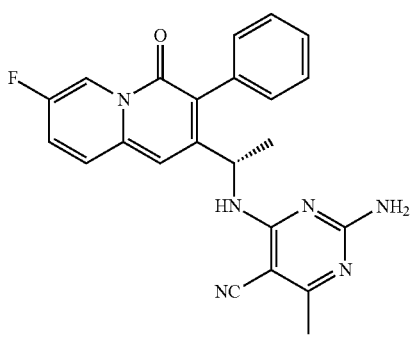 [SMILES: Cc1nc(N)nc(N[C@@H](C)c2cc3ccc(F)cn3c(=O)c2-c2ccccc2)c1C#N]

$^1$H NMR (400 MHz, DMSO-d6) δ 8.83 (dd, J=6.0, 2.5 Hz, 1H), 7.85 (dd, J=9.8, 5.8 Hz, 1H), 7.61 (m, 2H), 7.47 (m, 4H), 7.41-7.27 (m, 2H), 7.10 (s, 1H), 6.36 (brs, 1H), 5.10 (m, 1H), 2.25 (s, 3H), 1.23 (d, J=7.0 Hz, 3H).

m/z 415.

(S)-4-((1-(7-fluoro-4-oxo-3-phenyl-4H-quinolizin-2-yl)ethyl)amino)-7H-pyrrolo[2,3-d]pyrimidine-5-carbonitrile (Compound 28)

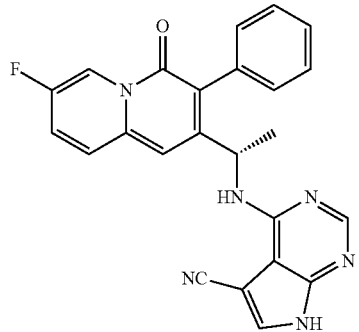 [SMILES: C[C@H](Nc1ncnc2[nH]cc(C#N)c12)c1cc2ccc(F)cn2c(=O)c1-c1ccccc1]

$^1$H NMR (400 MHz, DMSO-d6) δ 12.76 (s, 1H), 8.82 (dd, J=6.1, 2.5 Hz, 1H), 8.20 (d, J=3.1 Hz, 2H), 7.80 (m, 1H), 7.63-7.32 (m, 6H), 7.29 (s, 1H), 6.61 (d, J=5.9 Hz, 1H), 5.10 (m, 1H), 1.39 (d, J=6.9 Hz, 3H).

m/z 425.

(S)-4-amino-6-((1-(7-fluoro-3-(3-fluoro-5-methyl-phenyl)-4-oxo-4H-quinolizin-2-yl)ethyl)amino)pyrimidine-5-carbonitrile (Compound 29)

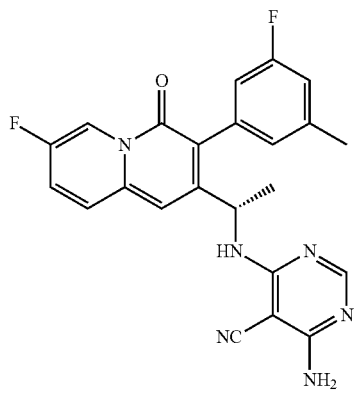 [SMILES: Cc1cc(F)cc(-c2c([C@H](C)Nc3ncnc(N)c3C#N)cc3ccc(F)cn3c2=O)c1]

¹H NMR (400 MHz, DMSO-d6) δ 8.82 (dd, J=6.0, 2.5 Hz, 1H), 7.93 (s, 1H), 7.86 (dd, J=9.8, 5.8 Hz, 1H), 7.73-7.59 (m, 2H), 7.31-7.24 (m, 3H), 7.15 (s, 1H), 7.05-6.95 (m, 1H), 5.09 (m, 1H), 2.35 (s, 3H), 1.31 (d, J=7.0 Hz, 3H).
m/z 433.

(S)-2,4-diamino-6-((1-(7-fluoro-3-(3-fluoro-5-methylphenyl)-4-oxo-4H-quinolizin-2-yl)ethyl)amino)pyrimidine-5-carbonitrile (Compound 30)

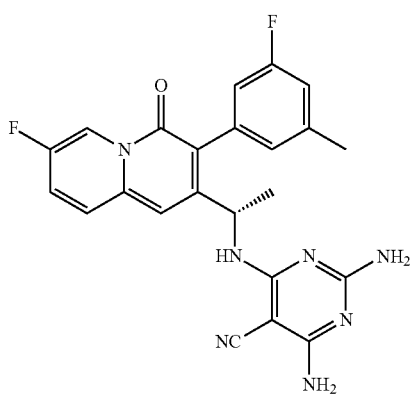 [SMILES: Cc1cc(F)cc(-c2c([C@H](C)Nc3nc(N)nc(N)c3C#N)cc3ccc(F)cn3c2=O)c1]

¹H NMR (400 MHz, DMSO-d6) δ 8.82 (dd, J=6.0, 2.5 Hz, 1H), 7.87 (dd, J=9.8, 5.7 Hz, 1H), 7.63 (m, 1H), 7.13 (s, 1H), 7.01 (d, J=9.9 Hz, 1H), 6.93 (d, J=6.8 Hz, 1H), 6.57 (s, 2H), 5.05 (m, 1H), 2.36 (s, 3H), 1.24 (d, J=6.8 Hz, 3H).
m/z 448.

(S)-4-amino-6-((1-(7-fluoro-4-oxo-3-(m-tolyl)-4H-quinolizin-2-yl)ethyl)amino)pyrimidine-5-carbonitrile (Compound 31)

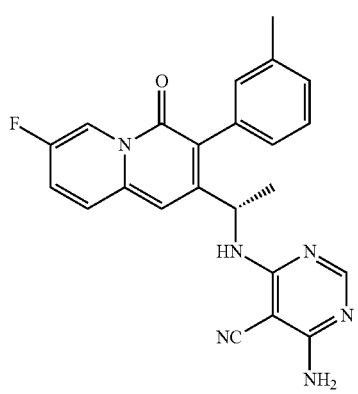 [SMILES: Cc1cccc(-c2c([C@H](C)Nc3ncnc(N)c3C#N)cc3ccc(F)cn3c2=O)c1]

¹H NMR (400 MHz, DMSO-d6) δ 8.80 (dd, J=6.1, 2.5 Hz, 1H), 7.94 (s, 1H), 7.83 (dd, J=9.8, 5.8 Hz, 1H), 7.67 (d, J=6.9 Hz, 1H), 7.60 (m, 1H), 7.31 (m, 4H), 7.19-6.77 (m, 3H), 5.09 (m, 1H), 2.34 (s, 3H), 1.36-1.21 (d, J=6.7 Hz, 3H).
m/z 415.

(S)-2,4-diamino-6-((1-(7-fluoro-4-oxo-3-(m-tolyl)-4H-quinolizin-2-yl)ethyl)-amino)pyrimidine-5-carbonitrile (Compound 32)

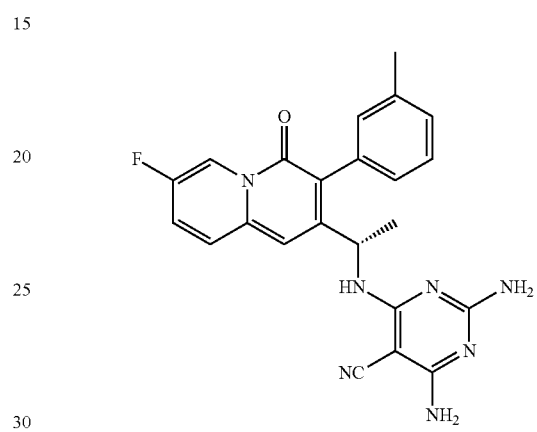

¹H NMR (400 MHz, DMSO-d6) δ 8.81 (dd, J=6.0, 2.5 Hz, 1H), 7.84 (dd, J=9.8, 5.8 Hz, 1H), 7.60 (m, 1H), 7.35 (s, 2H), 7.30-7.00 (m, 3H), 6.94 (d, J=6.9 Hz, 1H), 6.57 (s, 2H), 6.11 (bs, 2H), 5.22-4.94 (m, 1H), 2.35 (s, 3H), 1.26 (d, J=6.8 Hz, 3H).
m/z 430.

(S)-2-(1-((2-amino-9H-purin-6-yl)amino)ethyl)-7-fluoro-3-phenyl-4H-quinolizin-4-one (Compound 33)

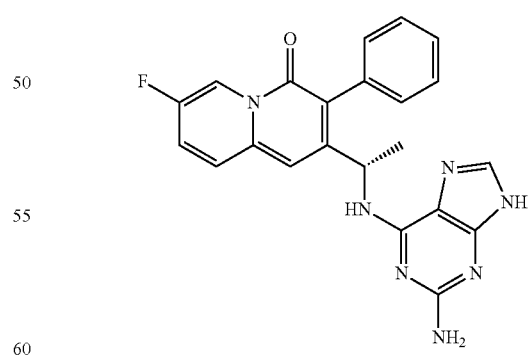

¹H NMR (400 MHz, DMSO-d6) δ 12.19 (s, 1H), 8.80 (dd, J=6.1, 2.5 Hz, 1H), 8.15 (s, 1H), 7.83-7.66 (m, 3H), 7.64-7.31 (m, 5H), 7.13 (s, 1H), 5.43 (s, 2H), 5.19 (m, 1H), 1.33 (d, J=6.7 Hz, 3H).
m/z 416.

(S)-4-amino-6-((1-(7-fluoro-4-oxo-3-(3-(trifluoromethoxy)phenyl)-4H-quinolizin-2-yl)ethyl)amino)pyrimidine-5-carbonitrile (Compound 34)

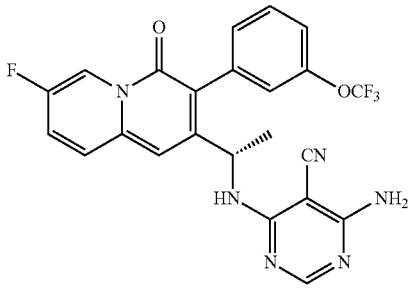 [SMILES: C[C@H](Nc1ncnc(N)c1C#N)c1cc2ccc(F)cn2c(=O)c1-c1cccc(OC(F)(F)F)c1]

$^1$H NMR (400 MHz, DMSO-d6) δ 8.83 (dd, J=6.0, 2.4 Hz, 1H), 8.00-7.81 (m, 2H), 7.76 (d, J=6.7 Hz, 1H), 7.71-7.56 (m, 2H), 7.56-7.34 (m, 3H), 7.28 (s, 2H), 7.17 (s, 1H), 5.01 (m, 1H), 1.32 (d, J=7.0 Hz, 3H).
m/z 485.

(S)-2-(1-((2-amino-9H-purin-6-yl)amino)ethyl)-7-fluoro-3-(3-(trifluoromethoxy)-phenyl)-4H-quinolizin-4-one (Compound 35)

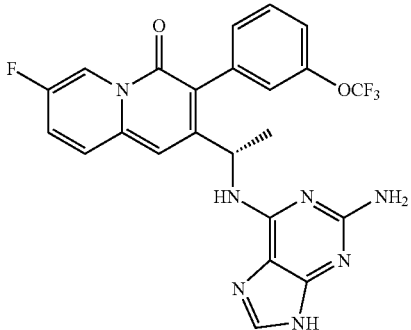 [SMILES: C[C@H](Nc1nc(N)nc2[nH]cnc12)c1cc2ccc(F)cn2c(=O)c1-c1cccc(OC(F)(F)F)c1]

$^1$H NMR (400 MHz, DMSO-d6) δ 8.84 (dd, J=6.0, 2.5 Hz, 1H), 8.17 (s, 1H), 7.98-7.50 (m, 5H), 7.40 (d, J=7.9 Hz, 1H), 7.16 (s, 1H), 5.43 (s, 2H), 5.13 (m, 1H), 1.26 (d, J=6.8 Hz, 3H).
m/z 500.

(S)-4-amino-6-((1-(7-fluoro-3-(4-fluorophenyl)-4-oxo-4H-quinolizin-2-yl)ethyl)amino)pyrimidine-5-carbonitrile (Compound 36)

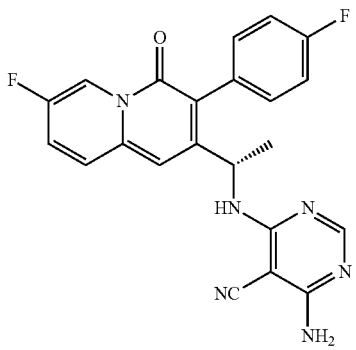 [SMILES: C[C@H](Nc1ncnc(N)c1C#N)c1cc2ccc(F)cn2c(=O)c1-c1ccc(F)cc1]

$^1$H NMR (400 MHz, DMSO-d6) δ 8.81 (dd, J=6.1, 2.4 Hz, 1H), 7.94 (s, 1H), 7.84 (dd, J=9.8, 5.8 Hz, 1H), 7.71 (d, J=6.7 Hz, 1H), 7.61 (m, 1H), 7.47 (s, 2H), 7.27 (t, J=8.2 Hz, 3H), 7.14 (s, 1H), 5.77 (s, 1H), 5.03 (q, J=6.9 Hz, 1H), 1.30 (d, J=7.1 Hz, 3H).
m/z 419.

(S)-2,4-diamino-6-((1-(7-fluoro-3-(4-fluorophenyl)-4-oxo-4H-quinolizin-2-yl)ethyl)amino)pyrimidine-5-carbonitrile (Compound 37)

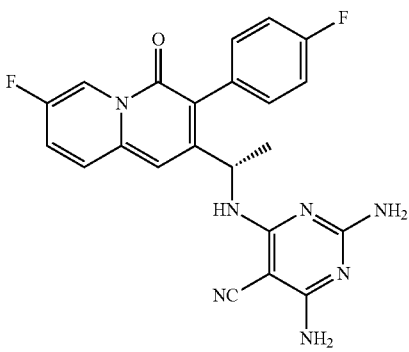 [SMILES: C[C@H](Nc1nc(N)nc(N)c1C#N)c1cc2ccc(F)cn2c(=O)c1-c1ccc(F)cc1]

$^1$H NMR (400 MHz, DMSO-d6) δ 8.82 (d, J=5.7 Hz, 1H), 7.85 (dd, J=9.6, 5.7 Hz, 1H), 7.62 (d, J=8.4 Hz, 1H), 7.29 (t, J=8.8 Hz, 2H), 7.10 (s, 1H), 7.00 (d, J=7.0 Hz, 1H), 6.57 (s, 2H), 5.10-5.02 (m, 1H), 1.19 (d, J=6.8 Hz, 3H).
m/z 434.

(S)-2-(1-((9H-purin-6-yl)amino)ethyl)-7-fluoro-3-(4-fluorophenyl)-4H-quinolizin-4-one (Compound 38)

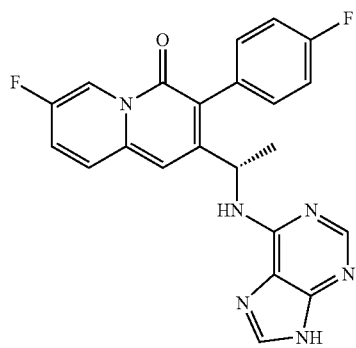 [SMILES: C[C@H](Nc1ncnc2[nH]cnc12)c1cc2ccc(F)cn2c(=O)c1-c1ccc(F)cc1]

$^1$H NMR (400 MHz, DMSO-d6) δ 12.95 (s, 1H), 8.93-8.51 (m, 1H), 8.34-8.02 (m, 4H), 7.77 (s, 1H), 7.57 (t, J=8.5 Hz, 1H), 7.31 (t, J=8.7 Hz, 2H), 7.16 (s, 1H), 5.19 (m, 1H), 1.35 (d, J=7.4 Hz, 3H).
m/z 419.

71

(S)-2-(1-((2-amino-9H-purin-6-yl)amino)ethyl)-7-fluoro-3-(4-fluorophenyl)-4H-quinolizin-4-one (Compound 39)

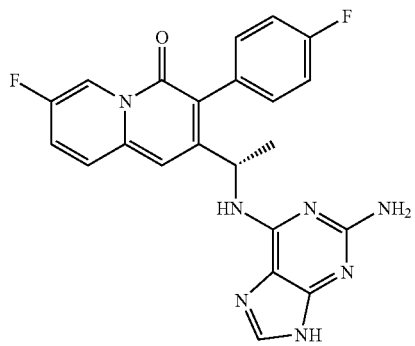 [SMILES: C[C@H](Nc1nc(N)nc2[nH]cnc12)c1cc2ccc(F)cn2c(=O)c1-c1ccc(F)cc1]

¹H NMR (400 MHz, DMSO-d6) δ 12.13 (s, 1H), 8.81 (dd, J=6.0, 2.4 Hz, 1H), 7.80-7.64 (m, 3H), 7.57 (m, 1H), 7.34 (s, 2H), 7.14 (s, 1H), 5.48 (s, 2H), 5.17 (m, 1H), 1.27 (d, J=7.0 Hz, 3H).

m/z 434.

(S)-7-fluoro-2-(1-((5-fluoro-7H-pyrrolo[2,3-d]pyrimidin-4-yl)amino)ethyl)-3-phenyl-4H-quinolizin-4-one (Compound 40)

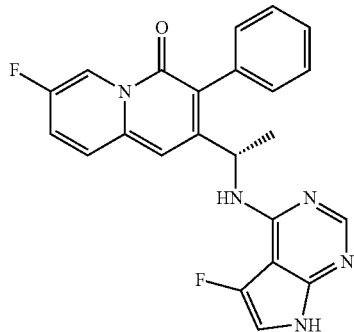 [SMILES: C[C@H](Nc1ncnc2[nH]cc(F)c12)c1cc2ccc(F)cn2c(=O)c1-c1ccccc1]

¹H NMR (400 MHz, DMSO-d6) δ 11.43 (s, 1H), 8.81 (dd, J=6.0, 2.5 Hz, 1H), 8.04 (s, 1H), 7.79 (dd, J=9.8, 5.8 Hz, 1H), 7.57 (m, 1H), 7.48 (t, J=7.4 Hz, 2H), 7.39 (d, J=7.6 Hz, 1H), 7.22 (s, 1H), 7.18 (d, J=6.6 Hz, 1H), 7.10 (d, J=2.6 Hz, 1H), 5.20 (q, J=7.0 Hz, 1H), 1.34 (d, J=7.0 Hz, 3H).

m/z 418.

72

4-Amino-6-((1-(7-fluoro-4-oxo-3-phenyl-4H-quinolizin-2-yl)propyl)amino)pyrimidine-5-carbonitrile (Compound 41)

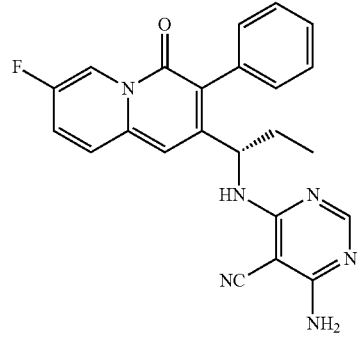

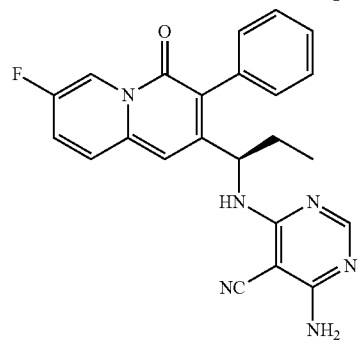

The racemic product was purified through chiral HPLC to obtain two fractions. The first-eluting enantiomer on CHIRALPAK IA column is 41a (RT-3.74) and the second-eluting enantiomer on CHIRALPAK IA column is 41b (RT-4.31).

41a: ¹H NMR (400 MHz, DMSO-d6) δ 8.81 (dd, J=6.0, 2.5 Hz, 1H), 7.93 (s, 1H), 7.80 (dd, J=9.8, 5.8 Hz, 1H), 7.66-7.55 (m, 2H), 7.41 (m, 4H), 7.25 (s, 2H), 7.14 (s, 1H), 5.00-4.88 (m, 1H), 1.86 (m, 1H), 1.56 (m, 1H), 0.68 (t, J=7.2 Hz, 3H).

m/z 415.

2,4-diamino-6-((1-(7-fluoro-4-oxo-3-phenyl-4H-quinolizin-2-yl)propyl)amino)pyrimidine-5-carbonitrile (Compound 42)

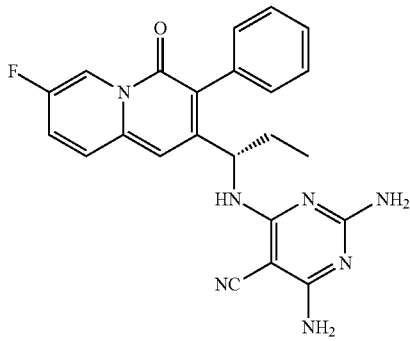

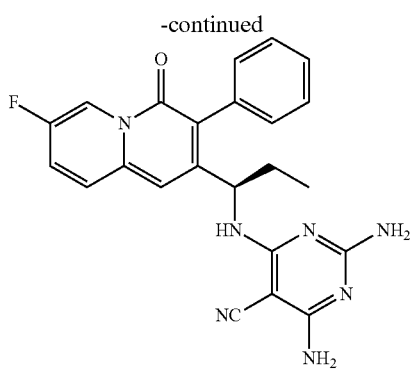

The racemic product was purified through chiral HPLC to obtain two fractions. The first-eluting enantiomer on CHIRALPAK IA column is 42a (RT-7.29) and the second-eluting enantiomer on CHIRALPAK IA column is 42b (RT-10.08).

42a: $^1$H NMR (400 MHz, DMSO-d6) δ 8.82 (dd, J=6.0, 2.4 Hz, 1H), 7.81 (dd, J=9.8, 5.7 Hz, 1H), 7.75-7.48 (m, 3H), 7.48-7.19 (m, 2H), 7.11 (s, 1H), 6.88 (d, J=7.6 Hz, 1H), 6.56 (s, 2H), 5.01-4.87 (m, 1H), 1.86-1.64 (m, 1H), 1.63-1.37 (m, 1H), 0.64 (t, J=7.2 Hz, 3H).

m/z 430.

2-(1-((9H-purin-6-yl)amino)propyl)-7-fluoro-3-phenyl-4H-quinolizin-4-one (Compound 43)

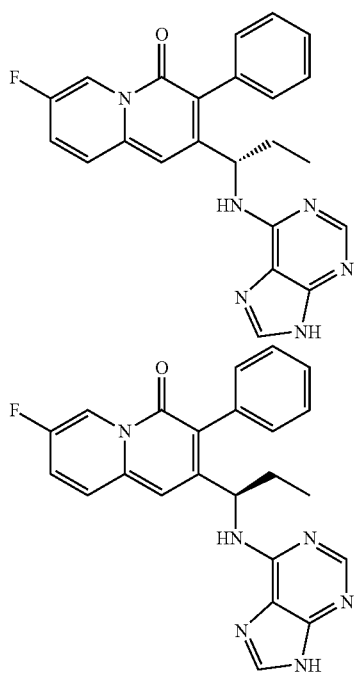

The racemic product was purified through chiral HPLC to obtain two fractions. The first-eluting enantiomer on Chiral PAK IA column is 43a (RT-3.95) and the second-eluting enantiomer on Chiral PAK IA column is 43b (RT-5.56).

43a: $^1$H NMR (400 MHz, DMSO-d6) δ 8.81 (dd, J=6.1, 2.4 Hz, 1H), 8.13 (s, 2H), 7.75 (s, 1H), 7.57 (d, J=7.4 Hz, 1H), 7.49 (t, J=7.4 Hz, 3H), 7.40 (d, J=7.7 Hz, 1H), 7.17 (s, 1H), 5.11 (m, 1H), 1.90 (m, 1H), 1.63 (m, 1H), 0.71 (t, J=7.3 Hz, 3H).

m/z 415.

4-Amino-6-((1-(7-fluoro-3-(3-fluorophenyl)-4-oxo-4H-quinolizin-2-yl)propyl)amino)pyrimidine-5-carbonitrile (Compound 44)

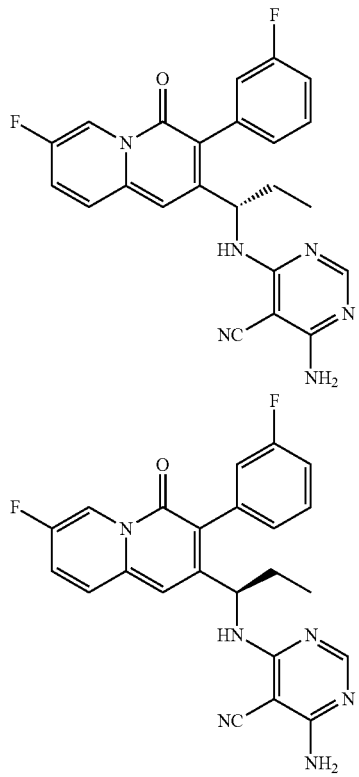

The racemic product was purified through chiral HPLC to obtain two fractions. The first-eluting enantiomer on CHIRALPAK IA column is 44a (RT-6.05) and the second-eluting enantiomer on CHIRALPAK IA column is 44b (RT-8.86).

44a: $^1$H NMR (400 MHz, DMSO-d$_6$) δ 8.82 (dd, J=6.2, 2.4 Hz, 1H), 7.92 (s, 1H), 7.82 (dd, J=9.8, 5.8 Hz, 1H), 7.63 (m, 2H), 7.49 (q, J=7.4 Hz, 1H), 7.37-7.11 (m, 5H), 4.92 (m, 1H), 1.88 (m, 1H), 1.59 (m, 1H), 0.70 (t, J=7.3 Hz, 3H).

m/z 433.

2,4-diamino-6-((1-(7-fluoro-3-(3-fluorophenyl)-4-oxo-4H-quinolizin-2-yl)propyl)amino)pyrimidine-5-carbonitrile (Compound 45)

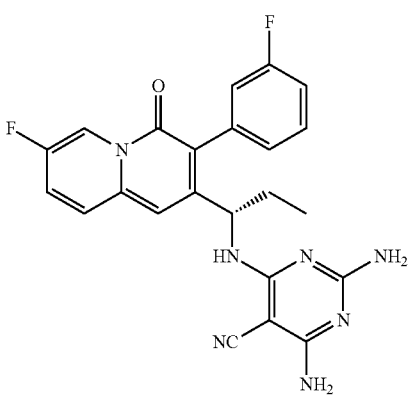

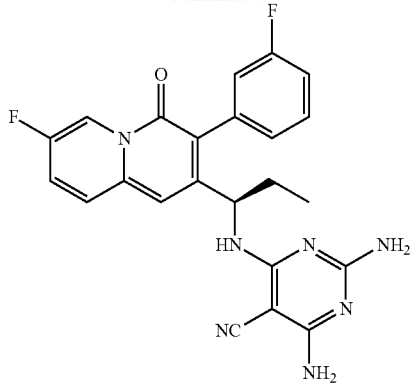

The racemic product was purified through chiral HPLC to obtain two fractions. The first-eluting enantiomer on CHIRALPAK IA column is 45a (RT-6.80) and the second-eluting enantiomer on CHIRALPAK IA column is 45b (RT-10.24).

45a: $^1$H NMR (400 MHz, DMSO-d6) δ 8.84 (dd, J=6.0, 2.5 Hz, 1H), 7.83 (dd, J=9.8, 5.7 Hz, 1H), 7.63 (m, 1H), 7.53 (q, J=7.4 Hz, 1H), 7.21 (m, 1H), 7.13 (s, 1H), 6.92 (d, J=7.5 Hz, 1H), 6.58 (s, 2H), 4.90 (m, 1H), 1.82-1.73 (m, 1H), 1.50 (m, 1H), 0.66 (t, J=7.2 Hz, 3H).

m/z 448.

2-(1-((9H-purin-6-yl)amino)propyl)-7-fluoro-3-(3-fluorophenyl)-4H-quinolizin-4-one (Compound 46)

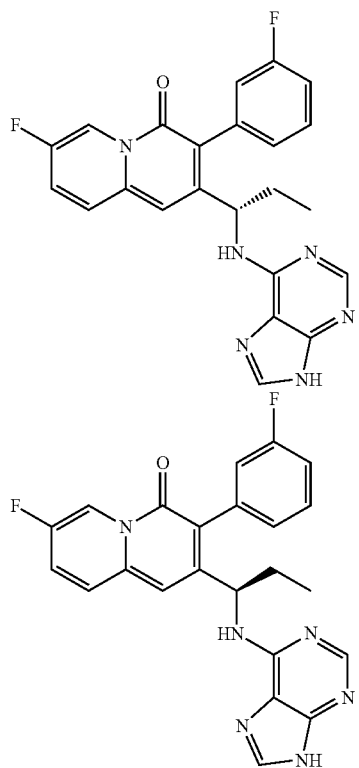

The racemic product was purified through chiral HPLC to obtain two fractions. The first-eluting enantiomer on Chiral IA column is 46a (RT-4.03) and the second-eluting enantiomer on Chiral IA column is 46b (RT-5.73).

46a: $^1$H NMR (400 MHz, DMSO-d6) δ 8.82 (dd, J=6.0, 2.4 Hz, 1H), 8.14 (d, J=12.8 Hz, 3H), 7.77 (s, 1H), 7.66-7.49 (m, 2H), 7.44-7.11 (m, 3H), 5.09 (m, 1H), 1.98-1.84 (m, 1H), 1.73-1.59 (m, 1H), 0.74 (t, J=7.3 Hz, 3H).

m/z 433.

2-(1-((2-amino-9H-purin-6-yl)amino)propyl)-7-fluoro-3-(3-fluorophenyl)-4H-quinolizin-4-one (Compound 47)

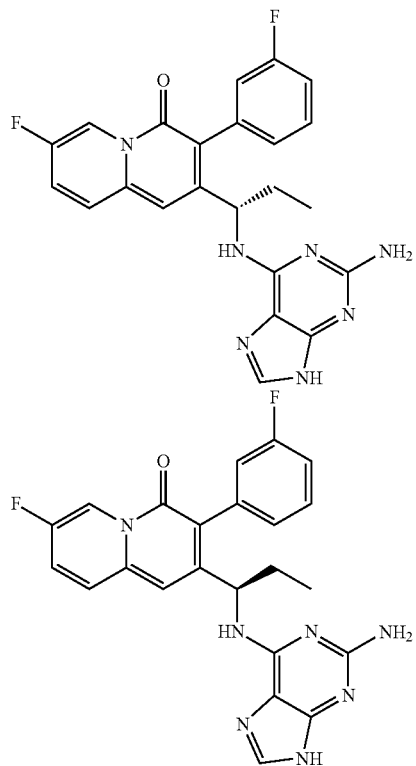

The racemic product was purified through chiral HPLC to obtain two fractions. The first-eluting enantiomer on Lux Cellulose-1 column is 47a (RT-5.61) and the second-eluting enantiomer on Lux Cellulose-1 column is 47b (RT-7.87).

47a: $^1$H NMR (400 MHz, DMSO-d6) δ 12.14 (s, 1H), 8.83 (dd, J=5.9, 2.4 Hz, 1H), 7.83-7.49 (m, 5H), 7.31-7.09 (m, 2H), 5.41 (s, 2H), 5.03 (m, 1H), 1.83 (m, 1H), 1.57 (m, 1H), 0.71 (t, J=7.2 Hz, 3H).

m/z 448.

(S)-4-amino-6-((1-(3-(3,5-difluorophenyl)-7-fluoro-4-oxo-4H-quinolizin-2-yl)ethyl)amino)pyrimidine-5-carbonitrile (Compound 48)

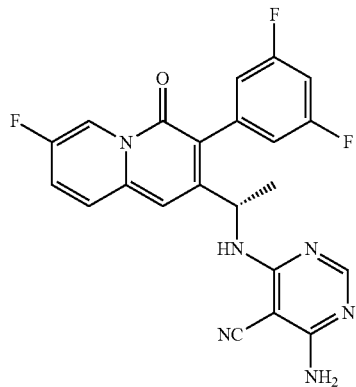 [SMILES: C[C@H](Nc1ncnc(N)c1C#N)c1cc2ccc(F)cn2c(=O)c1-c1cc(F)cc(F)c1]

¹H NMR (400 MHz, DMSO-d₆) δ 8.84 (dd, J=6.1, 2.5 Hz, 1H), 7.92 (s, 1H), 7.88 (dd, J=9.8, 5.7 Hz, 1H), 7.78-7.62 (m, 3H), 7.33-7.15 (m, 2H), 5.05 (q, J=6.9 Hz, 1H), 1.34 (d, J=7.0 Hz, 3H).

m/z 437.

(S)-2,4-diamino-6-((1-(3-(3,5-difluorophenyl)-7-fluoro-4-oxo-4H-quinolizin-2-yl)ethyl)amino)pyrimidine-5-carbonitrile (Compound 49)

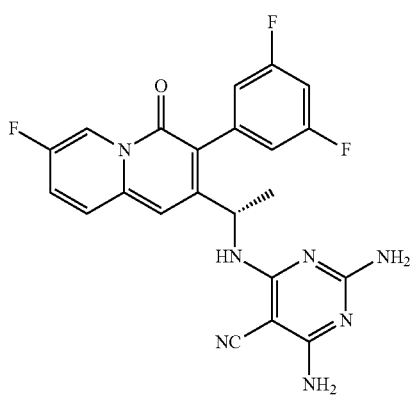 [SMILES: C[C@H](Nc1nc(N)nc(N)c1C#N)c1cc2ccc(F)cn2c(=O)c1-c1cc(F)cc(F)c1]

¹H NMR (400 MHz, DMSO-d₆) δ 8.85 (dd, J=5.9, 2.4 Hz, 1H), 7.90 (dd, J=9.8, 5.8 Hz, 1H), 7.67 (m, 1H), 7.30-7.19 (m, 2H), 7.16-6.96 (m, 2H), 6.67 (s, 1H), 5.02 (q, J=6.9 Hz, 1H), 1.25 (d, J=7.1 Hz, 3H).

m/z 452.

(S)-2-(1-((9H-purin-6-yl)amino)ethyl)-3-(3,5-difluorophenyl)-7-fluoro-4H-quinolizin-4-one (Compound 50)

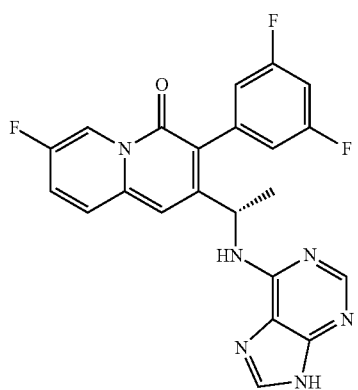 [SMILES: C[C@H](Nc1ncnc2[nH]cnc12)c1cc2ccc(F)cn2c(=O)c1-c1cc(F)cc(F)c1]

¹H NMR (400 MHz, DMSO-d₆) δ 12.97 (s, 1H), 8.83 (d, J=6.0 Hz, 1H), 8.29 (s, 1H), 8.13 (m, 2H), 7.86-7.77 (m, 1H), 7.66-7.58 (m, 1H), 7.28 (m, 3H), 7.19 (s, 1H), 5.20 (m, 1H), 1.38 (d, J=6.9 Hz, 3H).

m/z 437.

(S)-2-(1-((2-amino-9H-purin-6-yl)amino)ethyl)-3-(3,5-difluorophenyl)-7-fluoro-4H-quinolizin-4-one (Compound 51)

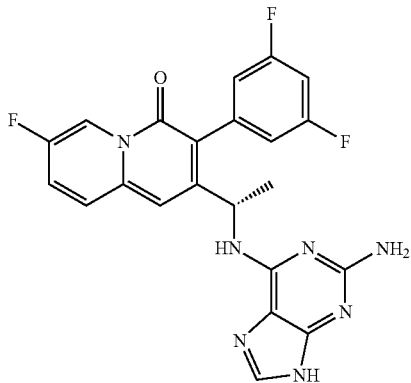 [SMILES: C[C@H](Nc1nc(N)nc2[nH]cnc12)c1cc2ccc(F)cn2c(=O)c1-c1cc(F)cc(F)c1]

¹H NMR (400 MHz, DMSO-d₆) δ 12.17 (s, 1H), 8.84 (dd, J=6.1, 2.4 Hz, 1H), 8.26 (s, 1H), 7.88-7.78 (m, 1H), 7.72 (s, 2H), 7.63 (dd, J=10.1, 7.6 Hz, 1H), 7.23 (m, 3H), 5.14 (m, 1H), 1.31 (d, J=7.0 Hz, 3H).

m/z 452.

(S)-7-fluoro-3-phenyl-2-(1-(thiazolo[5,4-d]pyrimidin-7-ylamino)ethyl)-4H-quinolizin-4-one (Compound 52)

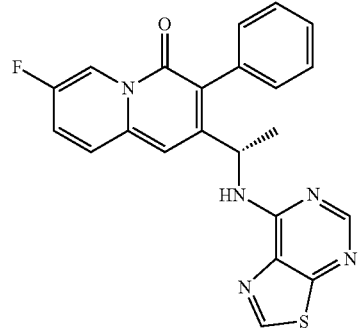 [SMILES: C[C@H](Nc1ncnc2scnc12)c1cc2ccc(F)cn2c(=O)c1-c1ccccc1]

¹H NMR (400 MHz, DMSO-d6) δ 9.31 (s, 1H), 8.85-8.77 (m, 2H), 8.35 (s, 1H), 7.78 (dd, J=9.8, 5.8 Hz, 1H), 7.57 (m, 2H), 7.49 (t, J=7.3 Hz, 2H), 7.40 (d, J=7.5 Hz, 1H), 7.17 (s, 1H), 5.25 (q, J=7.1 Hz, 1H), 1.39 (d, J=7.1 Hz, 3H).

m/z 418.

(S)-2-amino-4-chloro-6-((1-(7-fluoro-4-oxo-3-phenyl-4H-quinolizin-2-yl)ethyl)amino)pyrimidine-5-carbonitrile (Compound 53)

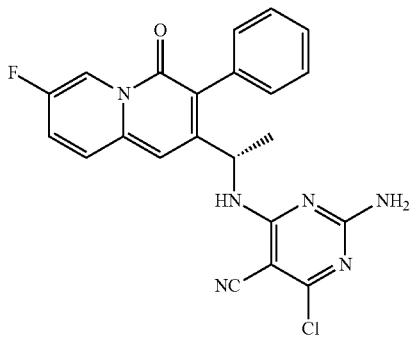 [SMILES: C[C@H](Nc1nc(N)nc(Cl)c1C#N)c1cc2ccc(F)cn2c(=O)c1-c1ccccc1]

¹H NMR (400 MHz, DMSO-d6) δ 8.84 (dd, J=6.1, 2.5 Hz, 1H), 7.99-7.86 (m, 2H), 7.68-7.58 (m, 2H), 7.46 (t, J=7.4 Hz, 2H), 7.38-7.32 (m, 1H), 7.09 (s, 1H), 6.96 (s, 1H), 5.77 (s, 1H), 5.11 (q, J=7.0 Hz, 1H), 1.23 (d, J=7.0 Hz, 3H).

m/z 435, 437.

(S)-7-fluoro-3-phenyl-2-(1-(pyrido[3,2-d]pyrimidin-4-ylamino)ethyl)-4H-quinolizin-4-one (Compound 54)

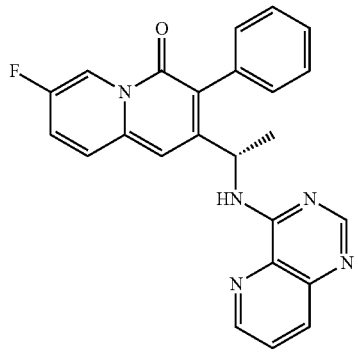 [SMILES: C[C@H](Nc1ncnc2cccnc12)c1cc2ccc(F)cn2c(=O)c1-c1ccccc1]

¹H NMR (400 MHz, DMSO-d6) δ 8.95-8.75 (m, 3H), 8.44 (s, 1H), 8.12 (dd, J=8.5, 1.6 Hz, 1H), 7.86 (dd, J=8.5, 4.3 Hz, 1H), 7.77 (dd, J=9.8, 5.8 Hz, 1H), 7.62-7.36 (m, 5H), 7.22 (s, 1H), 5.28 (q, J=7.0 Hz, 1H), 1.44 (d, J=7.0 Hz, 3H).

m/z 412.

Example 12: Preparation of (S)-4-amino-6-((1-(7-fluoro-4-oxo-3-phenyl-4H-quinolizin-2-yl)ethyl)amino)-pyrimidine-5-carbonitrile (Compound 14a)

To a stirred solution of (S)-2-(1-aminoethyl)-7-fluoro-3-phenyl-4H-quinolizin-4-one (7.0 g, 24.80 mmol) and 4-amino-6-chloropyrimidine-5-carbonitrile (3.83 g, 24.80 mmol) in DMF (75 mL) was added DIPEA (6.50 mL, 37.2 mmol) at room temperature. The reaction mixture was then heated at 80° C. for 8 h. The reaction mixture was poured into ice-water and the solid precipitated was filtered and dried under high vacuum. The solid was then dissolved in ethyl acetate (500 mL) and the so formed solution was concentrated slowly on rotary evaporator till a volume remaining in the flask was 100 mL. The solid formed in the flask was filtered and dried under high vacuum to obtain 6.4 g of (S)-4-amino-6-((1-(7-fluoro-4-oxo-3-phenyl-4H-quinolizin-2-yl)ethyl)amino)-pyrimidine-5-carbonitrile. The product was also recovered from the filtrate by concentrating it and purifying the residue by flash chromatography, and further crystallization using ethyl acetate. The combined yield of (S)-4-amino-6-((1-(7-fluoro-4-oxo-3-phenyl-4H-quinolizin-2-yl)ethyl)amino)-pyrimidine-5-carbonitrile (compound 14a) was 7.4 g (74.5%).

¹H NMR (400 MHz, DMSO-d6) δ 8.80 (dd, J=6.0, 2.5 Hz, 1H), 7.93 (s, 1H), 7.83 (m, 1H), 7.68 (d, J=6.7 Hz, 1H), 7.59 (m, 1H), 7.49-7.32 (m, 4H), 7.25 (s, 2H), 7.13 (d, J=3.1 Hz, 1H), 5.06 (m, 1H), 1.27 (d, J=6.7 Hz, 3H).

m/z 401.

Example 13: 2-((4-Amino-1H-pyrazolo[3,4-d]pyrimidin-1-yl)methyl)-6-methyl-3-phenyl-4H-quinolizin-4-one (Compound 55)

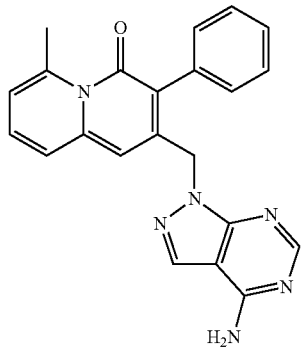 [SMILES: Cc1cccc2cc(Cn3ncc4c(N)ncnc43)c(-c3ccccc3)c(=O)n12]

A stirred solution of 2-(Hydroxymethyl)-6-methyl-3-phenyl-4H-quinolizin-4-one (100 mg, 0.377 mmol) and TEA (0.105 mL, 0.754 mmol) in DCM was cooled to 0° C., to which was then added MeSO₂Cl (0.044 mL, 0.565 mmol) and stirred at 0° C. for 30 minutes. The reaction mixture was quenched with cold water and extracted with DCM (2×25 mL), the combined organic layer was washed with water (2×25 mL), dried over anhydrous Na₂SO₄, filtered and concentrated under reduced pressure to obtain a residue. The residue was dissolved in DMF (5 mL) and to which was added Cs₂CO₃ (184 mg, 0.565 mmol) and 1H-pyrazolo[3,4-d]pyrimidin-4-amine (61.1 mg, 0.452 mmol). The reaction mixture was then heated at 85° C. for 2 h, and then it was concentrated under reduced pressure to obtain crude product. The crude product was then purified by preparative HPLC to obtain 2-((4-Amino-1H-pyrazolo[3,4-d]pyrimidin-1-yl)methyl)-6-methyl-3-phenyl-4H-quinolizin-4-one (Compound 55) in 24% yield.

¹H NMR (400 MHz, Chloroform-δ 8.28 (s, 1H), 8.23 (s, 1H), 7.44-7.29 (m, 7H), 7.01 (m, 2H), 6.50 (d, J=6.7 Hz, 1H), 6.04 (s, 1H), 5.41 (s, 2H), 2.99 (s, 3H).

m/z 383.

Example 14

The following compounds were prepared using the process described in above example 13 with appropriate starting materials/intermediates and under appropriate reaction conditions.

2-((6-Amino-9H-purin-9-yl)methyl)-3-phenyl-4H-quinolizin-4-one (Compound 56)

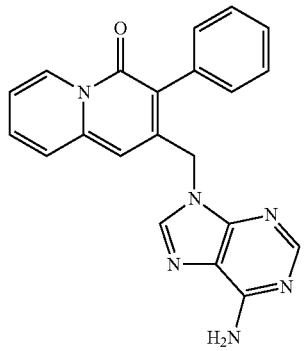 [SMILES: Nc1ncnc2c1ncn2Cc1cc2ccccn2c(=O)c1-c1ccccc1]

¹H NMR (400 MHz, DMSO-d6) δ 8.95 (m, 1H), 8.07 (s, 1H), 7.99 (s, 1H), 7.69 (m, 1H), 7.51-7.35 (m, 6H), 7.27 (s, 2H), 7.19 (m, 1H), 6.28 (s, 1H), 5.23 (s, 2H).

m/z 369.

2-(1-(4-Amino-1H-pyrazolo[3,4-d]pyrimidin-1-yl)ethyl)-3-(3-fluorophenyl)-6-methyl-4H-quinolizin-4-one (Compound 57)

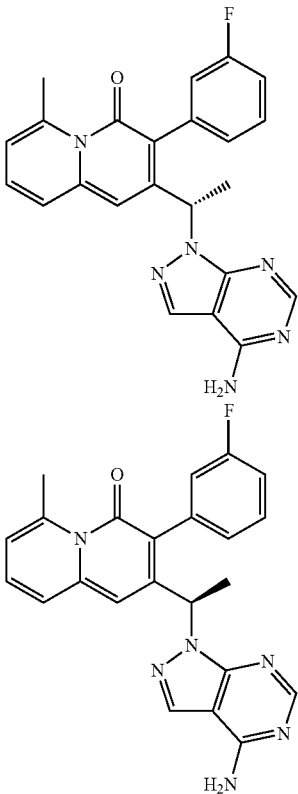

The racemic product was purified through chiral HPLC to obtain two fractions. The first-eluting enantiomer on Chiral IA column is 57a (RT-4.37) and the second-eluting enantiomer on Chiral IA column is 57b (RT-6.63).

57a: $^1$H NMR (400 MHz, Chloroform-δ 8.29 (s, 1H), 7.98 (s, 1H), 7.40 (d, J=7.5 Hz, 1H), 7.19 (d, J=7.6 Hz, 1H), 7.15-7.08 (m, 2H), 7.07-6.95 (m, 2H), 6.56 (s, 1H), 6.47 (m, 1H), 6.04 (q, J=7.1 Hz, 1H), 5.59 (s, 2H), 2.97 (s, 3H), 1.81 (d, J=7.1 Hz, 3H).

m/z 415.

Example 15: N-(3-(4-amino-1-(1-(7-fluoro-4-oxo-3-phenyl-4H-quinolizin-2-yl)ethyl)-1H-pyrazolo[3,4-d]pyrimidin-3-yl)-5-fluorophenyl)methanesulfonamide (Compound 58)

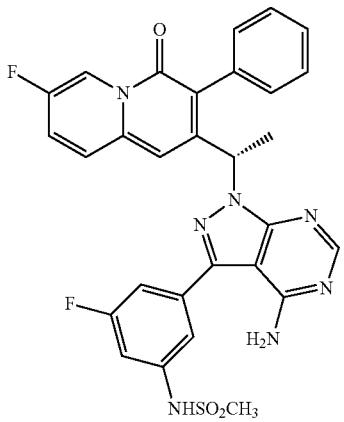

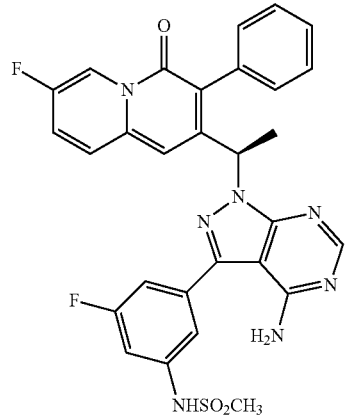

To a stirred solution of 7-fluoro-2-(1-hydroxyethyl)-3-phenyl-4H-quinolizin-4-one (0.450 g, 1.588 mmol), 3-iodo-1H-pyrazolo[3,4-d]pyrimidin-4-amine (0.415 g, 1.588 mmol), and triphenylphosphine (0.625 g, 2.383 mmol) in THF (15 ml) was added diisopropylazodicarboxylate (0.463 ml, 2.383 mmol) dropwise at 45° C. The resulting mixture was stirred at 45° C. for 26 h. The reaction mixture was quenched with water, extracted with ethyl acetate (3×50 mL), the combined organic layer was dried over Na$_2$SO$_4$, filtered and concentrated under reduced pressure to yield the crude product. The crude product was purified by flash column chromatography using 70% ethyl acetate-hexane as an eluent to obtain 2-(1-(4-amino-3-iodo-1H-pyrazolo[3,4-d]pyrimidin-1-yl)ethyl)-7-fluoro-3-phenyl-4H-quinolizin-4-one (0.430 g, 51.4% yield).

A stirred mixture of 2-(1-(4-amino-3-iodo-1H-pyrazolo[3,4-d]pyrimidin-1-yl)ethyl)-7-fluoro-3-phenyl-4H-quinolizin-4-one (0.350 g, 0.665 mmol), N-(3-fluoro-5-(4,4,5,5-tetramethyl-1,3,2-dioxaborolan-2-yl)phenyl)methanesulfonamide (0.524 g, 1.663 mmol), Na$_2$CO$_3$ (0.998 ml, 1.995 mmol), PdCl$_2$ (dppf) (0.073 g, 0.100 mmol) and DMF (3 mL) was heated at 120° C. for 4 h. The reaction mixture was then poured into water, a solid product precipitated was filtered, dried and purified by flash column chromatography using 80% ethyl acetate-hexane as an eluent to yield racemic N-(3-(4-amino-1-(1-(7-fluoro-4-oxo-3-phenyl-4H-quinolizin-2-yl)ethyl)-1H-pyrazolo[3,4-d]pyrimidin-3-yl)-5-fluorophenyl)methanesulfonamide (Compound 58) in 64% yield.

The racemic product was purified through chiral HPLC to obtain two fractions. The first-eluting enantiomer on CHIRALPAK IA column is 58a (RT-5.26) and the second-eluting enantiomer on CHIRALPAK IA column is 58b (RT-6.67).

58a: $^1$H NMR (400 MHz, DMSO-d6) δ 8.84 (dd, J=6.0, 2.4 Hz, 1H), 8.16 (s, 1H), 7.92 (dd, J=9.8, 5.8 Hz, 1H), 7.64 (m, 1H), 7.60-7.19 (m, 7H), 7.09 (dd, J=10.8, 2.2 Hz, 1H), 6.93 (s, 1H), 6.03 (q, J=7.0 Hz, 1H), 3.11 (s, 3H), 1.74 (d, J=7.1 Hz, 3H).

m/z 588.

Example 16

The following compounds were prepared using the process described in Example 15 with appropriate starting materials/intermediates and under appropriate reaction conditions.

2-(1-(4-amino-3-(3-fluoro-5-hydroxyphenyl)-1H-pyrazolo[3,4-d]pyrimidin-1-yl)ethyl)-7-fluoro-3-phenyl-4H-quinolizin-4-one (Compound 59)

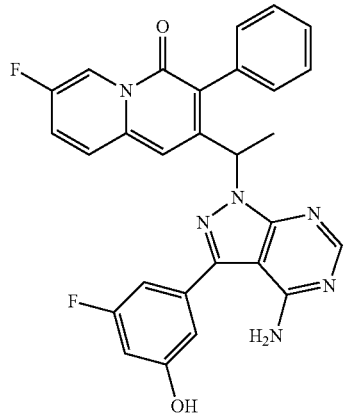 [SMILES: CC(c1cc2ccc(F)cn2c(=O)c1-c1ccccc1)n1nc(-c2cc(O)cc(F)c2)c2c(N)ncnc21]

$^1$H NMR (400 MHz, DMSO-d6) δ 10.23 (s, 1H), 8.84 (dd, J=6.1, 2.4 Hz, 1H), 8.16 (s, 1H), 7.93 (dd, J=9.8, 5.8 Hz, 1H), 7.63 (m, 1H), 7.42 (m, 5H), 6.98 (d, J=7.2 Hz, 2H), 6.89 (s, 1H), 6.69 (m, 1H), 6.02 (q, J=7.4 Hz, 1H), 1.74 (d, J=7.1 Hz, 3H).

m/z 511.

2-(1-(4-amino-3-(4-fluoro-3-hydroxyphenyl)-1H-pyrazolo[3,4-d]pyrimidin-1-yl)ethyl)-7-fluoro-3-phenyl-4H-quinolizin-4-one (Compound 61)

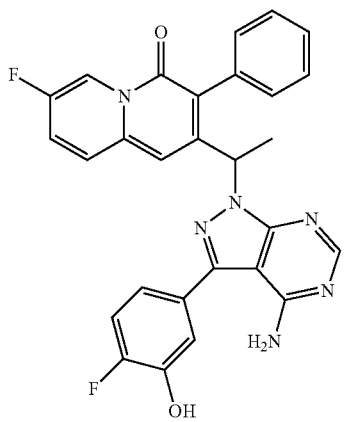

$^1$H NMR (400 MHz, DMSO-d6) δ 8.83 (dd, J=5.9, 2.4 Hz, 1H), 8.14 (s, 1H), 7.91 (dd, J=9.8, 5.8 Hz, 1H), 7.76-7.24 (m, 8H), 7.13 (m, 1H), 6.90 (s, 1H), 6.01 (q, J=7.0 Hz, 1H), 1.73 (d, J=7.1 Hz, 3H).

m/z 511.

2-(1-(4-amino-3-(3-fluoro-4-hydroxyphenyl)-1H-pyrazolo[3,4-d]pyrimidin-1-yl)ethyl)-7-fluoro-3-phenyl-4H-quinolizin-4-one (Compound 60)

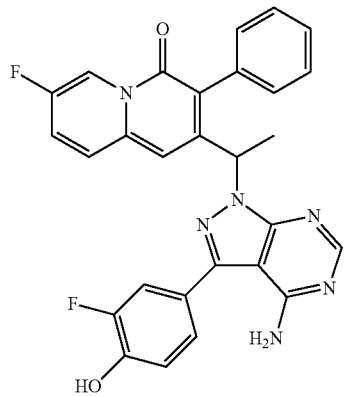 [SMILES: CC(c1cc2ccc(F)cn2c(=O)c1-c1ccccc1)n1nc(-c2ccc(O)c(F)c2)c2c(N)ncnc21]

$^1$H NMR (400 MHz, DMSO-d6) δ 10.24 (s, 1H), 8.82 (dd, J=5.9, 2.5 Hz, 1H), 8.14 (s, 1H), 7.94 (dd, J=9.8, 5.8 Hz, 1H), 7.61 (m, 1H), 7.48 (m, 7H), 7.41-7.32 (m, 2H), 7.12 (t, J=8.7 Hz, 1H), 6.90 (s, 1H), 5.99 (q, J=6.8 Hz, 1H), 1.72 (d, J=7.1 Hz, 3H).

m/z 511.

2-(1-(4-amino-3-(3-hydroxyphenyl)-1H-pyrazolo[3,4-d]pyrimidin-1-yl)ethyl)-7-fluoro-3-phenyl-4H-quinolizin-4-one (Compound 62)

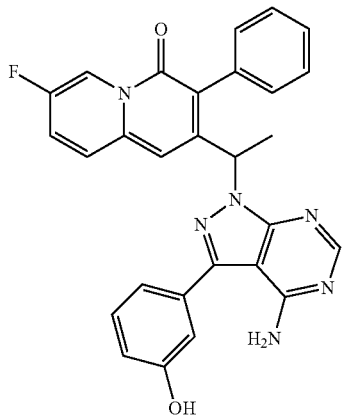 [SMILES: CC(c1cc2ccc(F)cn2c(=O)c1-c1ccccc1)n1nc(-c2cccc(O)c2)c2c(N)ncnc21]

$^1$H NMR (400 MHz, DMSO-d6) δ 9.77 (s, 1H), 8.84 (d, J=5.8 Hz, 1H), 8.16 (s, 1H), 7.91 (dd, J=9.8, 5.8 Hz, 1H), 7.80-7.25 (m, 7H), 7.15 (d, J=10.4 Hz, 2H), 6.91 (d, J=9.1 Hz, 2H), 6.02 (q, J=7.0 Hz, 1H), 5.77 (s, 2H), 1.75 (d, J=7.0 Hz, 3H).

m/z 493.

2-(1-(4-amino-5-(3-fluoro-5-hydroxyphenyl)-7H-pyrrolo[2,3-d]pyrimidin-7-yl)ethyl)-7-fluoro-3-phenyl-4H-quinolizin-4-one (Compound 63)

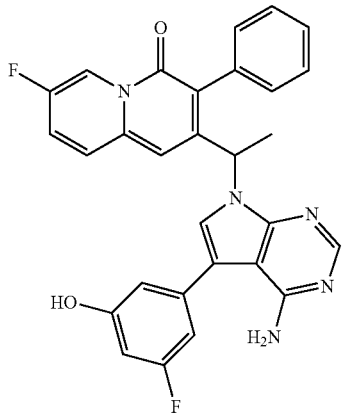 [SMILES: CC(c1cc2ccc(F)cn2c(=O)c1-c1ccccc1)n1cc(-c2cc(O)cc(F)c2)c2c(N)ncnc21]

$^1$H NMR (400 MHz, DMSO-d6) δ 10.09 (d, J=0.9 Hz, 1H), 8.84 (dd, J=6.0, 2.5 Hz, 1H), 8.05 (s, 1H), 7.86 (dd, J=9.8, 5.8 Hz, 1H), 7.75-7.51 (m, 2H), 7.44 (s, 4H), 7.37 (d, J=8.0 Hz, 1H), 6.81 (m, 1H), 6.76 (d, J=2.3 Hz, 2H), 6.55 (m, 1H), 6.24 (s, 2H), 5.88 (q, J=7.1 Hz, 1H), 1.66 (d, J=7.2 Hz, 3H).

m/z 510.

2-(1-(4-amino-3-(6-methoxypyridin-3-yl)-1H-pyrazolo[3,4-d]pyrimidin-1-yl)ethyl)-7-fluoro-3-phenyl-4H-quinolizin-4-one (Compound 64)

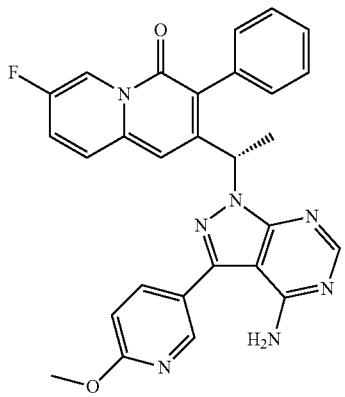 [SMILES: C[C@@H](c1cc2ccc(F)cn2c(=O)c1-c1ccccc1)n1nc(-c2ccc(O)nc2)c2c(N)ncnc21]

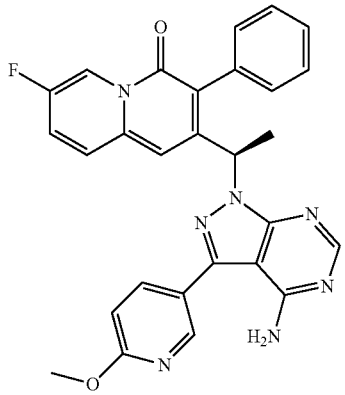

The racemic product was purified through chiral HPLC to obtain two fractions. The first-eluting enantiomer on CHIRALPAK IA column is 64a (RT-5.03) and the second-eluting enantiomer on CHIRALPAK IA column is 64b (RT-7.28).

64a: $^1$H NMR (400 MHz, DMSO-d6) δ 8.82 (dd, J=5.9, 2.5 Hz, 1H), 8.50 (d, J=2.4 Hz, 1H), 8.16 (s, 1H), 8.03 (dd, J=8.5, 2.5 Hz, 1H), 7.95 (dd, J=9.8, 5.8 Hz, 1H), 7.62 (m, 1H), 7.44 (m, 7H), 7.00 (d, J=8.6 Hz, 1H), 6.93 (s, 1H), 6.02 (q, J=6.9 Hz, 1H), 3.95 (s, 3H), 1.73 (d, J=7.1 Hz, 3H).

m/z 508.

2-(1-(4-amino-3-(2-oxoindolin-5-yl)-1H-pyrazolo[3,4-d]pyrimidin-1-yl)ethyl)-7-fluoro-3-phenyl-4H-quinolizin-4-one (Compound 65)

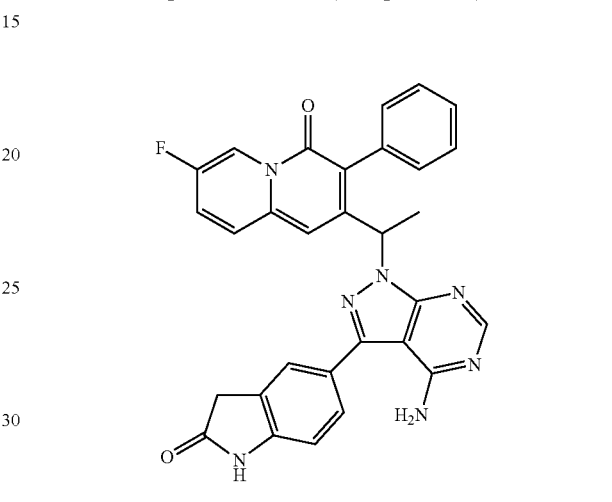

$^1$H NMR (400 MHz, DMSO-d6) δ 10.60 (s, 1H), 8.83 (d, J=5.5 Hz, 1H), 8.14 (s, 1H), 7.92 (dd, J=9.8, 5.8 Hz, 2H), 7.65-7.57 (m, 3H), 7.53 (d, J=8.1 Hz, 1H), 7.49-7.37 (m, 5H), 7.00 (d, J=8.0 Hz, 1H), 6.92 (s, 1H), 6.01 (q, J=7.0 Hz, 1H), 3.60 (s, 2H), 1.73 (d, J=7.1 Hz, 3H).

m/z 532.

(S)-2-(1-(4-amino-3-(6-hydroxypyridin-3-yl)-1H-pyrazolo[3,4-d]pyrimidin-1-yl)ethyl)-7-fluoro-3-phenyl-4H-quinolizin-4-one (Compound 66)

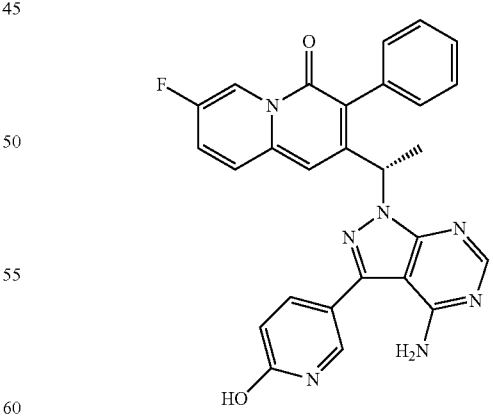

$^1$H NMR (400 MHz, DMSO-d6) δ 11.87 (s, 1H), 8.85-8.81 (m, 1H), 8.13 (s, 1H), 7.93 (dd, J=9.9, 5.8 Hz, 1H), 7.81 (dd, J=9.5, 2.6 Hz, 1H), 7.66-7.58 (m, 2H), 7.52-7.35 (m, 5H), 6.88 (s, 1H), 6.49 (d, J=9.5 Hz, 1H), 5.98 (q, J=7.1 Hz, 1H), 1.71 (d, J=7.1 Hz, 3H).

m/z 494.

N-(5-(4-amino-1-(1-(7-fluoro-4-oxo-3-phenyl-4H-quinolizin-2-yl)ethyl)-1H-pyrazolo[3,4-d]pyrimidin-3-yl)-2-methoxypyridin-3-yl)methanesulfonamide (Compound 67)

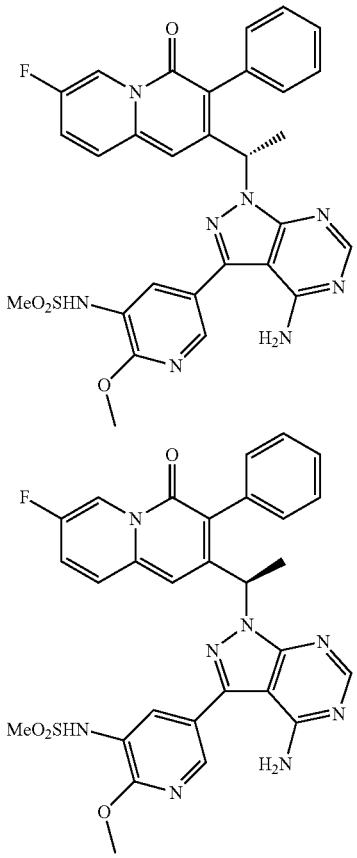

The racemic product was purified through chiral HPLC to obtain two fractions. The first-eluting enantiomer on Chiral PAK ID column is 67a (RT-4.04) and the second-eluting enantiomer on Chiral PAK ID column is 67b (RT-4.75).

67a: $^1$H NMR (400 MHz, DMSO-d6) δ 8.83 (dd, J=6.0, 2.4 Hz, 1H), 8.27 (d, J=2.1 Hz, 1H), 8.16 (s, 1H), 7.95-7.87 (m, 2H), 7.63 (m, 1H), 7.53-7.35 (m, 5H), 6.95 (s, 1H), 6.02 (q, J=7.1 Hz, 1H), 4.00 (s, 3H), 3.08 (s, 3H), 1.75 (d, J=7.1 Hz, 3H).

m/z 601.

(S)—N-(5-(4-amino-1-(1-(7-fluoro-4-oxo-3-phenyl-4H-quinolizin-2-yl)ethyl)-1H-pyrazolo[3,4-d]pyrimidin-3-yl)-2-hydroxypyridin-3-yl)methanesulfonamide (Compound 68)

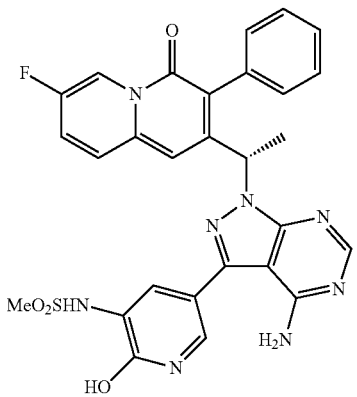

$^1$H NMR (400 MHz, DMSO-d6) δ 12.29 (s, 1H), 8.98 (s, 1H), 8.85-8.81 (m, 1H), 8.14 (s, 1H), 7.89-7.85 (m, 1H), 7.69-7.61 (m, 2H), 7.51-7.36 (m, 5H), 6.92 (d, J=9.5 Hz, 1H), 5.99 (q, J=7.1 Hz, 1H), 3.14 (s, 3H), 1.72 (d, J=7.1 Hz, 3H).

m/z 587.

2-(1-(4-amino-3-(3-fluoro-5-(hydroxymethyl)phenyl)-1H-pyrazolo[3,4-d]pyrimidin-1-yl)ethyl)-7-fluoro-3-phenyl-4H-quinolizin-4-one (Compound 69)

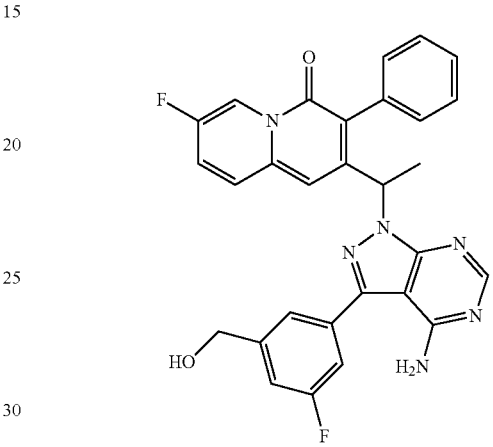

$^1$H NMR (400 MHz, DMSO-d6) δ 8.83 (d, J=5.7 Hz, 1H), 8.17 (s, 1H), 7.93 (dd, J=9.9, 5.8 Hz, 1H), 7.86-7.32 (m, 8H), 7.27 (d, J=9.8 Hz, 1H), 6.89 (s, 1H), 6.03 (q, J=7.1 Hz, 1H), 5.47 (s, 1H), 4.64 (s, 2H), 1.74 (d, J=7.1 Hz, 3H).

m/z 525.

Example 17: Identification of PI3K Inhibitors

A) Cell Based Assay for PI3Kα and PI3Kβ

Inhibition of PI3K activity was assessed using cell based assay. MDA-MB-453 cell line harboring PI3Kα activating mutation and 786-0 cells having constitutive expression of PI3Kβ were used for analyzing the inhibition of PI3Kα and PI3Kβ respectively. Cells were seeded in 96-well clear bottom plate at a density of 40000 cells/well and incubated overnight at 37° C. and 5% CO$_2$. Cells were then supplemented with complete medium and were treated with compounds for 1 h at 37° C. and 5% CO$_2$. To evaluate the effect of compound treatment on PI3K activity, AlphaScreen® SureFire® Cell-based Assay (Perkin-Elmer, Waltham, Mass., USA) was performed as per manufacturer's instruction. Cell culture medium was removed and cells were washed twice with PBS. Cells were lysed with 20 μL of 2× lysis buffer at ambient temperature for 10 min. 5 μl of acceptor beads were added to 384 well Proxiplate plate (Perkin Elmer Life Science, USA). 4 μL of lysate was added to the 384-well Proxiplate. After 2 h of incubation at ambient temperature, 2 μL of streptavidin coated donor beads were added. Relative luciferase units were measured in Pherastar microplate reader (BMG Labtech, Germany) at 520-620 nm. PI3K inhibition by compounds was calculated as indicated below:

% Inhibition =

$$100 - \frac{RLU \text{ of compound} - RLU \text{ of lysis buffer blank}}{RLU \text{ of control cells} - RLU \text{ of lysis buffer blank}} \times 100$$

B) Cell Based Assay for PI3Kγ

Raw 264.7 cells were maintained in DMEM (Sigma) supplemented with 10% fetal bovine serum (heat inactivated) (FBS, Sigma), 100 U penicillin/mL, and 100 μg/mL streptomycin and incubated at 37° C. and 5% $CO_2$. Cells were harvested by detachment with trypsin-EDTA, centrifuged and resuspended in complete medium. Cells were seeded at a density of 40000 cells/well in complete medium (100 μL/well) into 96-well clear bottom plates and incubated for 1 day at 37° C., 5% $CO_2$. Next day, the medium was removed by gentle aspiration and replaced with 100 μL medium without serum and incubated for 1 h at 37° C., 5% $CO_2$. Media was removed by gentle aspiration and 30 μL of serially diluted compounds in DMSO were added with an additional incubation of 1 h at 37° C., 5% $CO_2$. Cells were then stimulated with 30 μL complement component C5a (10 nM) for 3 min followed by washing with 50 μL/well PBS. After stimulation, cells were lysed with 20 μL of 2× lysis buffer and the plate was shaken on an orbital plate shaker at approximately 300 rpm for 10 min. AlphaScreen® SureFire® Cell-based Assay (Perkin-Elmer, Waltham, Mass., USA) was performed to measure phosphorylation of AKT, in the cells according to the manufacturer's instructions. The luminescence was measured using an alpha technology-compatible plate reader BMG Labtech, Germany) at 520-620 nm. Percentage inhibition was calculated according to formula:

$$100 - \frac{[(RLU \text{ of compound} - RLU \text{ of lysis buffer blank}) - (RLU \text{ of control cells} - RLU \text{ of lysis buffer blank})]}{[(RLU \text{ of DMSO control} - RLU \text{ of lysis buffer blank}) - (RLU \text{ of control cells} - RLU \text{ of lysis buffer blank})]} \times 100$$

C) Cell Based Assay for PI3Kδ

Raji cells were maintained in RPMI-1640 (Sigma) supplemented with 10% fetal bovine serum (heat inactivated) (FBS, Sigma), 100 U penicillin/mL, and 100 ng/mL streptomycin and incubated at 37° C. and 5% $CO_2$. Cells were centrifuged and resuspended in a complete medium. The required numbers of cells were transferred to a tissue culture flask containing medium without serum for 1 h at 37° C., 5% $CO_2$. Following 1 h serum starvation, cells were centrifuged and resuspended in Hank's Balanced Salt Solution (HBSS, Sigma) and seeded in at a density of 1 million cells/well in 96-well clear bottom plates. The cells were treated with test compounds for 1 h at 37° C., 5% $CO_2$. Cells were then stimulated with anti-IgM (3 μg/mL) for 30 min. After Stimulation, cells were lysed with 15 μL of 5× lysis buffer and the plate was shaken on an orbital plate shaker at approximately 300 rpm for 10 min. AlphaScreen® SureFire® Cell-based Assay (Perkin-Elmer, Waltham, Mass., USA) was performed to measure phosphorylation of AKT, in the cells according to the manufacturer's instructions. The luminescence was measured using an alpha technology-compatible plate reader BMG Labtech, Germany) at 520-620 nm. Percentage inhibition was calculated according to formula:

$$100 - \frac{[(RLU \text{ of compound} - RLU \text{ of lysis buffer blank}) - (RLU \text{ of control cells} - RLU \text{ of lysis buffer blank})]}{[(RLU \text{ of DMSO control} - RLU \text{ of lysis buffer blank}) - (RLU \text{ of control cells} - RLU \text{ of lysis buffer blank})]} \times 100$$

$IC_{50}$ values were calculated by plotting % inhibition against the respective concentrations of test compounds using GraphPad Prism 5.

PI3Kδ inhibition $IC_{50}$ of the compounds of invention is provided in Table 1 below: Compounds with $IC_{50}$ between 0.1 nM and 10 nM are grouped under group A, compounds with $IC_{50}$ between 11 nM and 50 nM are grouped under group B, and compounds with $IC_{50}$ between 51 nM and 250 nM are grouped under group C.

TABLE 1

| Group | Compound Nos. |
|---|---|
| A | 2a, 6a, 7a, 8a, 9a, 10a, 11a, 12a, 13a, 16a, 17a, 18a, 21a, 22a, 23a, 24a, 25, 26, 27, 28, 30, 32, 33, 40, 42a, 45a, 48, 49, 52, 53, 54, 59, 61, 62, 63, and 67a. |
| B | 4a, 14a, 15a, 19a, 20a, 29, 31, 34, 36, 41a, 44a, 47b, 50, 51, 58a, 60, and 64a. |
| C | 5a, and 65. |

The invention claimed is:

1. A compound of the general formula (I), its tautomeric form, its stereoisomer, or its pharmaceutically acceptable salt,

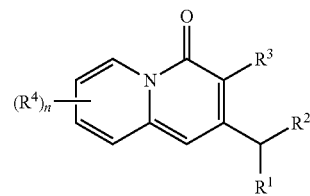

(I)

wherein, $R^1$ is selected from a)

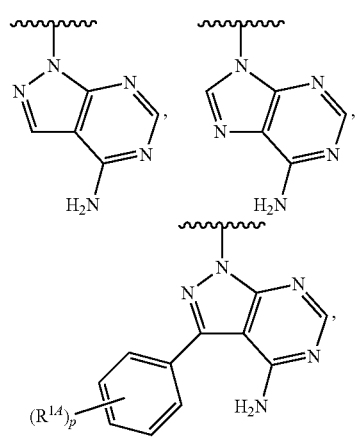

-continued

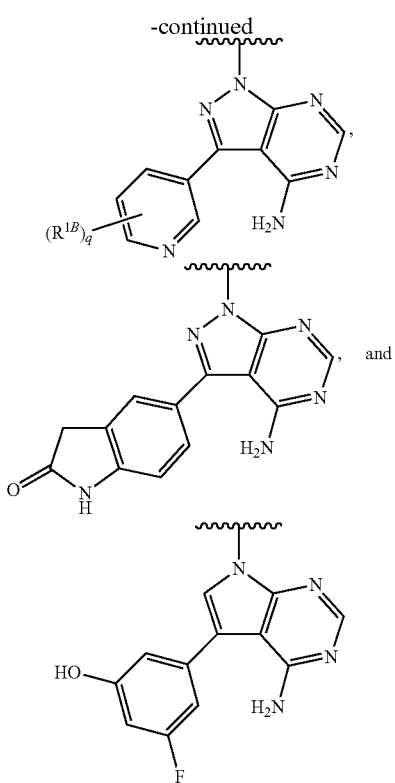

wherein,
$R^{1A}$ is independently selected at each occurrence from halogen, hydroxy, hydroxyalkyl, and —NHSO$_2$CH$_3$;
$R^{1B}$ is independently selected at each occurrence from hydroxy, alkoxy and —NHSO$_2$CH$_3$; or b) —NH—$R^{1a}$; wherein $R^{1a}$ is selected from

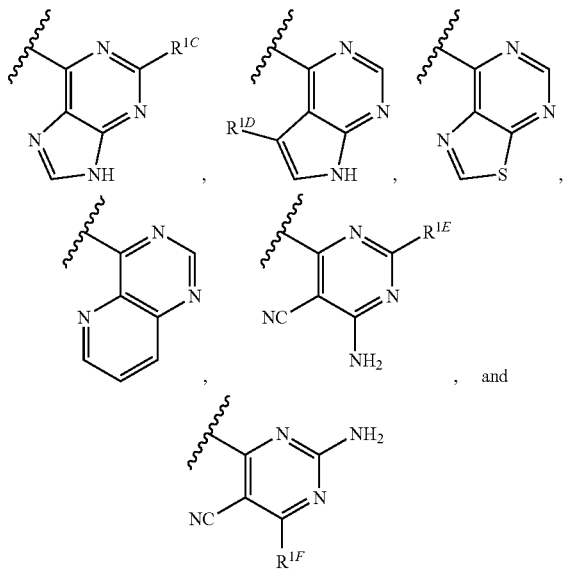

wherein,
$R^{1C}$ is selected from hydrogen, halogen, and amino; $R^{1D}$ is selected from halogen and cyano; $R^{1E}$ is selected from hydrogen and amino; $R^{1F}$ is selected from hydrogen, halogen, and alkyl;

$R^2$ is selected from hydrogen, substituted- or unsubstituted-alkyl, hydroxyalkyl, —OR$^5$, (CH$_2$)$_m$NR$^6$R$^7$, and ⁻C(=O)—NR$^6$R$^7$;

$R^3$ is selected from substituted- or unsubstituted aryl, substituted- or unsubstituted cycloalkyl, and substituted- or unsubstituted cycloalkenyl;

$R^4$ is independently selected at each occurrence from halogen, substituted- or unsubstituted-alkyl, substituted- or unsubstituted-aryl, substituted- or unsubstituted-heteroaryl, substituted- or unsubstituted-heterocycle, substituted- or unsubstituted-carbocycle, and —OR$^5$;

$R^5$ is substituted- or unsubstituted-alkyl;

$R^6$ and $R^7$ are each independently selected from hydrogen and substituted- or unsubstituted-alkyl;

n is an integer selected from 0, 1, and 2;
m is an integer selected from 1, 2, 3, and 4;
p is an integer selected from 0, 1, and 2; and
q is an integer selected from 0, 1, and 2;

wherein:
when an 'alkyl' group is substituted, it is substituted with 1 to 3 substituents independently selected from oxo (=O), halogen, nitro, cyano, perhaloalkyl, cycloalkyl, cycloalkenyl, aryl, heteroaryl, heterocyclyl, —OR$^{8b}$, —SO$_2$R$^{8a}$, —C(=O)OR$^{8a}$, —OC(=O)R$^{8a}$, —C(=O)N(H)R$^8$, —C(=O)N(alkyl)R$^8$, —N(H)C(=O)R$^{8a}$, —N(H)R$^8$, and —N(alkyl)R$^8$;

when 'cycloalkyl', 'cycloalkenyl' and 'carbocycle' are substituted, each of them is substituted with 1 to 3 substituents independently selected from oxo (=O), halogen, nitro, cyano, alkyl, alkenyl, cycloalkyl, cycloalkenyl, perhaloalkyl, aryl, heteroaryl, heterocyclyl, —OR$^{8b}$, —SO$_2$R$^{8a}$, —C(=O)R$^{8a}$, —C(=O)OR$^{8a}$, —OC(=O)R$^{8a}$, —C(=O)N(H)R$^8$, —C(=O)N(alkyl)R$^8$, —N(H)C(=O)R$^{8a}$, —N(H)R$^8$, and —N(alkyl)R$^8$;

when the 'aryl' group is substituted, it is substituted with 1 to 3 substituents independently selected from halogen, nitro, cyano, hydroxy, alkyl, alkenyl, perhaloalkyl, cycloalkyl, cycloalkenyl, heterocyclyl, aryl, heteroaryl, —O-alkyl, —O-perhaloalkyl, —N(alkyl)alkyl, —N(H)alkyl, —NH$_2$, —SO$_2$-alkyl, —SO$_2$-perhaloalkyl, —N(alkyl)C(=O)alkyl, —N(H)C(=O)alkyl, —C(=O)N(alkyl)alkyl, —C(=O)N(H)alkyl, —C(=O)NH$_2$, —SO$_2$N(alkyl)alkyl, —SO$_2$N(H)alkyl, —SO$_2$NH$_2$, —C(=O)OH, and —C(=O)O-alkyl;

when the 'heteroaryl' group is substituted, it is substituted with 1 to 3 substituents independently selected from halogen, cyano, hydroxy, alkyl, alkenyl, perhaloalkyl, cycloalkyl, cycloalkenyl, heterocyclyl, —O-alkyl, O-perhaloalkyl, —N(alkyl)alkyl, —N(H) alkyl, —NH$_2$, —SO$_2$-alkyl, —SO$_2$-perhaloalkyl, —N(alkyl)C(=O)alkyl, —N(H)C(=O)alkyl, —C(=O)N(alkyl)alkyl, —C(=O)N(H)alkyl, —C(=O)NH$_2$, —SO$_2$N(alkyl)alkyl, —SO$_2$N(H) alkyl, —SO$_2$NH$_2$, —C(=O)OH, and —C(=O)O-alkyl;

when the 'heterocyclyl' and 'heterocycle' are substituted, each of them is substituted either on a ring carbon atom or on a ring hetero atom, and when it is substituted on a ring carbon atom, it is substituted with 1 to 3 substituents independently selected from halogen, nitro, cyano, oxo (=O), alkyl, alkenyl, perhaloalkyl, cycloalkyl, cycloalkenyl, aryl, heteroaryl, heterocyclyl, —SO$_2$R$^{8a}$, —OR$^{8b}$, —C(=O)

OR⁸ᵃ, —OC(=O)R⁸ᵃ, —C(=O)N(H)R⁸, —C(=O)N(alkyl)R⁸, —N(H)C(=O)R⁸ᵃ, —N(H)R⁸, and —N(alkyl)R⁸; and when the heterocyclic group is substituted on a ring nitrogen, it is substituted with substituents independently selected from alkyl, alkenyl, hydroxyalkyl, cycloalkyl, cycloalkenyl, aryl, heteroaryl, —SO₂R⁸ᵃ, —C(=O)R⁸ᶜ, C(=O)OR⁸ᵃ, —C(=O)N(H)R⁸, and —C(=O)N(alkyl)R⁸;

R⁸ is selected from the group consisting of hydrogen, alkyl, alkenyl, cycloalkyl, cycloalkenyl, aryl, heteroaryl, and heterocyclyl;

R⁸ᵃ is selected from the group consisting of alkyl, alkenyl, perhaloalkyl, cycloalkyl, cycloalkenyl, aryl, heteroaryl, and heterocyclyl;

R⁸ᵇ is selected from the group consisting of hydrogen, alkyl, alkenyl, perhaloalkyl, cycloalkyl, cycloalkenyl, aryl, heteroaryl, and heterocyclyl; and R⁸ᶜ is selected from the group consisting of alkyl, hydroxyalkyl, alkenyl, perhaloalkyl, cycloalkyl, cycloalkenyl, aryl, heteroaryl, and heterocyclyl.

2. The compound of formula (I), its tautomeric form, its stereoisomer, or its pharmaceutically acceptable salt, as claimed in claim 1, wherein R¹ is selected from a)

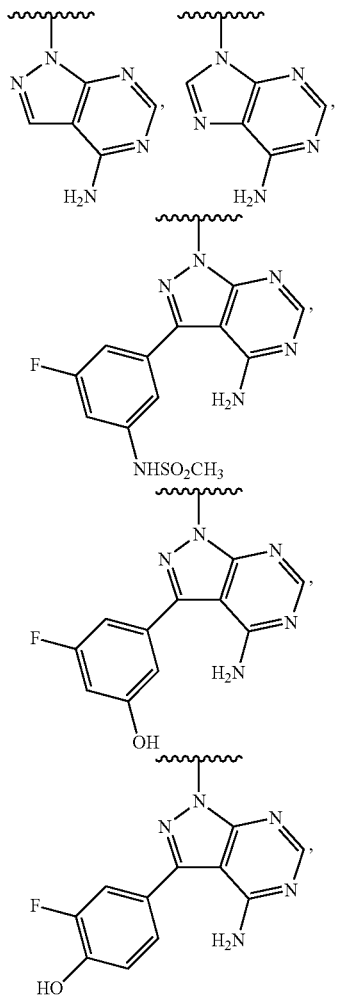

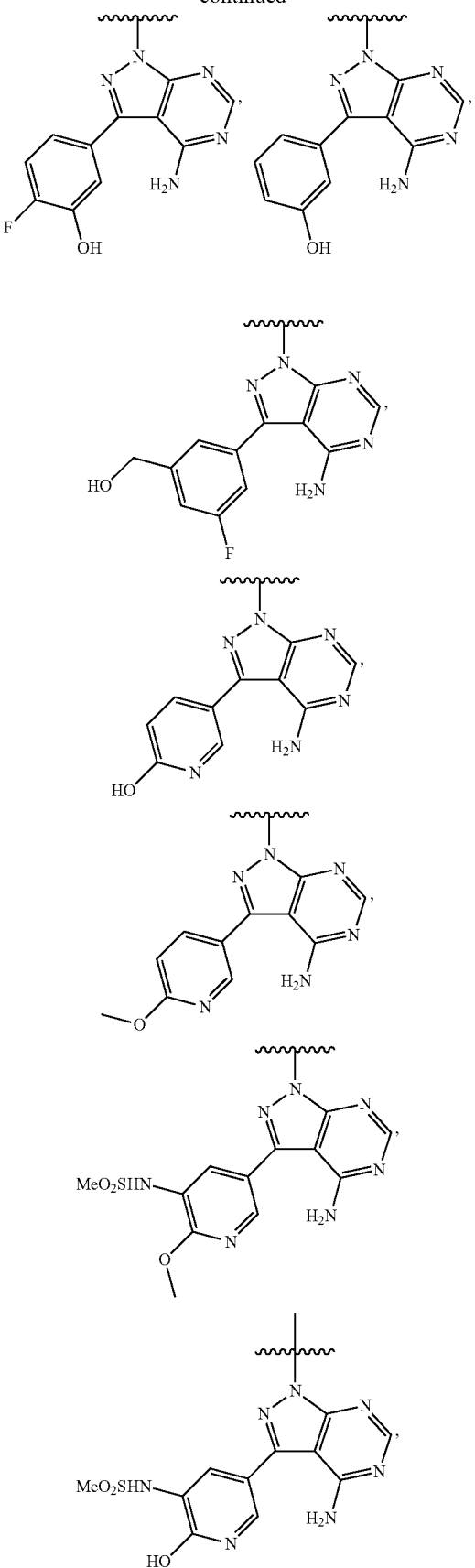

-continued

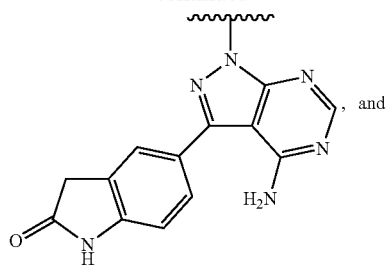
, and

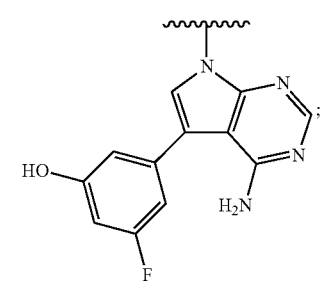
;

b) —NH—R$^{1a}$; wherein R$^{1a}$ is selected from

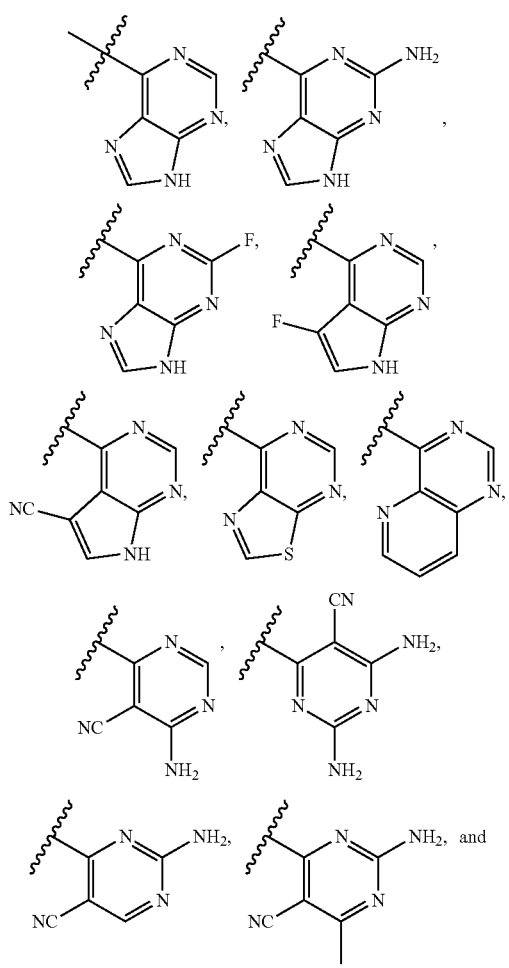

-continued

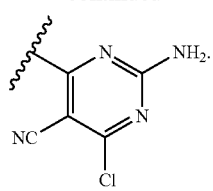

3. The compound of formula (I), its tautomeric form, its stereoisomer, or its pharmaceutically acceptable salt, as claimed in claim 1, wherein R$^2$ is selected from hydrogen and alkyl.

4. The compound of formula (I), its tautomeric form, its stereoisomer, or its pharmaceutically acceptable salt, as claimed in claim 1, wherein R$^3$ is substituted- or unsubstituted aryl.

5. The compound of formula (I), its tautomeric form, its stereoisomer, or its pharmaceutically acceptable salt, as claimed in claim 1, wherein R$^3$ is selected from phenyl, 3-fluorophenyl, 4-fluorophenyl, 3,5-difluorophenyl, 3,4-difluorophenyl, 3-fluoro-5-methylphenyl, 3-methylphenyl and 3-trifluoromethoxyphenyl.

6. The compound of formula (I), its tautomeric form, its stereoisomer, or its pharmaceutically acceptable salt, as claimed in claim 1, wherein R$^4$ is independently selected at each occurrence from halogen and alkyl.

7. The compound of formula (I), its tautomeric form, its stereoisomer, or its pharmaceutically acceptable salt, as claimed in claim 1, wherein R$^1$ is selected from c)

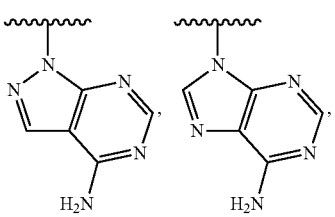

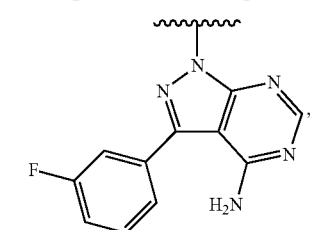

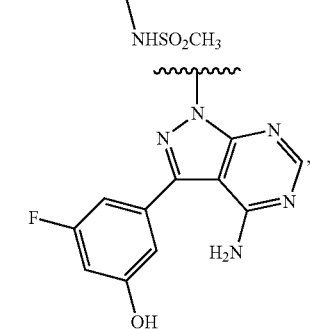

97
-continued
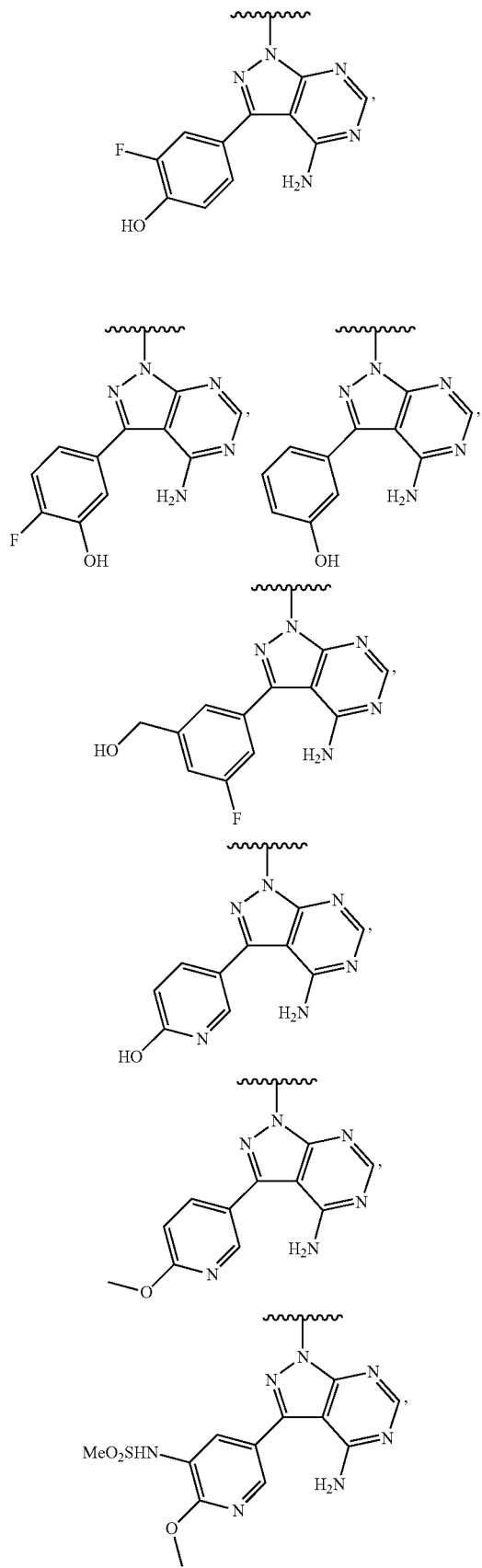
98
-continued
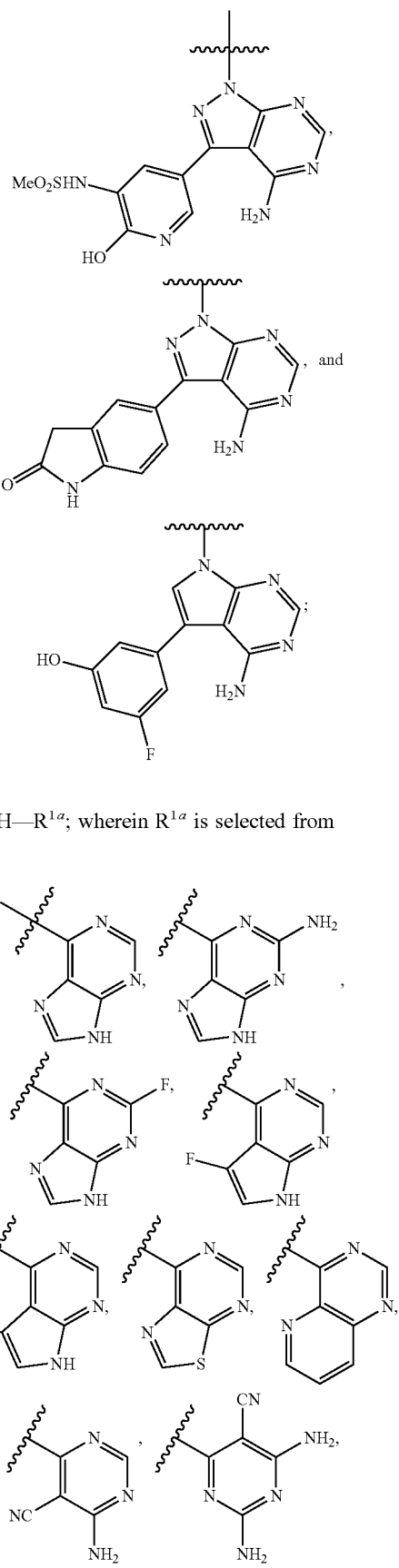
d) —NH—R$^{1a}$; wherein R$^{1a}$ is selected from

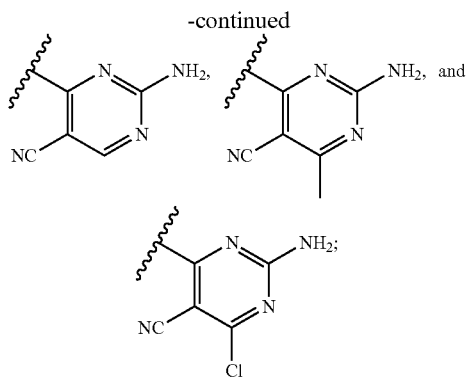

R² is selected from hydrogen and alkyl;
R³ is substituted- or unsubstituted aryl; and
R⁴ is independently selected at each occurrence from halogen and alkyl.

8. The compound of formula (I), its tautomeric form, its stereoisomer, or its pharmaceutically acceptable salt, as claimed in claim 1, wherein the compound is selected from:
2-(1-((9H-purin-6-yl)amino)ethyl)-3-phenyl-4H-quinolizin-4-one;
2-(1-((9H-purin-6-yl)amino)ethyl)-6-methyl-3-phenyl-4H-quinolizin-4-one;
2-(1-((9H-purin-6-yl)amino)ethyl)-7-methyl-3-phenyl-4H-quinolizin-4-one;
4-Amino-6-((1-(4-oxo-3-phenyl-4H-quinolizin-2-yl)ethyl)amino)pyrimidine-5-carbonitrile;
2-(1-((9H-purin-6-yl)amino)ethyl)-3-(3-fluorophenyl)-4H-quinolizin-4-one;
4-Amino-6-((1-(3-(3-fluorophenyl)-4-oxo-4H-quinolizin-2-yl)ethyl)amino)-pyrimidine-5-carbonitrile;
4-Amino-6-((1-(6-methyl-4-oxo-3-phenyl-4H-quinolizin-2-yl)ethyl)amino)-pyrimidine-5-carbonitrile;
2-(1-((2-Amino-9H-purin-6-yl)amino)ethyl)-6-methyl-3-phenyl-4H-quinolizin-4-one;
2-(1-((2-Fluoro-9H-purin-6-yl)amino)ethyl)-6-methyl-3-phenyl-4H-quinolizin-4-one;
4-Amino-6-((1-(3-(3-fluorophenyl)-6-methyl-4-oxo-4H-quinolizin-2-yl)amino)pyrimidine-5-carbonitrile;
2-(1-((9H-purin-6-yl)amino)ethyl)-3-(3-fluorophenyl)-6-methyl-4H-quinolizin-4-one;
2-(1-((2-Amino-9H-purin-6-yl)amino)ethyl)-3-(3-fluorophenyl)-6-methyl-4H-quinolizin-4-one;
2-(1-((9H-purin-6-yl)amino)ethyl)-7-fluoro-3-phenyl-4H-quinolizin-4-one;
4-Amino-6-((1-(7-fluoro-4-oxo-3-phenyl-4H-quinolizin-2-yl)ethyl)amino)-pyrimidine-5-carbonitrile;
2-(1-((2-Amino-9H-purin-6-yl)amino)ethyl)-7-fluoro-3-(3-fluorophenyl)-4H-quinolizin-4-one;
4-Amino-6-((1-(7-fluoro-3-(3-fluorophenyl)-4-oxo-4H-quinolizin-2-yl)ethyl)amino)pyrimidine-5-carbonitrile;
4-Amino-6-((1-(3-(3,5-difluorophenyl)-6-methyl-4-oxo-4H-quinolizin-2-yl)ethyl)amino)pyrimidine-5-carbonitrile;
2-(1-((2-amino-9H-purin-6-yl)amino)ethyl)-3-(3,5-difluorophenyl)-6-methyl-4H-quinolizin-4-one;
4-Amino-6-((1-(3-(3,4-difluorophenyl)-6-methyl-4-oxo-4H-quinolizin-2-yl)ethyl)amino)pyrimidine-5-carbonitrile;
2-Amino-4-((1-(7-fluoro-3-(3-fluorophenyl)-4-oxo-4H-quinolizin-2-yl)ethyl)amino)pyrimidine-5-carbonitrile;
2-Amino-4-((1-(7-fluoro-3-(3-fluorophenyl)-4-oxo-4H-quinolizin-2-yl)ethyl)amino)-6-methylpyrimidine-5-carbonitrile;
4-Amino-6-((1-(7-fluoro-6-methyl-4-oxo-3-phenyl-4H-quinolizin-2-yl)ethyl)amino)pyrimidine-5-carbonitrile;
4-Amino-6-((1-(7-fluoro-3-(3-fluorophenyl)-6-methyl-4-oxo-4H-quinolizin-2-yl)ethyl)amino)pyrimidine-5-carbonitrile;
2-(1-((9H-purin-6-yl)amino)ethyl)-7-fluoro-6-methyl-3-phenyl-4H-quinolizin-4-one;
(S)-2,4-diamino-6-((1-(7-fluoro-4-oxo-3-phenyl-4H-quinolizin-2-yl)ethyl)amino)-pyrimidine-5-carbonitrile;
(S)-2-amino-4-((1-(7-fluoro-4-oxo-3-phenyl-4H-quinolizin-2-yl)ethyl)amino)pyrimidine-5-carbonitrile;
(S)-2-amino-4-((1-(7-fluoro-4-oxo-3-phenyl-4H-quinolizin-2-yl)ethyl)amino)-6-methylpyrimidine-5-carbonitrile;
(S)-4-((1-(7-fluoro-4-oxo-3-phenyl-4H-quinolizin-2-yl)ethyl)amino)-7H-pyrrolo[2,3-d]pyrimidine-5-carbonitrile;
(S)-4-amino-6-((1-(7-fluoro-3-(3-fluoro-5-methylphenyl)-4-oxo-4H-quinolizin-2-yl)ethyl)amino)pyrimidine-5-carbonitrile;
(S)-2,4-diamino-6-((1-(7-fluoro-3-(3-fluoro-5-methylphenyl)-4-oxo-4H-quinolizin-2-yl)ethyl)amino)pyrimidine-5-carbonitrile;
(S)-4-amino-6-((1-(7-fluoro-4-oxo-3-(m-tolyl)-4H-quinolizin-2-yl)ethyl)amino)pyrimidine-5-carbonitrile;
(S)-2,4-diamino-6-((1-(7-fluoro-4-oxo-3-(m-tolyl)-4H-quinolizin-2-yl)ethyl)-amino)pyrimidine-5-carbonitrile;
(S)-2-(1-((2-amino-9H-purin-6-yl)amino)ethyl)-7-fluoro-3-phenyl-4H-quinolizin-4-one;
(S)-4-amino-6-((1-(7-fluoro-4-oxo-3-(3-(trifluoromethoxy)phenyl)-4H-quinolizin-2-yl)ethyl)amino)pyrimidine-5-carbonitrile;
(S)-2-(1-((2-amino-9H-purin-6-yl)amino)ethyl)-7-fluoro-3-(3-(trifluoromethoxy)-phenyl)-4H-quinolizin-4-one;
(S)-4-amino-6-((1-(7-fluoro-3-(4-fluorophenyl)-4-oxo-4H-quinolizin-2-yl)ethyl)amino)pyrimidine-5-carbonitrile;
(S)-2,4-diamino-6-((1-(7-fluoro-3-(4-fluorophenyl)-4-oxo-4H-quinolizin-2-yl)ethyl)amino)pyrimidine-5-carbonitrile;
(S)-2-(1-((9H-purin-6-yl)amino)ethyl)-7-fluoro-3-(4-fluorophenyl)-4H-quinolizin-4-one;
(S)-2-(1-((2-amino-9H-purin-6-yl)amino)ethyl)-7-fluoro-3-(4-fluorophenyl)-4H-quinolizin-4-one;
(S)-7-fluoro-2-(1-((5-fluoro-7H-pyrrolo[2,3-d]pyrimidin-4-yl)amino)ethyl)-3-phenyl-4H-quinolizin-4-one;
4-Amino-6-((1-(7-fluoro-4-oxo-3-phenyl-4H-quinolizin-2-yl)propyl)amino)pyrimidine-5-carbonitrile;
2,4-diamino-6-((1-(7-fluoro-4-oxo-3-phenyl-4H-quinolizin-2-yl)propyl)amino)pyrimidine-5-carbonitrile;
2-(1-((9H-purin-6-yl)amino)propyl)-7-fluoro-3-phenyl-4H-quinolizin-4-one;
4-Amino-6-((1-(7-fluoro-3-(3-fluorophenyl)-4-oxo-4H-quinolizin-2-yl)propyl)amino)pyrimidine-5-carbonitrile;
2,4-diamino-6-((1-(7-fluoro-3-(3-fluorophenyl)-4-oxo-4H-quinolizin-2-yl)propyl)amino)pyrimidine-5-carbonitrile;
2-(1-((9H-purin-6-yl)amino)propyl)-7-fluoro-3-(3-fluorophenyl)-4H-quinolizin-4-one;
2-(1-((2-amino-9H-purin-6-yl)amino)propyl)-7-fluoro-3-(3-fluorophenyl)-4H-quinolizin-4-one;

(S)-4-amino-6-((1-(3-(3,5-difluorophenyl)-7-fluoro-4-oxo-4H-quinolizin-2-yl)ethyl)amino)pyrimidine-5-carbonitrile;

(S)-2,4-diamino-6-((1-(3-(3,5-difluorophenyl)-7-fluoro-4-oxo-4H-quinolizin-2-yl)ethyl)amino)pyrimidine-5-carbonitrile;

(S)-2-(1-((9H-purin-6-yl)amino)ethyl)-3-(3,5-difluorophenyl)-7-fluoro-4H-quinolizin-4-one;

(S)-2-(1-((2-amino-9H-purin-6-yl)amino)ethyl)-3-(3,5-difluorophenyl)-7-fluoro-4H-quinolizin-4-one;

(S)-7-fluoro-3-phenyl-2-(1-(thiazolo[5,4-d]pyrimidin-7-ylamino)ethyl)-4H-quinolizin-4-one;

(S)-2-amino-4-chloro-6-((1-(7-fluoro-4-oxo-3-phenyl-4H-quinolizin-2-yl)ethyl)amino)pyrimidine-5-carbonitrile;

(S)-7-fluoro-3-phenyl-2-(1-(pyrido[3,2-d]pyrimidin-4-ylamino)ethyl)-4H-quinolizin-4-one;

2-((4-Amino-1H-pyrazolo[3,4-d]pyrimidin-1-yOmethyl)-6-methyl-3-phenyl-4H-quinolizin-4-one;

2-((6-Amino-9H-purin-9-yl)methyl)-3-phenyl-4H-quinolizin-4-one;

2-(1-(4-Amino-1H-pyrazolo[3,4-d]pyrimidin-1-yl)ethyl)-3-(3-fluorophenyl)-6-methyl-4H-quinolizin-4-one;

N-(3-(4-amino-1-(1-(7-fluoro-4-oxo-3-phenyl-4H-quinolizin-2-yl)ethyl)-1H-pyrazolo[3,4-d]pyrimidin-3-yl)-5-fluorophenyl)methanesulfonamide;

2-(1-(4-amino-3-(3-fluoro-5-hydroxyphenyl)-1H-pyrazolo[3,4-d]pyrimidin-1-yl)ethyl)-7-fluoro-3-phenyl-4H-quinolizin-4-one;

2-(1-(4-amino-3-(3-fluoro-4-hydroxyphenyl)-1H-pyrazolo[3,4-d]pyrimidin-1-yl)ethyl)-7-fluoro-3-phenyl-4H-quinolizin-4-one;

2-(1-(4-amino-3-(4-fluoro-3-hydroxyphenyl)-1H-pyrazolo[3,4-d]pyrimidin-1-yl)ethyl)-7-fluoro-3-phenyl-4H-quinolizin-4-one;

2-(1-(4-amino-3-(3-hydroxyphenyl)-1H-pyrazolo[3,4-d]pyrimidin-1-yl)ethyl)-7-fluoro-3-phenyl-4H-quinolizin-4-one;

2-(1-(4-amino-5-(3-fluoro-5-hydroxyphenyl)-7H-pyrrolo[2,3-d]pyrimidin-7-yl)ethyl)-7-fluoro-3-phenyl-4H-quinolizin-4-one;

2-(1-(4-amino-3-(6-methoxypyridin-3-yl)-1H-pyrazolo[3,4-d]pyrimidin-1-yl)ethyl)-7-fluoro-3-phenyl-4H-quinolizin-4-one;

2-(1-(4-amino-3-(2-oxoindolin-5-yl)-1H-pyrazolo[3,4-d]pyrimidin-1-yl)ethyl)-7-fluoro-3-phenyl-4H-quinolizin-4-one;

(S)-2-(1-(4-amino-3-(6-hydroxypyridin-3-yl)-1H-pyrazolo[3,4-d]pyrimidin-1-yl)ethyl)-7-fluoro-3-phenyl-4H-quinolizin-4-one;

N-(5-(4-amino-1-(1-(7-fluoro-4-oxo-3-phenyl-4H-quinolizin-2-yl)ethyl)-1H-pyrazolo[3,4-d]pyrimidin-3-yl)-2-methoxypyridin-3-yl)methanesulfonamide;

(S)—N-(5-(4-amino-1-(1-(7-fluoro-4-oxo-3-phenyl-4H-quinolizin-2-yl)ethyl)-1H-pyrazolo[3,4-d]pyrimidin-3-yl)-2-hydroxypyridin-3-yl)methanesulfonamide; and 2-(1-(4-amino-3-(3-fluoro-5-(hydroxymethyl)phenyl)-1H-pyrazolo[3,4-d]pyrimidin-1-yl)ethyl)-7-fluoro-3-phenyl-4H-quinolizin-4-one.

9. The compound of formula (I), its tautomeric form, its stereoisomer, or its pharmaceutically acceptable salt, as claimed in claim 1, wherein the compound is selected from:

2-(1-((9H-purin-6-yl)amino)ethyl)-6-methyl-3-phenyl-4H-quinolizin-4-one;

4-Amino-6-((1-(4-oxo-3-phenyl-4H-quinolizin-2-yl)ethyl)amino)pyrimidine-5-carbonitrile;

2-(1-((9H-purin-6-yl)amino)ethyl)-3-(3-fluorophenyl)-4H-quinolizin-4-one;

4-Amino-6-((1-(3-(3-fluorophenyl)-4-oxo-4H-quinolizin-2-yl)ethyl)amino)-pyrimidine-5-carbonitrile;

4-Amino-6-((1-(6-methyl-4-oxo-3-phenyl-4H-quinolizin-2-yl)ethyl)amino)-pyrimidine-5-carbonitrile;

2-(1-((2-Amino-9H-purin-6-yl)amino)ethyl)-6-methyl-3-phenyl-4H-quinolizin-4-one;

2-(1-((2-Fluoro-9H-purin-6-yl)amino)ethyl)-6-methyl-3-phenyl-4H-quinolizin-4-one;

4-Amino-6-((1-(3-(3-fluorophenyl)-6-methyl-4-oxo-4H-quinolizin-2-yl)ethyl)amino)pyrimidine-5-carbonitrile;

2-(1-((9H-purin-6-yl)amino)ethyl)-3-(3-fluorophenyl)-6-methyl-4H-quinolizin-4-one;

2-(1-((2-Amino-9H-purin-6-yl)amino)ethyl)-3-(3-fluorophenyl)-6-methyl-4H-quinolizin-4-one;

2-(1-((9H-purin-6-yl)amino)ethyl)-7-fluoro-3-phenyl-4H-quinolizin-4-one;

4-Amino-6-((1-(7-fluoro-4-oxo-3-phenyl-4H-quinolizin-2-yl)ethyl)amino)-pyrimidine-5-carbonitrile;

2-(1-((2-Amino-9H-purin-6-yl)amino)ethyl)-7-fluoro-3-(3-fluorophenyl)-4H-quinolizin-4-one;

4-Amino-6-((1-(7-fluoro-3-(3-fluorophenyl)-4-oxo-4H-quinolizin-2-yl)ethyl)amino)pyrimidine-5-carbonitrile;

4-Amino-6-((1-(3-(3,5-difluorophenyl)-6-methyl-4-oxo-4H-quinolizin-2-yl)ethyl)amino)pyrimidine-5-carbonitrile;

2-(1-((2-amino-9H-purin-6-yl)amino)ethyl)-3-(3,5-difluorophenyl)-6-methyl-4H-quinolizin-4-one;

4-Amino-6-((1-(3-(3,4-difluorophenyl)-6-methyl-4-oxo-4H-quinolizin-2-yl)ethyl)amino)pyrimidine-5-carbonitrile;

2-Amino-4-((1-(7-fluoro-3-(3-fluorophenyl)-4-oxo-4H-quinolizin-2-yl)ethyl)amino)pyrimidine-5-carbonitrile;

2-Amino-4-((1-(7-fluoro-3-(3-fluorophenyl)-4-oxo-4H-quinolizin-2-yl)ethyl)amino)-6-methylpyrimidine-5-carbonitrile;

4-Amino-6-((1-(7-fluoro-6-methyl-4-oxo-3-phenyl-4H-quinolizin-2-yl)ethyl)amino)pyrimidine-5-carbonitrile;

4-Amino-6-((1-(7-fluoro-3-(3-fluorophenyl)-6-methyl-4-oxo-4H-quinolizin-2-yl)ethyl)amino)pyrimidine-5-carbonitrile;

2-(1-((9H-purin-6-yl)amino)ethyl)-7-fluoro-6-methyl-3-phenyl-4H-quinolizin-4-one;

(S)-2,4-diamino-6-((1-(7-fluoro-4-oxo-3-phenyl-4H-quinolizin-2-yl)ethyl)amino)-pyrimidine-5-carbonitrile;

(S)-2-amino-4-((1-(7-fluoro-4-oxo-3-phenyl-4H-quinolizin-2-yl)ethyl)amino)pyrimidine-5-carbonitrile;

(S)-2-amino-4-((1-(7-fluoro-4-oxo-3-phenyl-4H-quinolizin-2-yl)ethyl)amino)-6-methylpyrimidine-5-carbonitrile;

(S)-4-((1-(7-fluoro-4-oxo-3-phenyl-4H-quinolizin-2-yl)ethyl)amino)-7H-pyrrolo[2,3-d]pyrimidine-5-carbonitrile;

(S)-4-amino-6-((1-(7-fluoro-3-(3-fluoro-5-methylphenyl)-4-oxo-4H-quinolizin-2-yl)ethyl)amino)pyrimidine-5-carbonitrile;

(S)-2,4-diamino-6-((1-(7-fluoro-3-(3-fluoro-5-methylphenyl)-4-oxo-4H-quinolizin-2-yl)ethyl)amino)pyrimidine-5-carbonitrile;

(S)-4-amino-6-((1-(7-fluoro-4-oxo-3-(m-tolyl)-4H-quinolizin-2-yl)ethyl)amino)pyrimidine-5-carbonitrile;

(S)-2,4-diamino-6-((1-(7-fluoro-4-oxo-3-(m-tolyl)-4H-quinolizin-2-yl)ethyl)-amino)pyrimidine-5-carbonitrile;

(S)-2-(1-((2-amino-9H-purin-6-yl)amino)ethyl)-7-fluoro-3-phenyl-4H-quinolizin-4-one;

(S)-4-amino-6-((1-(7-fluoro-4-oxo-3-(3-(trifluoromethoxy)phenyl)-4H-quinolizin-2-yl)ethyl)amino)pyrimidine-5-carbonitrile;

(S)-4-amino-6-((1-(7-fluoro-3-(4-fluorophenyl)-4-oxo-4H-quinolizin-2-yl)ethyl)amino)pyrimidine-5-carbonitrile;

(S)-7-fluoro-2-(1-((5-fluoro-7H-pyrrolo[2,3-d]pyrimidin-4-yl)amino)ethyl)-3-phenyl-4H-quinolizin-4-one;

4-Amino-6-((1-(7-fluoro-4-oxo-3-phenyl-4H-quinolizin-2-yl)propyl)amino)pyrimidine-5-carbonitrile;

2,4-diamino-6-((1-(7-fluoro-4-oxo-3-phenyl-4H-quinolizin-2-yl)propyl)amino)pyrimidine-5-carbonitrile;

4-Amino-6-((1-(7-fluoro-3-(3-fluorophenyl)-4-oxo-4H-quinolizin-2-yl)propyl)amino)pyrimidine-5-carbonitrile;

2,4-diamino-6-((1-(7-fluoro-3-(3-fluorophenyl)-4-oxo-4H-quinolizin-2-yl)propyl)amino)pyrimidine-5-carbonitrile;

2-(1-((2-amino-9H-purin-6-yl)amino)propyl)-7-fluoro-3-(3-fluorophenyl)-4H-quinolizin-4-one;

(S)-4-amino-6-((1-(3-(3,5-difluorophenyl)-7-fluoro-4-oxo-4H-quinolizin-2-yl)ethyl)amino)pyrimidine-5-carbonitrile;

(S)-2,4-diamino-6-((1-(3-(3,5-difluorophenyl)-7-fluoro-4-oxo-4H-quinolizin-2-yl)ethyl)amino)pyrimidine-5-carbonitrile;

(S)-2-(1-((9H-purin-6-yl)amino)ethyl)-3-(3,5-difluorophenyl)-7-fluoro-4H-quinolizin-4-one;

(S)-2-(1-((2-amino-9H-purin-6-yl)amino)ethyl)-3-(3,5-difluorophenyl)-7-fluoro-4H-quinolizin-4-one;

(S)-7-fluoro-3-phenyl-2-(1-(thiazolo[5,4-d]pyrimidin-7-ylamino)ethyl)-4H-quinolizin-4-one;

(S)-2-amino-4-chloro-6-((1-(7-fluoro-4-oxo-3-phenyl-4H-quinolizin-2-yl)ethyl)amino)pyrimidine-5-carbonitrile;

(S)-7-fluoro-3-phenyl-2-(1-(pyrido[3,2-d]pyrimidin-4-ylamino)ethyl)-4H-quinolizin-4-one;

N-(3-(4-amino-1-(1-(7-fluoro-4-oxo-3-phenyl-4H-quinolizin-2-yl)ethyl)-1H-pyrazolo[3,4-d]pyrimidin-3-yl)-5-fluorophenyl)methanesulfonamide;

2-(1-(4-amino-3-(3-fluoro-5-hydroxyphenyl)-1H-pyrazolo[3,4-d]pyrimidin-1-yl)ethyl)-7-fluoro-3-phenyl-4H-quinolizin-4-one;

2-(1-(4-amino-3-(3-fluoro-4-hydroxyphenyl)-1H-pyrazolo[3,4-d]pyrimidin-1-yl)ethyl)-7-fluoro-3-phenyl-4H-quinolizin-4-one;

2-(1-(4-amino-3-(4-fluoro-3-hydroxyphenyl)-1H-pyrazolo[3,4-d]pyrimidin-1-yl)ethyl)-7-fluoro-3-phenyl-4H-quinolizin-4-one;

2-(1-(4-amino-3-(3-hydroxyphenyl)-1H-pyrazolo[3,4-d]pyrimidin-1-yl)ethyl)-7-fluoro-3-phenyl-4H-quinolizin-4-one;

2-(1-(4-amino-5-(3-fluoro-5-hydroxyphenyl)-7H-pyrrolo[2,3-d]pyrimidin-7-yl)ethyl)-7-fluoro-3-phenyl-4H-quinolizin-4-one;

2-(1-(4-amino-3-(6-methoxypyridin-3-yl)-1H-pyrazolo[3,4-d]pyrimidin-1-yl)ethyl)-7-fluoro-3-phenyl-4H-quinolizin-4-one;

2-(1-(4-amino-3-(2-oxoindolin-5-yl)-1H-pyrazolo[3,4-d]pyrimidin-1-yl)ethyl)-7-fluoro-3-phenyl-4H-quinolizin-4-one; and N-(5-(4-amino-1-(1-(7-fluoro-4-oxo-3-phenyl-4H-quinolizin-2-yl)ethyl)-1H-pyrazolo[3,4-d]pyrimidin-3-yl)-2-methoxypyridin-3-yl)methanesulfonamide.

10. The compound of formula (I), its tautomeric form, its stereoisomer, or its pharmaceutically acceptable salt, as claimed in claim 1, wherein the compound is selected from:

4-amino-6-((1-(7-fluoro-4-oxo-3-phenyl-4H-quinolizin-2-yl)ethyl)amino)-pyrimidine-5-carbonitrile;

4-Amino-6-((1-(7-fluoro-3-(3-fluorophenyl)-4-oxo-4H-quinolizin-2-yl)ethyl)amino)pyrimidine-5-carbonitrile;

2-(1-((2-Amino-9H-purin-6-yl)amino)ethyl)-7-fluoro-3-(3-fluorophenyl)-4H-quinolizin-4-one;

(S)-2,4-diamino-6-((1-(7-fluoro-4-oxo-3-phenyl-4H-quinolizin-2-yl)ethyl)amino)-pyrimidine-5-carbonitrile; and 2-(1-(4-amino-3-(6-methoxypyridin-3-yl)-1H-pyrazolo[3,4-d]pyrimidin-1-yl)ethyl)-7-fluoro-3-phenyl-4H-quinolizin-4-one.

11. A pharmaceutical composition comprising the compound of claim 1, its tautomeric form, its stereoisomer, or its pharmaceutically acceptable salt, and a pharmaceutically acceptable carrier.

12. A method of inhibiting PI3K delta activity in a mammal in need thereof comprising administering to the mammal an effective amount of a compound, its tautomeric form, its stereoisomer, or its pharmaceutically acceptable salt, of claim 1.

13. A method of inhibiting PI3K delta activity in a mammal in need thereof comprising administering to the mammal an effective amount of a compound, its tautomeric form, its stereoisomer, or its pharmaceutically acceptable salt, of claim 8.

14. The method of claim 12, wherein the mammal in need thereof is suffering from transplant rejection, lymphocytic leukemia, or lymphoma.

15. The method of claim 14, wherein the lymphoma is non-Hodgkin lymphoma.

16. The method of claim 12, wherein the mammal in need thereof is suffering from a cancer selected from the group consisting of non-Hodgkin's lymphoma, follicular lymphoma, acute or chronic lymphocytic leukemia, Hodgkin's lymphoma, acute or chronic myeloid leukemia, myeloma, melanoma, B-cell lymphoma, diffuse large B-cell lymphoma, T-cell lymphoma, natural killer cell lymphoma, myeloproliferative neoplasms, myelodysplastic syndrome, mesothelioma, pancreatic, oesophageal, liver, cervical, endometrial, biliary, breast, ovarian, prostate, gastrointestinal, stomach, sarcoma, skin, colon, colorectal, non-small cell lung, bladder, gastrointestinal stromal, renal, central nervous system, brain, head or neck, thyroid, and testicular cancer.

17. The method of claim 12, wherein the mammal in need thereof is suffering from a cancer selected from the group consisting of acute myeloid leukemia, chronic lymphocytic Leukemia, chronic myelogenous leukemia, non-Hodgkin's lymphoma, Hodgkin's lymphoma, diffuse large B-cell lymphoma, small lymphocytic leukemia, follicular lymphoma, and multiple myeloma.

18. The method of claim 13, wherein the mammal in need thereof is suffering from a cancer selected from the group consisting of non-Hodgkin's lymphoma, follicular lymphoma, acute or chronic lymphocytic leukemia, Hodgkin's lymphoma, acute or chronic myeloid leukemia, myeloma, melanoma, B-cell lymphoma, diffuse large B-cell lymphoma, T-cell lymphoma, natural killer cell lymphoma, myeloproliferative neoplasms, myelodysplastic syndrome, mesothelioma, pancreatic, oesophageal, liver, cervical, endometrial, biliary, breast, ovarian, prostate, gastrointestinal, stomach, sarcoma, skin, colon, colorectal, non-small cell lung, bladder, gastrointestinal stromal, renal, central nervous system, brain, head or neck, thyroid, and testicular cancer.

19. The method of claim 12, wherein the mammal in need thereof is suffering from an auto-immune disease selected from the group consisting of Sjogren's syndrome, rheumatoid arthritis, allergy, psoriasis, asthma, chronic obstructive pulmonary disease, organ transplant rejection, glomerulonephritis, lupus, multiple sclerosis, Crohn's disease, activated PI3K delta syndrome, and inflammation.

20. The method of claim 13, wherein the mammal in need thereof is suffering from an auto-immune disease selected from the group consisting of Sjogren's syndrome, rheumatoid arthritis, allergy, psoriasis, asthma, chronic obstructive pulmonary disease, organ transplant rejection, glomerulonephritis, lupus, multiple sclerosis, Crohn's disease, activated PI3K delta syndrome, and inflammation.

21. The method of claim 12, wherein the mammal in need thereof is suffering from an inflammatory disease selected from the group consisting of chronic obstructive pulmonary disease, allergies, rheumatoid arthritis, asthma, and bronchitis.

22. The method of claim 13, wherein the mammal in need thereof is suffering from an inflammatory disease selected from the group consisting of chronic obstructive pulmonary disease, allergies, rheumatoid arthritis, asthma, and bronchitis.

\* \* \* \* \*

UNITED STATES PATENT AND TRADEMARK OFFICE
CERTIFICATE OF CORRECTION

PATENT NO. : 9,944,639 B2
APPLICATION NO. : 15/323565
DATED : April 17, 2018
INVENTOR(S) : Manojkumar Ramprasad Shukla et al.

It is certified that error appears in the above-identified patent and that said Letters Patent is hereby corrected as shown below:

In the Claims

In Claim 1, Line 18, please delete "alkoxy and" and add --alkoxy, and--

In Claim 1, Line 30, please delete "C(=O)-NR$^6$R$^7$" and add -- -C(=O)-NR$^6$R$^7$--

In Claim 5, Line 5, please delete "3-phenylmethyl and" and add --3-phenylmethyl, and--

In Claim 16, Line 9, please delete "mesothelioma, pancreatic," and add --mesothelioma, sarcoma, and pancreatic,--

In Claim 16, Line 11, please delete "stomach, sarcoma, skin," and add --stomach, skin,--

In Claim 18, Line 9, please delete "mesothelioma, pancreatic," and add --mesothelioma, sarcoma, and pancreatic,--

In Claim 18, Line 11, please delete "stomach, sarcoma, skin," and add --stomach, skin,--

Signed and Sealed this
Twenty-fourth Day of July, 2018

Andrei Iancu
*Director of the United States Patent and Trademark Office*